United States Patent [19]

Chiang

[11] Patent Number: 5,558,999
[45] Date of Patent: Sep. 24, 1996

[54] CHOLESTEROL 7α-HYDROXYLASE GENE REGULATORY ELEMENTS AND METHODS FOR USING THEM

[75] Inventor: John Y. L. Chiang, Stow, Ohio

[73] Assignee: Northeastern Ohio Universities, Rootstown, Ohio

[21] Appl. No.: 135,511

[22] Filed: Oct. 13, 1993

[51] Int. Cl.$^6$ .......................... C12N 15/11; C12N 15/18; C12N 15/55; C12Q 1/68
[52] U.S. Cl. .......................... 435/6; 435/240.2; 536/23.2; 536/24.1
[58] Field of Search .................. 435/240.1, 6, 171.3, 435/320.1, 240.2; 536/24.1, 23.2

[56] References Cited

PUBLICATIONS

Crestani et al. (1992) Faseb J. V6(4), A2626.
Sambrook et al (1989) "Molecular Cloning . . ." pp. 15.3–15.4, 15.14–15.19, 15.32–15.36, 15.51–15.52. CSH Lab. Press. CSH, N.Y.
Wasylyk (1988). Biochem. Biophys. Acta 951, 17–35.
Hylemon et al. (1992). J. Biol. Chem. 267(24), 16866–16871.
Pandak et al. (1991). J. Biol. Chem. 266(6), 3416–3421.
Pandak et al. (1992) J. Lipid. Res. 33, 659–668.
Karam, W. G. et al., "Polymorphisms of Human Cholesterol 7α–Hydroxylase", *Biochem. and Biophys. Res. Comm.* 185(2): 588–595 (1992).
Breslow, J. L. et al., "Transgenic Mouse Models of Lipoprotein Metabolism and Atherosclerosis", *Proc. Natl. Acad. Sci. USA* 90: 8314–8318 (1993).
Cohen, J. C. et al., "Cloning of the Human Cholesterol 7α–Hydroxylase Gene (CYP7) and Localization to Chromosome 8q11–q12", *Genomics* 14: 153–161 (1992).
Nishimoto, M. et al., "Structure of the Gene Encoding Human Liver Cholesterol 7α–Hydroxylase", *Biochimica. et Biophysica. Acta.* 1172: 147–150 (1992).
Thompson, J. F. et al., "Cholesterol 7α–Hydroxylase Promoter Separated from Cyclophilin Pseudogene By Alu Sequence", *Biochimica et Biophysica Acta* 1168: 239–242 (1993).
Li, Y. C. et al., "The Expression of a Catalytically Active Cholesterol 7α–Hydroxylase Cytochrome P450 in *Escherichia coli*", *The Journal of Biological Chemistry* 266(29): 19186–19191 (1991).
Molowa, D. T. et al., "Transcriptional Regulation of the Human Cholesterol 7α–Hydroxylase Gene", *Biochemistry* 31: 2539–2544 (1992).
Nishimoto, M. et al., "Structural Analysis of the Gene Encoding Rat Cholesterol α–Hydroxylase, The Key Enzyme for Bile . . . ", *The Journal of Biological Chemistry* 266(10): 6467–6471 (1991).
Jelinek, D. F. et al., "Structure of the Rat Gene Encoding Cholesterol 7α–Hydroxylase", *Biochemistry* 29(34): 7781–7785 (1990).
Chiang, J. Y. L. et al., "Cloning and 5'–Flanking Sequence of a Rat Cholesterol 7α–Hydroxylase", *Biochimica et Biophysica Acta* 1132: 337–339 (1992).
Lusis, Aldons J., "The Mouse Model for Atherosclerosis", *TCM* 3(4): 135–143 (1993).
Dueland, Svein et. al., "Effect of Dietary Cholesterol and Taurocholate on Cholesterol 7α–hydroxylase and Hepatic LDL Receptors in Inbred Mice", *Journal of Lipid Research* 34: 923–931 (1993).
Dueland, Svein et. al., "Expression of 7α–Hydroxylase in Non–hepatic Cell Results in Liver Phenotypic Resistance of the Low Density Lipoprotein Receptor to Cholesterol Repression", *Journal of Biological Chemistry* 267(32): 22695–22698 (1992).

*Primary Examiner*—Mindy Fleisher
*Assistant Examiner*—Philip W. Carter
*Attorney, Agent, or Firm*—Foley & Lardner

[57] ABSTRACT

DNA regulatory elements that control cholesterol 7α-hydroxylase expression are disclosed. A gene construct is provided comprising at least one regulatory element and a reporter gene is used in an assay to detect a compound that modulates cholesterol 7α-hydroxylase enzyme regulation. Thus, a method for screening compounds that inhibit or stimulate expression of the enzyme is provided, as well as a method for detecting and isolating the transcription factors of the cholesterol 7α-hydroxylase gene.

16 Claims, 32 Drawing Sheets

FIG. 4

```
                                              GRE                         LFA1 HRE
RAT     -191 ------GAGTATTGCAGCTCTCTGTTGTTCTGGAGCCTCTTCTGAGAC-TATGGACTTAGTT
             ******                ****     ****           ***    ***********
HAMSTER -252 TATCAAGTATTGAAGCTCTCTGCTTTGTTTTGGAGCCTCTTCTGATAC-TATGGACTTAGTT
             ******         *******      *     ****   *****    ************
HUMAN   -187 -------GTATTGCAGTGTCTGATTGCTTTGGAACCACTTCTGATACCTGTGGACTTAGTT
                                              PPRE/HRE
        -135 CAAGGCCGGGTAATGCTATTTTTTCTCTTTT----TCTAGTAGGAGGACAAATAG------
             *  ***        ****        ****      *********** *****
        -192 CAAGGCTGGGCAATACTA--TTTTT-TTCTTTTTTCTAATAGGAGGACAAATAG-TTAGT-
             * ****  ** *  *     ****   *****      *********** *****  **   *
        -132 CAAGGCCAGTTACTACCAC--TTTT----TTTTTTCTAATAGAATGAACAAATGGCTAAT
                 TGT3    HRE                                               TATA BOX
         -81 TGTTTGCTTTGGTCACTC-AAGTTCAAGTTATTGGATCATGGTCCT--GTGCACATATAAA-
             ******* ****   **  *******  ****** *********    ****** ******
        -136 TGTTTGCTTTGGTCA-TCCAAGTTCAAGTTATTGGATCATGGTCCTATGT---*TATAAAG
             ****** *****     *******  ****** ********      *    *******
         -78 TGTTTGCTTTG-TCAA-CCAAGTCAAGTTAATGGATC-TGGTACTATGT-----ATATAAAA
                               LFB1 CAAT BOX
         -23 -GTCTAGTCAGACCCCACTGTTTC-GGGACAGCCTTGCTTT-GCTAGGCAAAGAGTCTCCCCT-
             ********                ****  ********* *******             **
         -79 AGTCTAGTTTGAGCC-**-TTTCAGGGGCAGCCTTGCT*G-GCTAAGCACAGACTCTCCTCT-
             ********          ****  ********   **** *   ****** **    * **
         -23 AGCCTAGCTTGAGTCTCT-TTTCAGTGGCATCCTTCCCTTT-CTAATCAGAGA-TTTTCTTCC

37 TTGGAAATTTTCCTG-----CTTTTGCAAAAATG
             *  ******  ****      ****  *******
         -23 TGGGAG*TTTTCCTG-----CTTT-GCAAAATG
              *    ******          ***  ********
          38 TCAGAGATTTTTGGCCTAGA-TTT-GCAAAATG
```

FIG. 7A

MOLECULAR-WEIGHT 57658     #LENGTH 505

```
  1 MMTTSLIWGIAIAACCCLWLILGIRRQTG
 31 EPPLENGLIPYLGCALQFGANPLEFLRANQ
 61 RKHGHVFTCKLMGKYVHFITNPLSYHKVLC
 91 HGKYFDWKKFHFATSAKAFGHRSIDPMDGN
121 TTENINDTFIKTLQGHALNSLTESMMENLQ
151 RIMRPPVSSNKTAAWTEGMYSFCYRVMF
181 EAGYLTIFGRDLTRRDTQKAHILNNLDNFK
211 QFDKVFPALVAGLPIHMFRTAHNAREKLAE
241 SLRHENLQKRESISELISLRMFLNDTLSTF
271 DDLEKAKTHLVVLWASQANTIPATFWSLFQ
301 MIRNPEAMKAATEEVKRTLENAGQKVSLEG
331 NPICLSQAELNDLPVLDSIKESLRLSSAS
361 LNIRTAKEDFTLHLEDGSYNIRKDDIIALY
391 PQLMHLDPEIYPDPLTEKYDRYLDENGKTK
421 TTFYCNGLKLKYYYMPFGSGATICPGRLFA
451 IHEIKQFLILMLSYFELELIEGQAKCPPLD
481 QSRAGLGILPPLNDIEFKYKFKHL*
```

FIG. 7B

MOLECULAR-WEIGHT 56880     #LENGTH 504

```
  1  MMTISLIWGIAVLVSCCIWFIVGIRRRKAG
 31  EPPLENGLIPYLGCALKFGSNPLEEFLRANQ
 61  RKHGHVFTCKLMGKYVHFITNSLSYHKVLC
 91  HGKYFDWKKFHYTTSAKAFGHRSIDPNDGN
121  TTENINNTFTKTLQGDALCSLSEAMMQNLQ
151  SVMRPPGLPKSKSNAWVTEGMYAFCYRVMF
181  EAGYLTLFGRDISKTDTQKALILNNLDNEK
211  QFDQVFPALVAGLPIHLFKTAHKAREKLAE
241  GLKHKNLCVRDQVSELIRLRMFLNDTLSTF
271  DDMEKAKTHLAILWASQANTIPATFWSLFQ
301  MIRSPEAMKAASEEVSGALQSAGQELSSGG
331  SAIYLDQVQLNDLPVLDSIKEALRLSSAS
361  LNIRTAKEDFTLHLEDGSYNIRKDDMIALY
391  PQLMHLDPEIYPDPLTFKYDRYLDESGKAK
421  TTFYSNGNKLKCFYMPFGSGATICPGRLFA
451  VQEIKQFLILMLSCFEEFVESQVKCPPLD
481  QSRAGLGILPPLHDIEFFKYKLKH*
```

FIG. 7C

MOLECULAR-WEIGHT 57444    #LENGTH 505

```
  1 MMTISLIWGIAMVVCCCIWVIFDRRRRKAG
 31 EPPLENGLIPYLGCALKFGSNPLEFLRANQ
 61 RKHGHVFTCKLMGKYVHFITNSLSYHKVLC
 91 HGKYFDWKKFHYTTSAKAFGHRSIDPNDGN
121 TTENINNTFTKTLQGDALHSLSEAMMQNLQ
151 FVLRPPDLPKSKSDAWVTEGMYAFCYRVMF
181 EAGYLTLFGRDTSKPDTQRVLILNNLNSEK
211 QFDQVFPALVAGLPIHLFKAAHKAREQLAE
241 GLKHENLSVRDQVSELIRLRMFLNDTLSTF
271 DDMEKAKTHLAILWASQANTIPATFWSLFQ
301 MIRSPDALRAASEEVNGALQSAGQKLSSEG
331 NAIYLDQIQLNNLPVLDSIIKEALRLSSAS
361 LNIRTAKEDFTLHLEDGSYNIRKDDIIALY
391 PQLMHLDPAIYPDPLTFKYDRYLDENKKAK
421 TSFYSNGNKLKYFYMPEGSGATICPGRLFA
451 VQEIKQFLIMLSYFELEVESHVKCPPLD
481 QSRAGLGILPPLNDIEFKYKLKHL*
```

FIG. 8A

```
   1 GAGCTCTACC CTTGCTCTGC TATTTGTACT TTTAATACA CAGTTCAATC AAATGTGCCA
  61 CCAGAAATAT GCATGCTAAC AGCTGTAGT GGTTTGATTT TTCTTTCTAC TCTTCTGTGT
 121 GTAAGACCCC ATGTTTTATC AATTATTTT TAATGATTTC TTTCTTCATG CCATATGTGT
 181 GGCCGTCAGT GTGCACAGTC TGTGTGTACA GCAGGTGTCA CAGGTATCCA CAGAGGTTCC
 241 AGAGGTTCCC TGTAACTAGA ATTACAGGCA CTTGTAACTT TCCTGTATGG GTGCTGGGAA
 301 GCAATCTGAG GTCTCTGCAA GGGATCTTAA CCTCAGACTT TCTAGCCTGC TTTGCCCATT
 361 TCTATTTATG ATGACTGGAA ACTGGGCTTA GGCCCTTATAT TCTCTGAGGC CAAAATCAAG
 421 TTCTTCCAAA CTGCAGGATT TATGGTCTTC TATAGTATCC CACAGAAATG GAAAAGAAAG
 481 TGACCCATTA GAGCAGTATT AGAGTCGAAA TAAACTCAAC TTGGTATGCC AGGACTTTGG
 541 ACAATAATAA CCCTGTCTTT TCAGGGCATC TTATCTGTAC TGCTGCAATA GAAACTCCAC
 601 AGGTCAGGGT CACAGCTGTT GTGTTTTACA AGCTGTCCCC AGGATTAGTT CAGTGCCCAC
 661 CATGCAATAG GTGTCATGGT GTGTGTGTGT GTGTGTGTGC GTGTGTCGTG CTTGTGTGCA
 721 TGTGTGTGAG ACACACACAC AGAGAGATAC AAAGACAGAA ACAGAAAATT AATAAAAATT
 781 TTACCAACTA AAATAGGGAA TTAAAGAAAA GGAGGAGAAA AAGTTGGGCA TTCAACACCA
 841 TAAAGTCCCA GTACTATGCT AAGAACACCC AGCTGTCCTC ACACCCGGGC ATGAAACTTC
 901 ATGCACTGTT CATCAGAAAA TCGTTTACAC ACATCCCCTT GCAGTCTACT TGTAGTTTTA
 961 ACAACTTCAG AGAGCACTAG CATTTCCAGC CCCAGGGTTA GAAGCTTTGG TAGATGCTGT
1021 TTGCGAGCAC AGGATAGCAG CAAGAAGTGG ACTTGTTAGA AGGGAAAAGC CAATGCCTAT
1081 GTAACAACGA AAACTAAGTA TGAATCTCGA ATCATCCACT CTCGTGTGTC TGTGTCTCCA
1141 TATACGTGCT TGGGTGCCTG ACATGGCAAG GTGTTACAAG TAAGGGAGGA ACAAGAAAAG
```

FIG. 8B

```
1201 GACAGGGTAG TGGACATCAG GATGAATGCC AGCCAGGGCG ACTGGAGAGA GTCTACGCTG
1261 CTCTGAAGGT GGGTGAAGAA GACCTCAGGA AGCTTTCTGA GGCTCCGAGA GTGCTTTTCC
1321 CTTCCCATGT TGAAACATCC TTATTGCAAG AGAATTCCAG GTTCATGGGA ATTTGTAAAG
1381 AGAATACTAA GAGGCCACCT CGTGTCTCC TATTTTTGTC TGCTGTCATT TATGGGACAG
1441 GGTTAGAGAC CTGGCTTGCT TGGCTATGAG GCTGTTGCTT CCTCGGTTAC TCTGCTGTGG
1501 TTGGATGCAT TAGGGTTAGG CCCCTCAAGA GCCATGTGTC ATTTTATAAA AGCAATATAA
1561 ATATACTTAA GGTGCACAAA GCATTAGGAG GTCTGAGATA ATAGATTCTG AGAAAATCTA
1621 TCCTGCTGTG TAGCAACTGA TGTTTATGAT TATAGTCCCA GACCACACGA TAAAGGATCT
1681 GTGGCTCTG TTTAGGGAGG TCAAAAAACT ATTGCAAATG GAGTCTATAG AGAAAACTAG
1741 ACAGGACTCA ATGCTCACCA ATCGAGAATT AGTTGATGAG CTGGGTAGT GACTTAGTGG
1801 ATAAGAACAC GGTCCTTTCA GAGGTCCTGA GTTAAATCCC CAGCAAACAC ATGGTGGCTC
1861 ATAACCATCT ATATTGTGAT TTGATGCCCT CTTCTGGCAT GCAGGTGTAC ATGCAGACTC
1921 GTATACATAA AATAAATAAA TCTTGAAAAA ATGAATACGT TGAATAAGTG TCCCCTCGGA
1981 TAACTTTCTG CAGAATTTTA AGCACATGTC AATGGTAATA ACACACACAC ACACACACAC
2041 ACACACACAC ACACACACAC ACATACACAG TATGTATCTA GAGACATACA
2101 CATGTACATT TTATCTCTTC TATTTTCTTC TCCCCTCTTT GACATCAAGG AATAGAATGC
2161 ACTCACTGTG GCCTAGTGCC ACACTCTACC TATTTCTTTG GCTTTACTTT GTGCTAGGTG
2221 ACCCGAAAGG GTTTAAATAT CAAAAATGCT AATGGCTCGA CATTACATC CCCAATTCT
2281 CCTTTCTCCT TACCTCAGAC TCTTACATTC AGTTGACAAT TTGACATCGT CTCCTGGATT
2341 TTCAAATGTT CAGCACACTG TACTGATGTA CTGCCTTCCA AGGCAACCGG CACGATCCTC
```

FIG. 8C

```
2401 TCCCCACTCC CAAGCATCCC TCCATGAGCC AGTGTTTGCT TATCTTCTTG ACTCTCTGTTT
2461 TAACCCAACT CCTCCCCTAT TCACTCTGCT CTAATTCATT CATTCTATAT TTTCGCACAT
2521 CAGGCTCATC CTTTGCTCAG GAACTTCACT TTTGCTTTCC GGTCTCCTGG AAATGTGTTT
2581 TCCTATCAAC ATATTTAAAG CCCTCTTCAT CCCCAGTAGC TCTGGACACC TCATTTTATG
2641 GATACACAAC ACATATTTGC CACCTGTCTC CCCATTAAAA TATAATCTTC AGTAGAGAAA
2701 CTCCATATCT TGTTAATACC TGAAACAAGA ATATCTTCAA AGAGTTCCTG GGACATAAAA
2761 ACGCTCAATT AATATTTATG TTAAACAGGG ATCTGGGGTA TATCACAGAG GTAGAGGGCT
2821 TACCTAGGAG GAGTTGGGCC ATGGGTTCAA CTTCCAGCAC AGAATGAAAG ATTATGTTAA
2881 ATAAAGTTGG GAAGGATGTA TGCCAGTCTA TGAGTAGTAT AGGAGGTAAA TTATGAATTC
2941 ATATTTACTT TTCGACAAG AAGTGTTGTA GTCTTTATTT GAAATAAAAT ACATCTTAAT
3001 TACCAATAAC AATTGGTAAG GAGTGAATTC TCAAGCTGTG GCTTCCTGGT AGATGAGTCC
3061 TGGGAGGTTT TCTATTTCGA TGATGGTAGA TAGGTAACCT GTCATATACC ACAGTTCGCG
3121 CCTGTGGCTT TGTAAACACA CCGAGCAGTC AAGCAGGAGA ATAGTTCCAT ACAGTTCGCG
3181 TCCCTTAGGA TTGGTTTCGG GATACTTCTG GAGGTTCATT TAAATAATTT TCCCCGAAGT
3241 ACATTATGGG CAGCCAGTGT TGTGATGGGA AGCTTCTGCC TGTTTTGCTT TGCGTCGTGC
3301 TCCACACCTT TGACAGATGT GCTCTCATCT GTTTACTTCT TTTCTACAC ACAGAGCACA
3361 GCATTAGCTG CTGTCCCGGC TTTGGATGTT AGTCAGCAGC ATGAGGGACA GACCTTCAGC
3421 TTATCGAGTA TTGCAGCTCT CTGTTTGTTC TGGAGCCTCT TCTGAGACTA TGGACTTAGT
```

FIG. 8D

```
3481 TCAAGGCCGG GTAATGCTAT TTTTTCTTC TTTTTTCTAG TAGGAGGACA AATAGTGTTT
3541 GCTTGGTCA  CTCAAGTTCA AGTTATTGA  TCATGGTCCT GTGCACATAT AAAGTCTAGT
3601 CAGACCCACT GTTTCGGGAC AGCCCTTGCTT TGCTAGGCAA AGAGTCTCCC CTTGGAAAT
3661 TTTCCTGCTT TTGCAAAATG ATGACTATTT CTTTGATTTG GGGAATTGCC GTGTTGGTGA
3721 GCTGTTGCAT ATGGTTTATT GTTGGAATAA GGAGAAGTA  TGGAAAGATT TTTAAAAATT
3781 TGTCTTTTAG CTTATTTCTA GTATTCATTG CCTTCACTAT TATGTAGTGC AAAAAATACT
3841 AATGCATTAA TATTTTAAA  TTTAAATTT  AAAGACGTAC TTCTTTGACT AAATCTAGTA
3901 AGATGTAGAG AGTCCCCCTT GGAACATTCA CATATGCCAC TGGTAATGCA GATCTTGTGA
3961 AATATAACTA AAGAAATCAC AAGTCATCGA TGTAAGTTTG TGTCTGCATG GGCGGAACAA
4021 ACCTAAGCTA AGAAGAGTAG TATTGGGAG  GGATCTTTCT GTGACATGAA CTGAATAGAC
4081 GCACTGCCTC AGCAAACACA CATTCATTTG AATTTTCCCTC AGACTCAGTC TAAGCCTGGT
4141 GAGAGCACCA AGTGTGAGTC TGTCTGCCAC TAACGTTTCC TTCCAGTGGT AATCAGCTGT
4201 GTGGCTGTGA AACCTTGGCG CCTGCACATG ACAGCCATTT GAATAGTTCA AAGAACATTT
4261 AGGGACAGGA TATTAAGATA TTTTCTGTGA TGTCAACATC AAAATAGGAG AATGCCCCTG
4321 GCATTATCTT CAGAGAGGTA GACTACTGTG CGTTGTCTTA CTTTAAAGAA ATTTCTTTGC
4381 CCCTTTGGCT ATTTAATTC  AAACCTGAAA GTTTTCAGTT TTAATTAAAC TGTTGATTTT
4441 CATGCTAGGA AAGGAAATAT CAATTATACT TACAAGAAAT AAAATCATTT
4501 ATGTCGGGAG ATAAATAAGC TCATAATTTT AATAAAACAT TTAAGAGAGA GAAAAAGAGT
4561 AGTGGATTAT AGTTCATTGT CGTGTCAATGT TTACCTGACC CAGTTTCATT TTATAATTAT
4621 CTAATTTTTC AAATGAGATT CCTGTTCTTT CCAAATATCA TTGCAGAATA CTAACATTCT
```

FIG. 8E

```
4681 TTTTTCAGA GTTGAGAATC AAATGGAGGG TTTTTTCATC CTGGCACAAG CTCCGCTCTT
4741 CAGTAACACC TCCAGCCCTC AGAATGCCAA TATTTTAAAT TATGTAGGTT GTTAAAACTT
4801 TAGTGCTGGG GCTGGGGATT TAGCTCAGTG GTAGAGCACT TGCCTAGCAA GCGCAAGGCC
4861 CTGGGTTCGG TCCCCAGCTC TGAAAAAAAG AAAAAGAAAA AAAAAAACTT TAGTGCTGTA
4921 GCCCTTCTG TTATTGATG TTTCACATCT AAAACAAAAC AAAAAAAACA
4981 AGCAAATGGA ACATTTAGG CATTCTTTGG GTTAAAAAAC TCTTAGAGCA AGTCTAATCA
5041 TTAGGTGATA GTTTCATTTT TACACCAAGA ACAAGAAATCT TGTTGGCTGT GTTAACACTT
5101 TAAGCCCTGT TGTAGGGAAA AAGCAATCAG ACACAGGCAC AGAAAAGAAT TTGGATGAGT
5161 ACTTGATGAT GTATGTATAT ATGGTGAATA GACTGATGGG TGGGCTGCTG GCTGGGTTGG
5221 TAAGTGGGTA GATTTTTTT TAAAGATTTA TTCATTTATT ATATATCAGT ACACTGTAGC
5281 TATCTTCAGA TACACCAGAA GGGCATCGGA TCTCTTTACA GATGGTTGTG AGCCACCATG
5341 TTTTCCTAAC CTCTCAAGTC TCTGTCTTCC AGAAAGCTG GTGAACCTCC TTTGGAGAAC
5401 GGGTTGATTC CGTACCTGGG CTGTGCTCTG AAATTTGGAT CTAATCCCTCT TGAGTTCCTA
5461 AGAGCTAATC AAAGGAAGCA TGGTCACGTT TTTACCTGCA AACTGATGGG GAAATATGTC
5521 CATTTCATCA CAAACTCCCT GTCATACCAC AAAGTCTTAT GTCATGGAAA ATATTTTGAC
5581 TGGAAAAAAT TTCATTACAC TACTTCTGCG AAGTAATTA ATTCGTTATA CAGATTCTGT
5641 TTGTTCCTG GTCTGTTGAT GTATTAGTGT ATTTAGTTGT TCCAATTTTG TTAGGTTGCA
5701 GAATAGAGGT AACATAAAAT CAGGGCGTTT CTTAGTAATA AGCATTAGAC ATTAAGGCA
5761 GATGTAAACC GATTCCGGAG GATTCCGGAA ACAGAGGACA CTGCAGGAAT CAGGAAGGTA
5821 CAGATTCATA GCACCACTCG TCCCTTAACA ACACCCTGAG CAGGGTGTTG GCACTCTTAG
```

FIG. 8F

```
5881 CCTTCAGTCC TTGTACACAC GTTTCATTCC TAAGATATAG GCTGTATATT TAAACACGAT
5941 TTGGAAGCCA TCAAGAATCT GTTCTAGAGA AAACAGCATT TAATGATCTT TTGCAAGAAA
6001 ATATCAGTTA TAGTCTCTGT CATTAAGTAC ATTGTAATCT GGTTAAAGAG TATCTACTAA
6061 GAAAGTAAAG GCAGATTAGA ACAATACCAA TGGATGATGG GCCATCCAGA GAAATCCTAC
6121 TGTAAATGCT GGGATTTAAA CTTGACCCCA AGGAAGAGTA TGACTTGATT CTACCTTTGG
6181 AATGTGCTGT AAAATCATAT TAGGGAAGGT TCCAGACAGA GAAGTGGGAT GTATTTAATC
6241 TATCTTCCAG CCCACTCTCT AACACTAGCT AGCTTTGGGC TTTAGACCCT CCCCATTTCA
6301 TGGATTCTAT TTTCTACCAG GCATTGGAC ACAGAAGCAT TGACCCAAAT GATGAAATA
6361 CCACGAAAA TATAAACAAC ACTTTTACCA AAACCCTCCA GGGAGATGCT CTGTGTTCAC
6421 TTTCTGAAGC CATGATGCAA AACCTCCAAT CTGTCATGAG ACCTCCCTGC CTTCCTAAAT
6481 CAAAGAGCAA TGCCTGGGTC TGGCAAGGGA TGTATGCCTT CTGTTACCGA GTGATGTTTG
6541 AAGCCGGCTA TCTAACACTG TTTGGCAGAG ATATTTCAAA GACAGACACA CAAAAAGCAC
6601 TTATTCTAAA CAACCTTGAC AACTTCAAAC AATTTGACCA AGTCTTTCCG GCACTGGTGG
6661 CAGGCCTTCC TATTCACTTG TTCAAGACCG CACATAAAGC TCGGGAAAAG CTGGCTGAGG
6721 GATTGAAGCA CAAGAACCTG TGTGTGAGGG ACCAGTCTC TGAACTGATC CGTCTACGTA
6781 TGTTTCTCAA TGACACGCTC TCCACCTTTG ACGACATGGA GAAGGCCAAG ACGCACCTCG
6841 CTATCCCTCTG GGCATCTCAA GCAAACACCA TTCCTGCAAC CTTTGGAGC TTATTCAAA
6901 TGATCAGTA ACTTTCCAGT GCATTTAAA CTCAAAACCC AAAAAGACTT
```

FIG. 8G

```
6961 ATAGAGCTTT CTGTGCTATC AACAAAGAAA GTAATACTCA ATGTCCGTGT TTAGCATGTG
7021 CGTAACAGAA GCAGCAATTT TTAGGTGCAC AGTCCCATCG AAAGGGATGT CCCAGAAGCC
7081 ACAGAACTCA GACAGGTTGG TGCTCCATTA GTACAGGTTC CCTGGCCTAG TCTTGCTCCT
7141 CACCCGATAT GTTCCTCTTA ATATCAAATT AAATCCCCGA GTGCAGTCGT CACCACCATA
7201 TAAACATTTG AAATGATGAC TGACTTGCAG GTGTGATAAG AGCAGTGACC ATACCTTACT
7261 AATTCACTGG AATTCATAGG CAAAGTAACA CCATCGATTT TGTATTCATA TAGGAGCTGC
7321 AGCCATATTT TAAATAGCAC AACTACTTGT TAGTCAAGCA TTCTGAGGCT CACTGTAATC
7381 AGGTAAAGTA GGTTAACTC AGCGTCCCTAC CAGTTCCAGG CATTGAAATG GAATATCCTT
7441 TATCCCACCC ATTCAAAACG TAATATATAA ATGGAAGGCA CAGTTTTGAA GGCCATGGTA
7501 TGATTTAGGG AATTTACTCT CATGGTCCAA TCCCTTGTAA TTGTATGCTA GGTGACATAT
7561 CCTTCTGACT TACTATGTTC ATCGTATATT CAATCCTTAG TTTATAGAGA CTGACCAAAG
7621 CTCTGCTTTT GCATAGCAAA GCTCCTTTTA ATGCCCATTC CTAAACTCAA GGACACGAAT
7681 CCAGTTCAGT GCCCTTTTGC ATACTCCCTG GCAGACTCCC GTTGCCATAC ATCCTCCCTC
7741 GCTCGATTCC CATGACCTCG CCCTTGCACA CCCTGGTACT AGGACCTCTC CTGGCGATAC
7801 TTCCTACTAC CTATGCCACC TCATTAAAAG GAAGGGATAA TTGCTATTTA CTTGCAGTTC
7861 TCTGAATGAG GACATTTCC CCATACGGCT CTTTCCACAG GAGTCCTGAA GCAATGAAAG
7921 CAGCCTCTGA AGAAGTGAGT GGAGCTTTAC AGAGTGCTGG CCAAGAGCTC]
```

FIG. 9A

```
1     TTTTTGGTTA  TCTTTTCAGC  CGTGCCCCAC  TCTACTGGTA  CCAGTTTACT  GTATTAGTCG
61    ATTTCATGC   TGCTGATAAA  GACATACCTG  AAACTGGACA  ATTTACAAAA  GAAAGAGGTT
121   TATTGGACTT  ACAATTCTAC  ATCACTTGGG  ATCATGATGG  AAGGAGAAAG
181   GCACATCTCA  CATGGCAGCA  GACAAGAAAA  GAGCTTGTGC  AGGGAAACTC  CTCTTTTAA
241   AACCATCAGA  TCTCATGAAA  TTTATTCATT  ATCATGACAA  TAGCACAGGA  AAGAACTGCA
301   CCCATAATTC  AGTCACCTCC  TACCAGGTTC  CTCCCACAAAC ACGTGAGAAT  TCAAGATGAG
361   ATTTGGATGG  GGACACAGCC  AAACCATGTC  ACACTACCAT  GCCTGACTTC  CTTTCCATTT
421   TTGTATATTT  GCTGTGTTCTT CATTTGCCCG  AGAAGTAACT  CTAAAGGGCT  GTATTATTTG
481   GATATTAGAT  TGGCATTTA   TCTGACTGGG  ATATCTTGCT  GTGATTGTCC  ATGTATAAGA
541   TCAGCTTTTC  TATAAGCCAT  ATTTTAAAA   AGATATATTA  ATTTTTTAAA  AATCCACCTG
601   TCTAAATAAA  TGCACAAAGC  CCCCAAAAA   CCTAGATTCT  AAGAAAAATC  TATGTACTGC
661   CATACAATGA  TTGATATTAA  TATTTATGGT  GATAAATTAC  ACACAAAAAA  TGTGTGATCT
721   CTGTTTAAAC  AGGCAAAAAC  AAAAAACACA  TGAAATAAAT  CTATGGCATC  TATAGCCAAA
781   ACTGGAAACA  ACCCACATAT  CCATCAATAG  GAAATCAGTT  AAATAAATTA  TAGTACATTT
841   ATCCAATGGA  AGATTAAGCA  CATATTCAAT  ATAATTATTT  ATACACACAT  ATAGATACAC
901   ACATGTATAA  ATATAGAGAA  TACTGTGGGT  GTATGTGTGT  GTGTGTTTAT  ATACATATAT
961   ATACACACAC  AGTACTGTTG  CCTACCTTCT  TTTGTCTTAA  TTCTGTGAAC  TCTCATTCAC
1021  TCTGCTTCAG  TAGGATACCT  CCTTCTTTTT  GGTTCTTAGA  CTCACCAAGT  TGATCCTTGA
1081  CTCAAGACAT  TGCATTTGCT  GCTTCCTCTT  CCTGGAATAT  CCTTCCTTCT  GATATTCACA
1141  TGAGTAGTCT  CTTCTTGTCA  TTCAGATCTC  AAATGTCACA  ATTTCAGAGA  GCCCATCTCT
```

FIG. 9B

```
1201 GATCATCATA TCTAAAGTTG TCCTCATTCC CCCATAGCTT TCTATACCAT GTTTATTTT
1261 TTTCATAACA TGTATTTAT TACTCCTTTC TCCATTGGAA TAGAATCTCC ATTAGATTAG
1321 GAAATCTGCC TATCTTATTA ATGCCCTGCAA CTGGAATACT TTTGAAGAGT TCTGGCACG
1381 TAATAAATAC TCAACTAATA TTTTGTGTA CACAGAAATA AAGTTTGGAA GAACAGATGC
1441 CAAATTGTTA CTAGTGGTTA CTTCTGAGTA AAGGAGTAGC ATGGTAGGTA AATTATTAAT
1501 AGATGTTCAC TTTCCACCAA GATATGTTTT AGTTAGTCTT AACTTACTTG AAATGAAATT
1561 TATTACTTTA ATAATTAGAA ACATTGATAA ACATTTTAGT CACAAGAAATG ATAGATAAAA
1621 TTTTGATGCT TCCAATAAGT TATATTTATC TAGAGGATGC ACTTATGTAG AATACTCTCT
1681 TGAGGATGTT AGGTGAGTAA CATGTTACTA TATGTAGTAA AATATCTATG ATTTTATAAA
1741 AGCACTGAAA CATGAAGCAG CAGAAATGTT TTTCCCAGTT CTCTTTCCTC TGAACTTGAT
1801 CACCGTCTCT CTGGCAAAGC ACCTAAATTA ATTCTTCTTT AAAAGTTAAC AAGACCAAAT
1861 TATAAGCTTG ATGAATAACT CATTCTTATC TTTCTTCTTT TGATTATAGT TTATGTATTT
1921 ATTAGCTATG CCCATCTTAA ACAGGTTTAT TTGTTCTTTT TACACATACC AAACTCTTAA
1981 TATTAGCTGT TGTCCCCAGG TCCGAATGTT AAGTCAACAT ATATTTGAGA GACCTTCAAC
2041 TTATCAAGTA TTGCAGGTCT CTGATTGCTT TGGAACCACT TCTGATACCT GTGGACTTAG
2101 TTCAAGGCCA GTTACTACCA CTTTTTTTTT TCTAATAGAA TGAACAAATG GCTAATTGTT
2161 TGCTTTGTCA ACCAAGCTCA AGTTAATGGA TCTGGATACT ATGTATATAA AAAGCCTAGC
2221 TTGAGTCTCT TTTCAGTGGC ATCCTTCCCT TTCTAATCAG AGATTTTCTT CCTCAGAGAT
2281 TTTGGCCTAG ATTTGCAAAA TGATGACCAC ATCTTTGATT TGGGGATTG CTATAGCAGC
2341 ATGCTGTTGT CTATGGCTTA TTCTTGGAAT TAGGAGAAGG TAAGTAATGT TTTATCTTTA
```

FIG. 9C

```
2401 AATTGCTCTT TGATTCATCC ATTTAATTTT TTTACCTTCA TTTTTATACA GTAAATTTGG
2461 TTTCTATATAC TTACACATAT TAGCATTATC TTCCTTATGT TTTAAATGAA AAATTTGATT
2521 TGAATTTTA AAGTAATATC TTTTTACTA TATCTCACAA GACATATGAC AGCTTCCCTT
2581 TTTAGTATTG GCATATACCG ATGGTAATAT ATAAATGTAT ATTGGTGTTA AACATAACTG
2641 ACAGAAATG TATAAGGTCT CTATGTACAT TTATATGTGT ATCTAAAGAG GAAGCCCAGA
2701 TTAGTAAGGA TACAAGTAGC AAGTGGGAAT CTACAATGGA AAGGATTGCT TTCTCTCACA
2761 TGGCTTCAAT AGATACTCTT GCTTAAATAA ATGTTCTCTT TTAAGCTCAT TCTGTGCAT
2821 CGCATAGACT CAGCCCTAAGC CTGAACAAGA GCATAGAGCC TGAGCTGATC ATTCTATTAC
2881 TGTTTTAAA TAAATGTTAA TCAACTGTGG TGAATTGGGA AAGTTTGCTG AGTGTATGTG
2941 ACATCGATTT CATTTATTTA CAACTGGTTC AAGAATGCAA GAAAAACAAA TACAGTCAGA
3001 TCCAGAACCA TAGTTTATTT AACTTCTAAT TGGCTCAAGG AGTAATTGTG GGGAGCATA
3061 TAGATATTCT CTGCTATGTC AATCTCAAAA AGAGAAAATA ACCCTAACCA TCTTTCAGCT
3121 TTGTAGATTG CTATGTGTTT TCTGCCCTTTG CAGTTTCTTT CAGGCCTGAT AGTTTTTACT
3181 TTTAATTAAA CTACTTATCT TCAAACTAAG AAAAGAAAAGG TAATTACTTT ATACTGTATT
3241 ATTCTATCAA GAGGTACAGA AGTTTATGTT GGAAAATAAG TTTACATGTT CTAATAAAAA
3301 CATTTTAAAG GAGCACTGAA TTACAATAGA TGATTCCGTC AGTGTTTATC TTACTCAATT
3361 TCATTTATA ATAAGCTGAT TTCTCACATG AGATTCTTCT TCTCTGAAAAC CATCCTTATA
3421 GAATATAATA TAGATATCTT TAAACTAGGA ATATTTTCAA AACCTCAGTT CTGAAATCCT
```

FIG. 9D

```
3481 CCCTTATTCA GTGATCTGTG TCTTTAAAGA AAATAATCAA AAGAAACATT TTGAGATATT
3541 TAGAAAAATG ATGCTTAGCA AAGTGATAAA CACTAGAATG TAGTTTTGTT TCCGCACTGA
3601 CAACAAGAAT CTTGTTGGTC TTGTAAATCC TTTTGCCTGT ATCACTGGGA AAAGTGATGA
3661 GCACATAGTA GACGGGTGCT TGTTGAATGT GTATATGGAC GGATGCATGA ATGGATGGAT
3721 TTAGTAATCC TTTCCACCAA CATATCATGT TACTAGGTTA ATATAACCTA TTACTGTAGT
3781 AAAAGAGCAG GGCCCATCCA ACAAAAGAAA TATCTATAAA CTATAGGGTT TCAAAGTTTG
3841 AAGTCAGTGG GAAAATTTT AAAACCTGAT GTAAGTAAAA ACCCAAAACT GTAATCATCC
3901 ATGTCTATCA TACACTTGTG TCTGACAGGC AAACGGGTGA ACCACCTCTA GAGAATGGAT
3961 TAATTCCATA CCTGGGCTGT GCTCTGCAAT TTGGTGCCAA TCCCTCTTGAG TTCCTCAGAG
4021 CAAATCAAAG GAAACATGGT CATGTTTTTA CCTGCAAACT AATGGAAAAA TATGTCCATT
4081 TCATCACAAA TCCCTTGTCA TACCATAAGG TGTTGTGCCA CGGAAAATAT TTTGATTGGA
4141 AAAAATTCA CTTGCTTGCTACT TCTGCGAAGG TAAGCAGTTT TACATTTATA TACCATTCTG
4201 TTTGTCTTCT ACCTTTTAT GTGCTTGTCT ATTAGAAAT TTTGATGTAC TTAGATTTTA
4261 TGATAAAGGT GTTGAAGAGA GTTATCCTTA TGTGGAGATT CTTAGAAACA TAAATAAATT
4321 ATACGTAGCT TCTTAGTAAT AATCATTTAG AAAGTCAAAA TAGGTATAGA TTTCCGTCAT
4381 TTGCTTTGCA CGAGCTAATG AGGGTGAAAT ACAGATTAAA TGCTCTACTG AGACAGGTGG
4441 CACTGTACGA ATAAGATAGA TTAAAATTCA TCACATCAGC AATGTCTATG CAGAGCGAAG
4501 TGACGGAAAC CTAACATTCA GCAGTTGTCT CACCACACTT GTGCCACACA GTGTTTCATT
```

FIG. 9E

```
4561 TTGATAAGGA ATTGGCAAGA TATTTAACA TCATTTAGAT GTAATAAAAG AAGATCTGTT
4621 ACTGAGAAAA AAAACCAATA ACTACTTACT TACTGCAAAT AAATATTAGC TTTGGTCTTT
4681 GTGACTAAGT AGCTTAAAGT TTGGTTAAAA TACATCTACA GCTGGACACA ATGAACACA
4741 CCTGTAGTCC CTGCTATTTG AGAGGCTGAG GCAGGAGGAT CGCTTGAGTC CAGGAGTTTG
4801 AGGCTGCAGT GAGCTATCAT TGTGTCACTG CACTCCAGCC TGGGTGACAA TGTGAGACCC
4861 CATCTCTAAA AGAAAAAGAA AAAGAAATCT ACAAATAATA TAAAAGATAA CTAATGATTT
4921 TAAAACATTA TCAATTAGTT TATGTGCAAT AGCTGTAAAT AAGTGCAGTA GCATAAGAAA
4981 TAAGACATAG ATGACTTGAG TGATCCAGGG GAGTGCCACT GAAGTTGGCT TTAAAGGAAA
5041 GGTACAGTTT GGTCATTTAT TTGTAAAGTG CTATGAACTT GTACAAGGGA AAGCCAATTT
5101 CCCGTGTTTA CCAAGTAAGG AACTATGAAA GTATCTAATC CGTTTTTCAG TCATTTACTA
5161 TGACTAGGTC AGTTTAACT TCTTTTTCTG CATGTTTTAT TTGCTATCAG GCATTTGGGC
5221 ACAGAAGCAT TGACCCGATG GATGGAAATA CCACTGAAAA CATAAACGAC ACTTTCATCA
5281 AAACCCTGCA GGGCCATGCC TTGAATTCCC TCACGGAAAG CATGATGGAA AACCTCCAAC
5341 GTATCATGAG ACCTCCAGTC TCCTCTAACT CAAAGACCGC TGCCTGGGTG ACAGAAGGGA
5401 TGTATTCTTT CTGCTACCGA GTGATGTTTG AAGCTGGGTA TTTAACTATC TTTGGCAGAG
5461 ATCTTACAAG GCGGGACACA CAGAAAGCAC ATATTCTAAA CAATCTTGAC AACTTCAAGC
5521 AATTCGACAA AGTCTTT
```

FIG. 10A

```
   1 GAATTCTACT CTTAAAGGG GTGAATATTA TGGTACTTGA ATTTTATCTC AAGAAAAATG
  61 AATAAAAAGT AACTAAATCA TTGAAAATAT CTGATGGCAT GGGGTTTGTG GGGTAACTGG
 121 CATTCCACAG TGATTTTCAA AGGGCTTGTG CTGTTTTCAT TTTGCTTTGT TTTAGTTATG
 181 GAGCCCTTCC TTGAAACAAA CTTCATACTA CAGTCCTCTT TCATGAAGCA GAAGAGGGCA
 241 GTGGGCAGAG CTCTCCTTTG GCTTTCTCCC CCACCACAAC AGGGAGCCCT GGAGCTCTAG
 301 GAGAGAAAAT CTGAAATATA AAGGCATGC ATGTGAGCTG TGGAGTCCCA GAGCCCTGGG
 361 TTTGCATCCT AGATCTGCAA CTCCCGTGAA TTGAGTTTTG GGAAGTTGCT GAAACTCTGA
 421 CCTCCTGTTT TCTCATGGTA TTGTTGTAAG GGTTAAATGA GACAATGTAT GTGAAGACCC
 481 TGGCCCCACA GTAGAGGCTC TGCACACATT TCAGCGATAC TTTCCTCATG TATTTCCAAA
 541 AATGTTTCT CATTTTCTTA AAATGTCAGA AAGAAGACAA CAGAACTTAC TTGCCTTTTA
 601 CAACAGAACA AATGGAGCAA GTCAGAGGTC AAGGTGCTAA CATTCTTCAT GGTTCCTCAC
 661 CACCTTTTGT TCTGTTAGCC TATAGGGAAA AGTCTTCTTT CTCATCTCAT TATCTGCAGG
 721 GGAAATAGT ACTTCAGCAA GTGATCCAGT TGAAGAACAT CTCCAGGGCC ATTAACATAC
 781 AGAGGTTTGT TCTACTCTCT CTGTGCTCCA TGTCTAAGAA CCTCAGCCTT CCTCCTAGGA
 841 GCTAGGGAAA GTCAGGAAAG TGAAAATAGT ACCCCAGCTA ATGAACTGCC CTGTGCTGGC
 901 CTGAGAAGAC AAGACCAGCT TCCTCAATGG CTCAAGATTT GGTTTCCTTC AATATGTCCT
 961 TTTGGAAATA TGTCCATGAC ATCGGAGAGA TAAAAGGAGC CAGGATTGCT CACATTCAGG
1021 AAAAAAGCTC CACTATCTTT CTCTCTCTCC CTCTTTTCTCT CCCTCCCCCT GACTGCCCTC
1081 TTCTCTATCT CTCTCTCTCC CTGAGCTGGC AAGGTTAATT GGTCGCAGAA AGCCGAAGAA
1141 ACAAGTGGGC CTCCTGGAAC AAAGTTCAAA AAGCCGAAAA CGGGAAGAAA ACTAACCACA
1201 AAGTAAAAGG AACCACTTAG CCTTCTTTGA TTCCAGGCCC CCAAGCCTGT CTTTAACTTG
1261 GATGAATGGA GTTCTTCCTG TGCTACAGCA CCGCATAGTA GGGGCTGCCC TGGGCCTGAA
```

FIG. 10B

```
1321 GCCAGAGCTT CACCATATTC AGTCATCTGT ACATTGAGGC AACAGTGCCT GCTTCATGGT
1381 GCTACCCTGT GGATTAAATG AAGCAAGTTT TTGATGATCT TGACACTGAA TATTGATGCA
1441 TTGGTCAGAC TTTTCTGAT AGTAAAAAAT GGTGGTTTCT TGTTGTCAGA AATCAAATCA
1501 ATATATTGT TCTCCCTGTTG ATTAGCTATG TCCCCTAGAG GGCAGCGACT TTGCCTGTCT
1561 TATTTATCTC TGCATCTCCA GCACTTAAAA GGTGCCTTGC ATAAGGTACA TATTAAGTTC
1621 ATATGAATGA ATGAATGAAA TGCATATGAT TTATTCATAC CCAGTTGGTG GTGTGTTTAC
1681 CCTTTCCTAA ACCTGTAGTC AGATGGCCTT TGAATCCCCT GTACTTCTTG TGAGGTACTG
1741 TGCTGTAAAG GTGGACTATC ACACTTCAGT TCAGAGCAAT CTGGGCTTGA ATCCTGGATT
1801 TGCCAGTTTA TTAACTATAG CAAACATTTT TGAGCATACA TTGTGCCAAG TGCTAGGCTA
1861 ACTGTCTTAC ACACATTGTC TTATTCGTC TTAATATCTA TGAGTCATGC ACTATAATCA
1921 TCCCCATTTT ACAGATAAGA AAGCAAAGAC TTGGAGAGGA AAAGCATCTT GTTCAAAGGT
1981 AAATACTTAA TGGCCAAGCC AACATGCAAA TCTAGATTTA ATTGCAGCTT CCTCTTCATC
2041 TACCATTCGA ACTAATTCAA GCTATGTAAT ATTTCCCACT GAACCTTCTT GCCCTCTACTT
2101 CCTCATCTT AACATGGTCA AAATACCTGT CCTGCCCAAG TTAGTTATTT CATTAAAGTA
2161 GAAAAATACA AGAGAAGCTT TTAAAATGTG AAACCTCAAA TGAATGTAAA ATTATGATGA
2221 TTCCTTTAGA ATTTGTCAAC ACCTTCTTTT CTCTACTCCT GCTAGGCATT TACAATCTCA
2281 AAACCATGTA TTAAGATGC AAAACTATAT TTGTATTTGC CATAAACTGGT TTCTTTCCCT
2341 ATGGCTTCAT GAAAATGTGG CTCGAATGTG TTTATTATGA AAGCCCCAAA TTAATCACGA
2401 CAAGACTTCA CCAGCCCATT CCACAATAGA CTCCCCATTAC TTTGCCCTGA CTTAGAAACC
2461 TCATATACAG TCTTGATTCA GTACAGCTCT GTGATGCTCT TGGAAAATGC AAAGTGCTTT
2521 CTTAATTGAG GCAATCTGTG TCCCACTACA GAGAGGTGGT TTAACTTGTG AATTC
```

FIG. 11A

```
   1 AGAGCAACCT GGGCAACATA GCAAACCCT GTCTCTGCAA ACAATAAAAA GAAGAAAATT
  61 AGCTGGGTAT GGTGGCACAT GCTATAGTCG CAGCTACTCG AGAGGTTGAG GTGGGAGGAT
 121 CAGTTCAGCC TGGGAGGTTG AGGCTGCAGT GAGCCAGATC ATGCCACTGC ACTGCAGCAT
 181 GGGCAACAGA ATGAGACCCT GGCTAAAAGA AAACAAAATA AAAAATTCAG ACACAGGTTG
 241 AATCATTGAT AACAGCATAG TGGTAACAGA AAGAAAGTTT GGGAAATTT TATCTGATCA
 301 GCTTCCCATA CCCTGTTCAT CTTTGTGTTA TGCACTGCCA GGCTGTCTGT AGGTTCAGAC
 361 TCTATATCAT ATGACCTTCA AACACTTGGT TTGTTCTTCT CCTTCCTTCC TCCCTTCTTC
 421 TTTCATTTTT TATCTTTTT TGTTTAGATA GTATAATAAG GAACTGCTGA
 481 GGCTTTCCAG TGCCTCCCTC AACATCCGGA CAGCTAAGGA GGATTTCACT TTGCACCTTG
 541 AGGACGGTTC CTACAACATC CGAAAAGATG ACATCATAGC TCTTTACCCA CAGTTAATGC
 601 ACTTAGATCC AGAAATCTAC CCAGACCCTT TGGTAAAGTC GCAGTGTGCC CGAATTGAAA
 661 TTCAATATCC AGTGATAGC TACCTAGATC TAAATAAAGA GGAAATTTAC AATGGTAGAA
 721 TTGATTTCT CATAGTAGTC ACAGGAATTG TCTGACTTAA TTGTGTTAAA TATTCATATA
 781 TTTTGGAAAA TTTAGATAGT GGTCTGAATT TTTCATTTTA GTCCTGATAT TTGCCATCAC
 841 ACAGTCTTTG CTAGATTATA TTTGCAGTCA TGATAATAAA CCTGCCACTT TTTTTTTCTT
 901 AAAAAGCACC TCCTCCCAAA TCCAGGAAAT TGGAGGCTAA TATATTGATT ATTCTAGTTT
 961 CTTCTGGGAA CCCTTCTCTC TCTAGCTCTG CCTGACTAAG GAACTAATCG TTCAAGCAGG
1021 ATAGGAAGGT ATCACAAGGC TTCCTTAGCT CCTGTTCCTT ATTACTTTCT
1081 GATTCAATGT GGAGTATTTG CTAAATCACT AATGGGGTAG AATTAAAAAG AAAATTACTC
1141 TTTGGAGCTT CCAGGTTTAG AAAGAGATAA ATTTCTTTAA AACTAGCTTA AGGCGGGTTT
```

FIG. 11B

```
1201 TCTTGTATT TTTATTGCAG ACTTTAAAT ATGATAGGTA TCTTGATGAA AACGGAAGA
1261 CAAAGACTAC CTTCTATTGT AATGGACTCA AGTTAAAGTA TTACTACATG CCCTTGGAT
1321 CGGGAGCTAC AATATGTCCT GGAAGATTGT TCGCTATCCA CGAAATCAAG CAATTTTGA
1381 TTCTGATGCT TTCTTATTTT GAATTGGAGC TTATAGAGGG CCAAGCTAAA TGTCCACCTT
1441 TGGACCAGTC CCGGGCAGGC TTGGGCATTT TGCCGCCATT GAATGATATT GAATTAAAT
1501 ATAAATTCAA GCATTGTGA ATACATGGCT GGAATAAGAG GACACTAGAT ATTACAGGAC
1561 TGCAGAACAC CCTCACCACA CAGTCCCTTT GGACAAAATGC ATTTAGTGGT GGCACCACAC
1621 AGTCCCTTTG GACAAATGCA TTTAGTGGTG GTAGAAATGA TTCACCAGGT CCAATGTGT
1681 TCACCAGTGC TTGCTTGTGA AATCTAACA TTTTGGTGAC AGTTTCCAGA TGCTATCACA
1741 GACTCTGCTA GTGAAAAGAA CTAGTTTCTA GGAGCACAAT AATTTGTTTT CATTTGTATA
1801 AGTCCATGAA TGTTCATATA GCCAGGGATT GAAGTTTATT ATTTTCAAAG GAAAACACCT
1861 TTATTTATT TTTTTTCAAA ATGAAGATAC ACATTACAGC CAGGTGTGGT AGCAGGCACC
1921 TGTAGTCTTA GCTACTCGAG AGGCCAAAGA AGGAGGATGC TTGAGCCCAG GAGTTCAAGA
1981 CCAGCCTGGA CAGCCTTAGTG AGATCCCGTC TCCAAAGAAA AGATATGTAT TCTAATTGGC
2041 AGATTGTTTT TTCCTAAGGA AACTGCTTTA TTTTTATAAA ACTGCCTGAC AATTATGAAA
2101 AAATGTTCAA ATTCACGTTC TAGTGAAACT GCATTATTTG TTGACTAGAT GGTGGGGTTC
2161 TTCGGGTGTG ATCATATATC ATAAAGGATA TTTCAAATGT TATGATTAGT TATGTCTTTT
2221 AATAAAAAGG AAATATTTTT CAACTTCTTC TATATCCAAA ATTCAGGGCT TTAAACATGA
2281 TTATCTTGAT TTCCCAAAAA CACTAAAGGT GGTTTT
```

FIG. 12A

```
   1 GAATTCTAAA CACATATTAA TATCAATGAC TTATATGTAT GTATATATAT ATCTAATATA
  61 GATAAATGTAT CTAGGGATAT ATATATATGT ATATTTTATC TTTCTTCCTT TTATTCTTTC
 121 TTCTCCCCTC TCTGTTCAAC ACCGAGGAAT AGAATGCACT GTGGTGTCAT ACTCTGCTTA
 181 CTCAGCCTCT TATTGACCTC TGAGTCAATA CAGTGCTGAT GTACATCTCC AAATGCCCTC
 241 TTTTCTCCTA ACCACAGACT TTTACATTCA GTAATCAATT TGACATTGTC CCATGATTTA
 301 CAAATGTTCA CAATAGTATA TTGACCTATT GCTGCCTTCC AAGGTCCTCT CCCACTCCCA
 361 AACATCCCAA TATGAACCAG CTTTTGCCTA TCTTCTTGTC TCTTACTTTA ACTCAATGTC
 421 ATTCCCTATT CACTTGCTG. TAATAGATGC TACCTTGATT CTGGTTTTTA GCACCTTAAT
 481 TTCGCTCTCT GCTCAGGAAC TCTGCCTTTG TACCTTCCCTC TTCTGGAAAC GCTTTTCCTT
 541 TGCTGTTATA TCTCTTCAAA ACAGCTTCTC TATTCAATAT GCTCAAGCTG CCTTCAGCCC
 601 TCAACAGCTC TCCCTACCTC ATTCTAGTCC CTCCACTAGA ATAGAATCTT CATGAGAGTA
 661 GCGAACTTCC CTATCTTGCT AGTACCCAAA GGCAGAAAAA TCTTTAAAGA GTTCCTGGGA
 721 CATAGAAAAA GTGCTCAATT AATATTTGTA TTAAATAGGG ACCTCAGGTG TAACTCCGTG
 781 GTAGAGCGTT TGCCTTAGAG AAGTAGGGCC ATGGGTTCAA ATTCCAGCAC AGAACAAAAA
 841 ATTGTGCTGA ATAAAGTTTG GGAGGATGTG TAGCAGTTTA TAGTGCAAGT GGCATAAGCA
 901 GTAAATAATG AATTTGTATC CACTTTTCTA GCAAGAAGTA TTTTATTCTT TATTGAAGG
 961 ATAACAATTG GTAAAGACTG CATTCTCAAA ATAAACTATG GCTTATGGCT ACGTGGAAGA
1021 TGAGATAGGG AGAAGGTTTT TTTTTGATGA TGGCAAAATA ACATGTCATA GTCCACACGA
1081 AACACCTGTG AAGTTGTAAA CACACCTAGC AATCAAACAA GAAAATTGTC CCACCCTATT
1141 ATCATTCTTT TGGATTGCTT GTGGCATATT TCTGGAAAAT GATTTAAATT AATTCCTTCT
```

FIG. 12B

```
1201 AAAGTAACA ACACAAACAA CCACTATCAT GACGAAAAGC TTCTGCCTGT TTCAGTTTAC
1261 ATCATGCTCA ATGTCTACAA CAGACGTGCT CATCTTCAGA GTGTTACCT CTGCTTTTA
1321 CACACATTGA AGCACAATGT GAGCTGCTGT CCCTGGGTCT GAATGTTATG TCAGCACACA
1381 AGGGACAGAG CTTCGGCTTA TCAAGTATTG AAGCTCTCTG CTTGTTTTGG AGCCTCTCT
1441 GATACTATGG ACTTAGTTCA AGGCTGGGCA ATACTATTTT TTTCTTTTTT CTAATAGGAG
1501 GACAAATAGT TAGTTGTTTG CTTTGGTCAT CCAAGTTCAA GTTATTGGAT CATGGTCCTA
1561 TGTGTATAAA GAGTCTAGTT TGAGCCCTTTC AGGGGCAGCC TTGCTGGCTA AGCACAGACT
1621 CTCCCTCTGG GAGTTTTCCT GCTTTGCAAA ATGATGACCA TCTCTTTGAT TTGGGGATT
1681 GCTAGGGTAG TGTGCTGTTG TATATGGGTT ATCTTTGACA GAAGGAGAAG GTATGTCTTT
1741 TAGCTTATTT CTAGTGTTTT CACTATTATA CAGTTCCAAA AAAATACTAG TACATTAGTA
1801 TTTTATTTA AAATTTAAAG CCATGCTTCT TTGACTAAAC CTGACAAGAT GTAGAGTTTC
1861 CCTTTGAATA TCCACATACA CTGATGGTAA TGCTGATCTT GTTAAACATA ACTAAAAAAA
1921 TTATAAGTAT TGATGCATGT TTGTGTGCAC TTCTGTGGAG TACACCTAAG CTGGGAAGGG
1981 TGCATTTGGC AAGGGTGACG TTTGGAAAGG ATCTTTCTCT CACAATAACT GGTTATGCAT
2041 ATGCTCTTCT GGGTTCTCTG TTACATCAAC ATTAAAATAC AGGAATACCC TTGCATATC
2101 TTTGGCAAGG TAGACTGTGT CTGCTGTCTT AGTTTAATA ACTTCTTTGC CTTTGAGTT
2161 ATTTGAATTT ATGCCTGATC GTTCCAGTT TTAGTTGTCT TAATGCTAAG AAAGGACAAA
2221 TCAATTATAT TTAGTTATTC TAACAAGAGA TAACTAGTTT ACGTTGAAAA ATAAATTATC
2281 TTATAATTTC TAATAAAAAC ATTAAGAGA GTTAGAAATC AGCGAATTAT AGCTGATGAT
2341 CTGCCAATGT TTACCTCACT CAACTTCATT TTAGATACTT TTTCAAGTGG GATTCCTATT
```

FIG. 12C

```
2401 CTCTTCAAAT ATCCGCACAG AATTATAGTC CCCTTCTTTC AGAGTGGGGG GAATCAAATG
2461 AAAGGTTTCA TGTGTGCTAG GCAAGAGCAC CACCGTTGAG CCACACCTCC AGACCCCACA
2521 ATGCCAACAT TTTAAACTA TGTAGAGTTT AAAAAACTTT AGTTCTGTAG CCTTTTCTAT
2581 TAGCTGGTGT TTCATGTCTT CAAAGAAAAG GAAAACTGAA ACATTTAGA CATATGGACA
2641 AATGATTCCT TGAACAAGTC TAAGCACTGA TGATAGCTTC TTTTCTACAG TGAGATCAAG
2701 AATCTTGTTA GCCCTGTTGA TACTTGTAGC CCTGTCACTT GGAAAAGCAA TCAATTTTAT
2761 GATCTAGAAA ATAGAGCTTG CCTAAAGATC AGAGTGCAGA GCTAGTCACA CTAGTCAGCC
2821 ATACAGGTTA GGCAGTGGTG GCACATACCT TTAATCCCTG CAGCCACTCA AGTTACCCAT
2881 AGAAGCTGGG TGGTGGTGGT GCACACCCTT AATATAAGGT GGAGCACACT TTAATGTAAG
2941 GTGGGTAGAG TCAGGAGTGC AGTGTATTCA GTCTGCAGTC ACACTGAGAA CAATATCACC
3001 CCAGTCTTGT TAGAGGTAAG AACTCTCTAG TGATTGGCTG CTTTGCTCTT CTGATCTTCA
3061 GTTTGAACTT CTGTCTCTGG GTTTTTATTA TTCGTGCTGC AGACATAGAC ATAGCAAACA
3121 ATTTAATGAG TGATTGATGA ATGTAGATAT GTATGTACAT ATTGTGCTGG ATAGACTGTA
3181 GATGGGTTGG TGGATGGGTT GATGAGTGGG TAGATTTAGT AATCACCTTC ACCAATATCT
3241 TAGTAGGCTA AAAAGCCCAC TGTTTTAGTA AAAGAGTGGG GTATCCAACA AAGAAGTATC
3301 TATAAACTGT AGTTATGTGG TAGAAATAAG GGGTAGAAAC CAGTAAAAAT TCGGCTTATG
3361 TACAAATGCT AAACATGTAA TTTCCTAAAC CTCTCAATCT GTCTCACAGG AAAGCAGGTG
3421 AACCTCCTTT GGAGAATGGG TTGATTCCAT ACCTGGGCTG TGCTCTGAAA TTTGGCTCTA
```

FIG. 12D

```
3481  ATCCTCTTGA  GTTCCTGAGA  GCAAATCAAA  GAAAGCACGG  TCATGTTTTT  ACCTGCAAAT
3541  TAATGGGGAA  ATATGTTCAC  TTCATCACAA  ACTCCCTGTC  ATACCATAAG  GTGTTATGTC
3601  ATGAAAAATA  CTTTGATTGG  AAAAATTTC   ATTACACTAC  TTCTGCAAAG  GTAACTAGTT
3661  TTTACAGATT  TGCTTGTTT   ACTAGCCTGT  TTATTATTAG  GTTATTTAG   TTGTTCCAAT
3721  GTTATTAGAT  TGTAGGATAA  AGGAACATA   AAATCAGGAA  GTCTCTTGGT  ACTAAGCATT
3781  AAAAAGTCAA  GGTAAATGTG  AATTTGTGAT  TGATGATGAC  ATACACAAAT  TAAGCACTTT
3841  GTAAGTACTT  TCTGAGCCAG  AAGACACTAC  AGGAAGGCAC  AGACTCATAA  CATCCATGCT
3901  GCCATCTACA  CAACACTCAG  AGCACTCAA   TACCACATCA  TGCACACGAA  CTCGTTCGTT
3961  AAGAAGTCGA  CAGTATATTT  AAGCATCATT  CAGATGTTAT  CAAGAATCTC  TATTCTAGAG
4021  AAAACAACAC  TTAGCTGAAT  TTTTACAAGA  AAATATTAGA  CATGGTCTCT  GTCTTAAGTA
4081  GATTAAAGTC  TGGCTAAAGT  GCATCTGCAG  AGAACAAAAG  GTAAAGATAA  AATCAATGGC
4141  CCATTAGTCC  AGAGAAGCTT  ACCTGAAAAT  CTGGGATTA   AACTTGACCT  TAAAGGAAGA
4201  GTATGTCTTA  AGTTTGACTT  TGAAAAATGT  TATGAAATTG  TATTGGGAAG  GCTAGACAGA
4261  GAAGTATGAT  ATACTTTAAT  CCATCTTCCA  GCCATTCCT   AACACCCAGG  TTTAGCTGCT
4321  CCCCCTCGA   CGAATTTCAT  TTTCTACCAG  GCATTGGAC   ACAGAAGCAT  TGACCCAAAT
4381  GATGGAAATA  CCACAGAAAA  CATAAACAAC  ACTTTTACCA  AGACCCTCCA  GGGAGATGCT
4441  TTGCATTCAC  TCTCTGAAGC  CATGATGCAA  AACCTTCAAT  TTGTTCTGAG  GCCTCCTGAT
4501  CTTCCTAAAT  CAAAGAGTGA  TGCCTGGGTC  ACCGAAGGGA  TGTATGCCTT  CTGCTACCGA
4561  GTGATGTTTG  AAGCTGGATA  TCTAACTCTG  TTTGGCAGGG  ATACTTCAAA  GCCAGACACA
4621  CAAAGAGTGC  TTATCCCTGAA CAACCTTAAC  AGCTTCAAGC  AATTTGATCA  AGTCTTTCCG
```

FIG. 12E

```
4681  GCGTTGGTGG  CAGGCCTCCC  TATTCACTTG  TTCAAGGCGG  CACATAAGGC  CCGGAACAG
4741  CTGGCTGAGG  GCTTGAAGCA  TGAGAACCTC  TCTGTGAGGG  ACCAGGTCTC  GGAACTGATA
4801  CGTCTACGCA  TGTTTCTCAA  TGACACTCTC  TCTACCTTTG  ATGACATGGA  GAAGGCCAAG
4861  ACACACCTCG  CTATCCTCTG  GGCCTCTCAG  GCAAACACTA  TTCCTGCAAC  CTTCTGGAGC
4921  TTATTCAAA  TGATCAGGTG  GATAGCAATT  TGAGTGTTTA  TTCTTCATAG  TGACAGAAAT
4981  TAACAATTTT  TAATAAACCC  CCCAAAAGAC  TAGCAGAGCT  TTCTTTGCTG  TTGGTCAAGA
5041  ATGTGATACT  CAGTGCCTGT  GTTTGACATA  TATATATAAC  AAAAGTAGCA  TTTTGTAAGA
5101  ATATAGTCTC  ACCAGAAAGG  GATGTCCCAG  AAGCCGCAGA  ACTTAGATCT  GCTGGCACTT
5161  GTCATTAAAG  GTCCCCTTGC  CCAGTCTTGC  TTTTAACTCC  ATAGTGTTCT  TCTTAGTGTC
5221  AAGTAAATC  TATGACTGCA  GTCTTCATCA  CAACTTTAAA  TAATGACTGA  CTTGTCAATG
5281  TGGTAAGTGC  AGAGGCCACA  CCTTACTAGT  TTGAACATTC  CTGTTTTCTG  CGGCCCTCACA
5341  GATTACAGC  AGAGTTGCAA  CATCAATTTC  ATATTACCTA  TGAACTACAA  CCATATTTTA
5401  AGTTCAACAA  CTACTTGTTA  GTAACATTTC  TGAGGCTCAG  TTCACTTTAA  CCAGATAAAG
5461  GAGATTTCAA  ACAGCTGCCA  ACAAATTTCC  ATGCACTGAA  TGGAAGTATT  CTTTATCGCA
5521  CAGTTCAAAA  ATAATAAACAT  AAATATTCTG  AAGCTGTGGT  ATGAATTTAA  AGAGTAAATT
5581  TGAATTTCTA  CTTGGGAATT  CACCAATACC  CTGTAATTGT  ATGTTAGAGG  AAGTATTCGG
5641  AATGAATTAC  TCTACTCATC  ACACGAATGT  CTAGCCCTTA  TTAGAATCAT  TGGTTTATAG
5701  AGATCTGACC  AAAGCTTTGC  TTTTACATAG  CAACGCCCCT  TTAATGCTTC  TTCATAAATT
5761  CAAGGACATG  AATCCAGTTC  AGAATACAGT  ACAAGTAAAT  GACAATGCCC  TTTGCATGTT
5821  CCTGGAACCA  CTTCCCTTTT  CATGCTCCCA  TGCTAACGCG  ATCACCTCAT  TAAAAGAAAT
```

FIG. 12F

```
5881 GGAGTTCTTA TTTACTTGCA GCTCTCTGAA TAAGGCAATA TCTTCCATAT GTCTCTTTTC
5941 ATAGGAGTCC TGACGCATTG AGAGCAGCCT CTGAAGAAGT GAATGGAGCA TTACAGAGTG
6001 CTGGTCAAAA GCTCAGCTCT GAAGGGAATG CAATTATTT GGATCAAATA CAACTGAACA
6061 ACCTGCCAGT ACTAGGTGTG TTCCCTATGC TATCCCTCAC TAACATGTCA CTAGTAACAA
6121 TGCTCAACAT ATAATGAATG TACTATATTC TTGATATATT TGCAACGCTG CAACAGTCTA
6181 ATAACTAGGG TCATCTTCAT TTTTTCTAAC AAACAAGGAA CTGAGACCCA GAGCGTGGGA
6241 CAGTGGCAAC CCTGGCATAG AACATTTGAT ACTCAGTTGC TCTAGGTCCT TGGCCTCCTT
6301 TCTTAGTCCT CCAAAACCAC AAACCCAGGG TTAAGGAAGC ATGGAATTAA TGTGAACAAA
6361 GCAAACACCAT TGGTTTGGGC GATGAGACTG AGGCTTTTCT TCCTTTGTTT CTGTATTTC
6421 TAGAATGCAG TAGTACCATG TATTACAGTA AAACAGCCAT ATTTTGTGT CCTGTTCTGT
6481 AAAGGACAGA AGCCCCCATA TGCTTTGAGG GCAGTTTAGT TTATTAGAAG CAACAGAGCC
6541 TAGATTCAGC ACTGCCTGGT TTGGGACCTC CCTTTAGACA CCTCCCTTTT CTCACCTGTA
6601 AATAAAGGCT AAGTAAGCAT TTGTGACTGC ATACTCAGTC ATGGCCTGAA TCCTGGGAAC
6661 AAGGCAGCTA GCAGCTAGAG TTGTGACTGC AGGACTGGAC CTCAGCAGCT CTACTGCATT
6721 ACTTCCCCTA GAAGCAGGGT GTGGCTACAC AAAACCAGAC AGATAATGTA TGGCTGAATG
6781 TAGATTCATG AAATGCTTGG AAAGACATTT ACTTATCAGT ATGTTTAATT CCCAAAATGG
6841 TCAGCAACAA TTCACACAAA AGTTTTTTCA AGTTTTGCTTAG CTGTTTAGTG
6901 TCCAGTAGAA ATAAGATTAC TATTCTATAA AGTGACAGAT GTTCATCTAG TTCCCATTGA
```

FIG. 12G

```
6961  TGGTGAAGAA  CATTATGTCA  TCCCAAAAGA  TCGTTAACTT  AGATCGTGGT  TCTCTACCTT
7021  CCTGATGTTG  TGTGACCCCC  AACTGTGAAA  TTATTTTCAT  TGCTACTTCA  CAACTATAAT
7081  TTTGCTTCTG  TCATGAATCA  TAAAGCAAAT  ATCTGTGTTT  TCTGATGGTC  TTAGGTGACC
7141  CCTGTGAAAG  GGTCATTTGA  CTCTACCCCC  TACATGGGTT  GTGATCCACA  GGTTGAGAAG
7201  CACTGACTTA  GATTCTCAGA  TGCAAGTAG   AGCAGCAGAA  TTTCGAAGAA  CAGCAGTGGC
7261  GACAGAAGCT  GCTTTGGGCA  GTTGTCATTT  GTTAGCTTTC  ATTGGCTCAT  TTTGTATACA
7321  GATTTCGGA   AGTATTTCAG  ACTTTATGTT  ATGTAGCCTT  TAGAGGCAAC  AGTTCAGGAC
7381  TGGAGAGATG  GCTCAAGGGT  TAAGAGCACT  GGCTGTTTTT  TCAGAGGACC  CATGTTTGAC
7441  TCACAGCACA  CACATGGTGG  CTCACAGCCA  TCATGACTCC  TGTTCCAAAG  GATCTGATGT
7501  CTTCTCTGA   CCCTGCAGA   CACCAGGCAT  GCATACATGC  AGGCAAAATA  CCCATCAATA
7561  TAAAATAAA   TAACTGGGAA  ATATGCAAAT  TCTTTAATAT  GCAAATTCTT  CTCTCCCCAA
7621  CTGCCATTTC  CCATGCTCCA  CCCTCATCCC  TTCCCTCCTC  TCTTACTTCT  TTTGTTTGGA
7681  ATTCTTTAGA  TAGCATCATC  AAGGAGGCTC  TGAGGCTTTC  CAGTGCATCC  TTGAATATCC
7741  GGACTGCTAA  GGAGGATTTC  ACTCTGCACC  TTGAGGATGG  CTCCTATAAC  ATCCGAAAAG
7801  ACGACATCAT  CGCTCTTTAT  CCACAGTTAA  TGCATTTGGA  TCCTGCAATC  TACCCAGACC
7861  CTCTGGTAAG  TTTTCTGCT   CATCAAAGTT  ATGTATCGAG  GTGACAGTCA  CCCAGGAATG
7921  TATTTGTAAT  TACAGCTTTG  ATTTGATCAT  TAAAGTGAAG  CCATAGGGAT  TGTCCCTCTT
7981  TATTGCGGCA  AATATTCATG  TTTGGAAAC   TTTGGGTAGA  GGCAAGAGTT  TTGAACTTTT
8041  ACACCTAATA  TTCATTTCAT  AGTTTCTGCT  AGACTATGTT  TTCAGTCATA  ACAAAACTAC
8101  CACCTTTTTT  CCCCCTCACA  AGTACCCCTC  TCCCAAATTT  ACACTAATGG  AGGGTAATGC
```

FIG. 12H

```
8161 ATTGACTTG ATCCTTAGAG TAGTTGTTTA GAGCCATTTT GCTTCTTTTG TCTAACTGAA
8221 GAATTAGTCT ACAGGTAGAA CAGGAGGTCC CTAGAGCTTC TTGGTCCACC AGCTCTTCAT
8281 AAGCTCTTTC CAGTATCACC TGGTTCAGTG CTTGGTGTTT GCTAACTTGT AGAGGATGGA
8341 TTTATTAGTA GAAAATTACT CTTTGGATCC TCCAGGTCAA GAAGGCAACA ACTTCTATC
8401 ATAATAGCTC ATTGGCTTCT TGTCTCTTTG TTGCAGACTT TTAAATATGA TCGATACCTG
8461 GATGAGAACA AGAAGGCAAA GACCCTCCTC TATAGCAATG GAAACAAACT AAAGTATTTC
8521 TATATGCCAT TGGATCCGG AGCTACAATA TGCCCCTGGGA GACTATTGC TGTCCAAGAA
8581 ATCAAGCAAT TTTTGATTCT GATGCTTTCA TACTTTGAAC TGGAGCTTGT GGAGAGTCAT
8641 GTCAAGTGTC CTCCTCTAGA CCAGTCCAGG GCAGGCTTGG GGATTTGCC ACCATTAAAT
8701 GATATTGAGT TTAAATATAA ACTGAAACAT CTGTGACATG TGGTTGGAAG AAGAGGACAC
8761 TGGATGATGT TGCTGGACTG CAGCGAGTCT CACTAAACAA GCCCTTGGGA CAAATGCTCT
8821 CCTTTGCTTC CCAGCAACTG ACTGTGCCTA GGAAAAGAAC TGGTACCCCC GGCACCACTC
8881 TCTGTTCTCA CTGCCTGAGT TCCTGGGTGT TCAGATAGCT GAGGTCAGAG TTTCACCACT
8941 CTTAGAAGCA ATGTCTTTTG TTTTATTTT CAAAATGAAG ATACTCCAAT TGGCAGATTT
9001 TTTTTCCTAA GGAAATTGCT TCATACTTTT ATGAAAACTG ATTAATTATG AAAAGGCTTC
9061 AAATTCACGT TTTAGTGAAA CTGTTATTTT TTTCACTAGT GAAGTTCTTC ATGTGTGAAC
9121 ATATACTATA AAAACATTTT AAGGATCAT ATCATGCTTT GCATAAAGGG AAAGGAAAAT
9181 ATTATTCAAC TTTTTTTTTT GGTTTTTCTA GACAGGGTTT CTCTGTGTAG CTTTGGAGCC
9241 TATCCCTGGCA CTCACTCTGT AGACCAGGCT TGTCTTGAA CTCACAGAGA TCTGCCCTGCC
9301 TTTGCCTTCC GAGTGCTGGG ATTAAAGTCG TGCGGTCACCA ATGCCTGGCT ATTTAACTTT
```

FIG. 12I

```
9361  TTCGATGTCT AGTGGTGAGA GCTTTGAAAA TGATGCTACT GTGTTGGGAA TACTATGGGA
9421  AATTTGATG  CTTCGCTGTT ACATTAAAT  TTATTGCTGC TGGAAATTGT CACCCCAGTT
9481  TTCAATTGCC CCTCTCTCTC CCTTTAATA  TTCACACTGA TGAGCAGAGT TTTTAGAGA
9541  TTAAAAGAC  CTCCCCAGAG CCCTGTCTCT GATGTTTTTA AGCCTTTAAT CTCAGTACTC
9601  AGGAGGCAGA GGCAGGCAGA GCTCTGTGAG TTCGAGGCCA GCCTGATCTA CAGATCGAGT
9661  TCCAGGCAAG CCGGGGCTAC AGAATGAGAC CTTGTCACTA AAAGAAATAA ATAAGGTCAA
9721  TTTTATGTCA CAACTGATTA TGAATCATTG TAAAGGATAA ATTGAAAAAA AAGAACTCCA
9781  CGGGAATGAC CATTTAAATG GTCTATTTTA GCTAAAATTA ACTATGAATT ATGTGGAGTT
9841  CATTAAGTGT ATGTTGACGT TATATGTTCC TTTAAAATGT CTTATGTTTT ATCTCTGAAT
9901  GTCTTGTAGA TGGAGAGCAA TAATAGTGTT TAAATACTGA GTCAATAAGG TTTTATCTAT
9961  GTACTTTAAG AGCATTATTA GCTGTGTCAT TTTTACTGAT ATATCTAATA TATTATATG
10021 TAAATTATAT TTATCTTTTA TCTTATACTA CAAATATAAG TAAATATTTT AAAACCAGTA
10081 ACTTTAAAAT TACCTACCTT TCAGAAATGA AAATAAGAAC ATTTGTGCTT TAACCTTTGA
10141 AATAGAATGT TTATTCATCC ACTGATAAGT TAAAATAATT TTATCTGATT TGTTTCAAGA
10201 AACTCAAAA  TATTCAAAGT AATCATGCAC TCAAAGGTCT TCGTAAGGTT ACAGAAAATT
10261 CAATAAAATC TTTTTGTGT  AGGGACTGAG TCAGGGTCTA GAAGATGCTT GGCAGGTACT
10321 CCAGTAGTGA GCTGGATCCA GAAGATTCCT TAAACTTTAA AATCTTAACA CTAAGTATTA
10381 TCACAGAGTT ATTACCTAAG TAGAATATTT TTCCTTTCCT TTTCAATTGA CAGAGTCCCA
10441 CAGCAACACA GCTGGCTGTA ACTCTTCACA TAGCTTGCGC AGGCTTTGAA CTCACTGTAC
10501 TCCTGCCTTT CCTTTCTAG  GAAATTATTT TCCACATCAA GAAAATTTAA TTGTTCCGAT
10561 GAGGTATAGA GTAACAAATT TCTGTTATAT ATTCATCTGT ATTAAACTGA ATTC
```

5,558,999

CHOLESTEROL 7α-HYDROXYLASE GENE REGULATORY ELEMENTS AND METHODS FOR USING THEM

Work related to subject matter described in this application was provided by research supported in part by NIH Grant GM 31584.

CROSS REFERENCE TO RELATED APPLICATIONS

U.S. patent application Ser. No. 08/135,488 (Attorney Docket No. 18748/174) "GENOMIC DNA OF HUMAN CHOLESTEROL 7α-HYDROXYLASE AND METHODS FOR USING IT" to Chiang, J. and U.S. patent application Ser. No. 08/135,511 (Attorney Docket No. 18748/175) "CHOLESTEROL 7α-HYDROXYLASE GENE REGULATING ELEMENTS AND METHODS FOR USING THEM," Chiang, J., are both filed concurrently herewith and their disclosures are expressly incorporated herein by reference in their entirety.

BACKGROUND OF THE INVENTION

High serum cholesterol is commonly associated with an increased risk of heart attack, atherosclerosis and circulatory disorders. In addition, a variety of diseases are caused by disorder of cholesterol catabolism, such as gallstone disease, atherosclerosis, hyperlipidemia and some lipid storage diseases.

The major pathway for disposal of cholesterol in the body is by secretion of cholesterol and bile acids into the gut. Bile contains free cholesterol and bile acids. The enzyme, cholesterol 7α-hydroxylase (CYP7) commits cholesterol to bile acid synthesis and catalyzes the first and rate-limiting step of bile acid synthesis in the liver. Thus, by increasing synthesis of bile acids, this enzyme plays a key role in the liver by depleting hepatic cholesterol pools, resulting in increased LDL uptake and a lowering of serum cholesterol levels.

Bile acids are physiological agents which are important in the solubilization of lipid-soluble vitamin, sterol and xenobiotics. Bile acids are synthesized exclusively in the liver and are secreted to the intestines where they are modified to secondary bile acids. Most bile acids are reabsorbed in the ileum and recirculated to the hepatocytes via portal vein.

The feedback of bile into the liver is known to inhibit cholesterol 7α-hydroxylase and thus inhibit the overall rate of bile acid synthesis. Cholesterol 7α-hydroxylase therefore has been a subject of intense studies to elucidate the regulatory mechanisms of bile acid synthesis in the liver.

It is known that an interruption of bile acid reabsorption, such as caused by the bile sequestrant, cholestyramine, or by a bile fistula, stimulates the rate of bile acid synthesis and cholesterol 7α-hydroxylase activity in the liver. It is believed that cholesterol 7α-hydroxylase activity in the liver is regulated primarily at the gene transcriptional level by bile acids, cholesterol, hormones, diurnal rhythm and other factors.

Generally, the regulation of eukaryotic genes is thought to occur at several locations, including the promoter sequences, located upstream of the transcription start site; enhancer or repressor sequences, located upstream of the promoter; within intron sequences, non-coding sequences located between exons or coding sequence; and in 3' sequences, located downstream from the coding region. The promoter sequence is unique to each gene and is required for the accurate and efficient initiation of gene transcription. Enhancers and/or repressors regulate promoter activity and determine the level of gene transcription during development and differentiation of a particular tissue.

The promoter of most eukaryotic genes contains a canonical TATA box which binds a TFIID TATA box binding protein. TFIID complex and associated transcription activators (TAFs) interact with the basal initiation factors and RNA polymerase II to activate promoter. The transcription complex assembly and initiation are regulated by transcription factors bound to enhancer elements located in the promoter and other regions of the gene (Pugh and Tjian, J. Biol. Chem. 267, 679–682, 1992). Tissue-specific transcription factors and nuclear steroid hormone receptors are known to play an important role in the regulation of gene expression in different tissues during development and differentiation.

However, the mechanisms underlying the regulation of cholesterol 7α-hydroxylase CYP7 gene expression at the molecular level are not understood. An understanding of regulation of CYP7 gene expression would permit development of therapeutics for treating patients with defects in bile acid synthesis and cholesterol metabolism due to altered (deficient or excessive) gene expression.

In order to study the mechanism of regulation of human cholesterol 7α-hydroxylase at the molecular level, it is therefore important to determine the correct gene sequence of its coding and promoter regions. An elucidation of its gene structure and its promoter/enhancer activity is sought in order to assay for an agent that modulates cholesterol 7α-hydroxylase enzyme regulation. Thus, a method for screening compounds for inhibition or stimulation of expression of the enzyme is desired, as well as a method for detecting and isolating the gene's transcription factors.

SUMMARY OF THE INVENTION

An embodiment of the invention provides a DNA sequence that comprises at least one regulatory element of cholesterol 7α-hydroxylase expression. In an advantageous embodiment, the DNA sequence comprises at least one regulatory element of cholesterol 7α-hydroxylase expression in either rat, human or hamster.

An advantageous embodiment provides a DNA sequence comprising a regulatory element of the cholesterol 7α-hydroxylase (CYP7) gene selected from DNA fragments in the group consisting of from about −191 to +64 of the rat CYP7 gene, from about −252 to +3 of the hamster CYP7 gene and from about −187 to +65 of the human CYP7 gene, or functionally active parts thereof.

Another advantageous embodiment provides DNA selected from fragments of DNA identified in Table 1, columns 1–3.

Another advantageous embodiment of the invention provides a gene construct containing at least one of the foregoing regulatory elements and a reporter gene.

Another embodiment provides a method for determining whether an agent inhibits or stimulates CYP7 gene expression. Yet other embodiments provide methods for detecting and isolating the transcription factors of the cholesterol 7α-hydroxylase gene.

BRIEF DESCRIPTION OF THE DRAWINGS

FIGS. 2A, 2B and 2C provide maps of the human CYP7 gene and clones λHG7α26 and λHG7α5. FIG. 2A shows the gene map of human CYP7. FIG. 2B shows the gene map of the λHGYα26 clone. FIG. 2C shows the gene map of the λHG7α5 clone. Heavy boxes represent exons I, II, and III. The arrows indicate regions for which nucleic acid sequences now are determined. These sequences are shown in FIGS. 9, 10 and 11.

FIGS. 7A, 7B and 7C show the amino acid sequences of human, rat and hamster CYP7 (SEQ ID NOS 28, 29 and 30, respectively). FIG. 7A shows the human amino acid sequence, FIG. 7B shows the rat amino acid sequence and FIG. 7C shows the hamster amino acid sequence.

FIGS. 8A–8G show the nucleotide sequence (SEQ ID NO:31) of the region of the rat CYP7 gene that is indicated by arrows in FIG. 1. The transcription start site "G" is located at nucleotide position 3617. Exon I (3617–3757), Exon II (5373–5613), Exon III (6321–6907) and Exon IV (7901–7970) are indicated by brackets.

FIGS. 9A–9E show the approximately 5.5 kb nucleotide sequence (SEQ ID NO:32) of the λHG7α26 clone indicated by arrows in FIG. 2B.

FIGS. 10A–10B show the approximately 2.6 kb nucleotide sequence (SEQ ID NO:33) of the λHG7α26 clone indicated by arrows in FIG. 2B.

FIGS. 11A–11B show the approximately 2.3 kb nucleotide sequence (SEQ ID NO:34) of the λHG7α5 clone indicated by arrows in FIG. 2C.

FIGS. 12A–12I show the nucleotide sequence (SEQ ID NO:35) of the region of the hamster CYP7 gene indicated by arrows in FIG. 3.

DETAILED DESCRIPTION OF THE PREFERRED EMBODIMENTS

It was found, surprisingly, that DNA fragments comprising nucleotides downstream from about −187 of the human CYP7 gene, downstream from about −191 of the rat CYP7 gene, and downstream from about −252 of the hamster CYP7 gene are regions that exert regulatory control of transcription of the human, rat and hamster CYP7 gene, respectively.

According to the present invention, the term "regulatory" means a characteristic ability of a DNA fragment to exert transcriptional control of a CYP7 gene in the presence of a factor that either down-regulates the CYP7 expression, e.g., bile salts or mevinolin, or up-regulates CYP7 expression, e.g., cholestyramine, bile fistula or cholesterol. Thus, a "regulatory element" refers to a DNA fragment disclosed in accordance with this invention that has regulatory activity with respect to CYP7.

Figure 4:
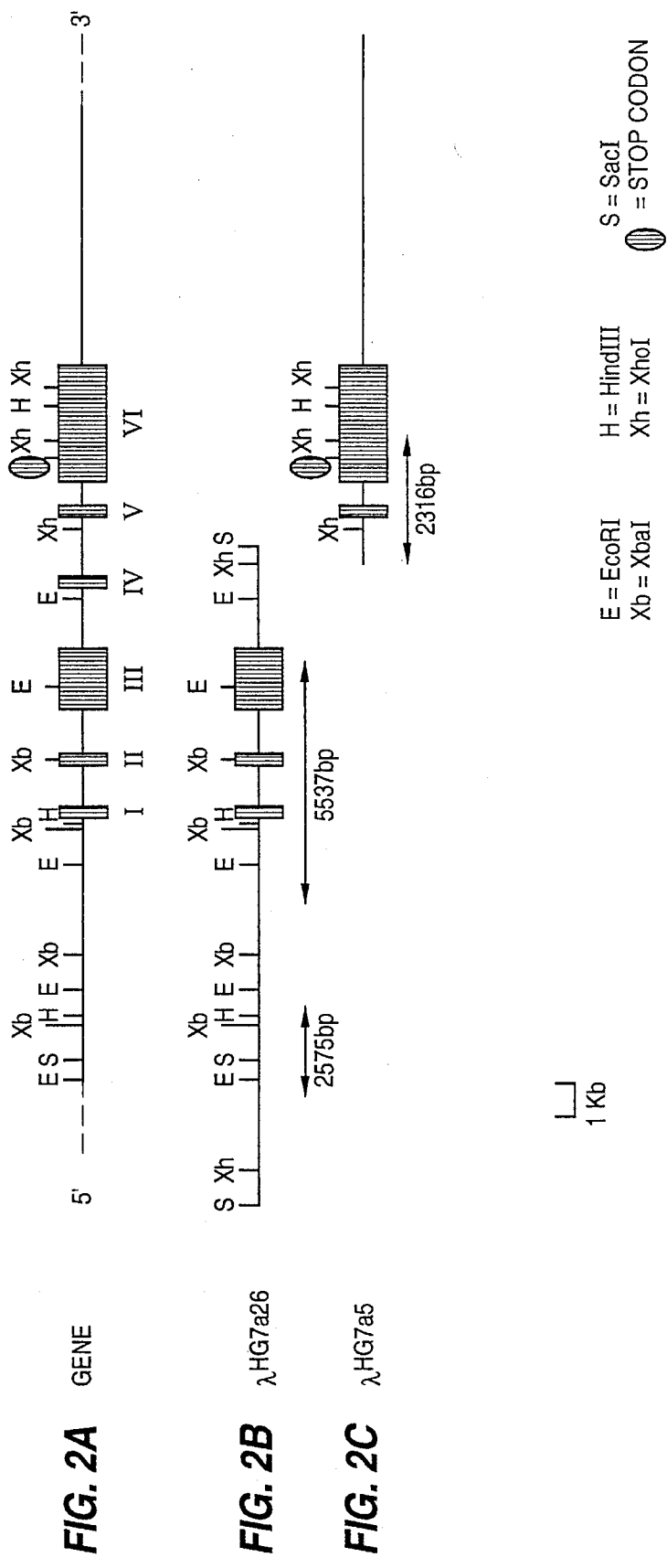
FIG. 4 shows an alignment of the proximal promoter regions of rat human and hamster CYP7 genes (SEQ ID NOS 25, 27 and 26, respectively). The following abbreviations are used: GRE, glucocorticoid response element; LFA1, liver factor 1; HRE, steroid/thyroid hormone response element; PPRE, peroxisome proliferator response element; TGT3, TGT3 element; and LFB1, liver factor B1. Transcription start sites "G" are indicated by a "*". Translation start codons "ATG" are underlined. The numbers indicate the nucleotide positions in each gene.

Therefore, an embodiment of the present invention provides a regulatory element of a CYP7 gene and selected from the group comprising DNA fragments, from about −191 to about 64 of the rat CYP7 gene, from about −252 to about 3 of the hamster CYP7 gene and from about −187 to about 65 of the human CYT7 gene, and regulatory DNA fragments spanning a region within these fragments (subfragments), such as fragments shown in FIG. 4 (SEQ ID NOS. 25, 26 and 27).

An advantageous regulatory element of the rat CYP7 gene is selected from the group of DNA fragments having regulatory activity and consisting of any of the eight fragments of DNA described in the first column of Table 1 below. The corresponding regulatory elements of hamster and human gene are closely homologous, as shown in FIG. 4, (SEQ ID NOS. 25, 26 and 27) and as listed in Table 1. Thus, an advantageous human CYP7 regulatory element is selected from the group consisting of any of the eight fragments of DNA described in the second column of Table 1, while an advantageous hamster CYP7 regulatory element is similarly selected from the group consisting of any of the eight fragments of column three of the Table. DNA fragments which begin at about the downstream nucleotides and end at about the upstream nucleotides that are recited in Table 1 are also contemplated.

In addition to a regulatory element selected from the fragments described above (comprising from about −191 to about 64 of the rat CYP7 gene, from about −252 to about 3 of the hamster CYP7 gene and from about −187 to about 65 of the human CYT7 gene, and fragments described in Table 1), it is contemplated that other substantially homologous sequences will have CYP7 regulatory activity and thus can be used as regulatory elements in accordance with this invention. Exemplary substantially homologous sequences include: substantially homologous sequences having at least about 80%, advantageously about 90% and more advantageously about 95% nucleotide sequence homology with respect to the described fragments; sequences having at least about 82%, and advantageously at least about 90%, homology between a pair of corresponding rat and hamster DNA sequences, such homology to the sequence from about −101 to about −29 of the rat CYP7 gene and the sequence from about −161 to about −86 of the hamster CYP7 gene, for example; and sequences having homology of at least about 71%, advantageously at least about 90%, between any pair of corresponding rat and human DNA sequences, for example, about −101 to about −29 of the rat CYP7 gene and the sequence from about −104 to about −30 of the human CYP7 gene.

TABLE 1

Regulatory elements of rat, human and hamster CYP7 gene

| (from transcript. start site) | | (from start codon) |
| --- | --- | --- |
| I. Rat | II. Human | III. Hamster |
| −101 to −29 | −104 to −30 | −161 to −86 |
| −81 to −37 | −78 to −36 | −136 to −92 |
| −161 to −127 | −159 to −124 | −208 to −184 |
| −149 to −131 | −147 to −128 | −206 to −188 |
| −171 to −154 | −169 to −152 | −228 to −211 |
| −101 to −82 | −104 to −79 | −161 to −137 |
| −73 to −56 | −71 to −54 | −128 to −111 |
| −86 to −71 | −89 to −68 | −146 to −126 |

Further embodiments of the present invention include a recombinant construct comprising at least one of the above-mentioned regulatory elements, advantageously a fragment disclosed in Table 1. Advantageously, for example, a regulatory element can be operably attached to a structural gene encoding CYP7, or to a reporter protein. Operably attached means that the regulatory element is positioned with respect to the structural gene such that it exerts control of the transcription of the structural gene.

A construct according to the invention can be provided in a vector capable of transforming a host cell. A host cell transformed or transfected with such a vector also comprises an embodiment of this invention, as well as a method for expressing a selected structural gene, advantageously CYP7 or a reporter gene, using host cells of this invention. Such a method of expression comprises the steps of culturing a host cell transformed with a recombinant DNA vector comprising a gene construct comprising at least one regulatory element operably attached to the selected structural gene, wherein culturing is performed in a medium that is suitable for accommodating the desired expression, and producing the gene product.

A reporter gene allows quantitative determination of gene expression in the presence of inhibitory or stimulatory compounds. A host cell transformed with a recombinant DNA vector comprising a gene construct of at least one regulatory element operably attached to the selected structural provides an expression system useful in a conventional method to screen a compound for its ability to inhibit or stimulate structural gene expression. Thus, an example of a screening method provides contacting the host cell with a test compound and detecting an inhibition or stimulation of gene expression. A test compound can comprise, for example, a physiological agent derived from substances endogenous to a human or, an exogenous compound.

Thus, regulatory elements, in particular those fragments identified in Table 1, are used to control expression of structural genes, such as the CYP7 gene, and various reporter or indicator genes, such as exemplified in Example 2.4. Reporter genes include, but are not limited to, $E.$ $coli$ β-galactosidase, galactokinase, interleukin 2, thymidine kinase, alkaline phosphatase, luciferase and chloramphenicol acetyltransferase (CAT). Those skilled in the art readily will recognize additional reporter genes.

A representative construct of regulatory element and reporter gene is made according to Example 2.4, which employs, for example, the rat regulatory element −101 to −29. Any of the other regulatory elements according to the invention, preferably those described in Table 1, can be substituted for that rat fragment −101 to −29, by using conventional genetic engineering methods.

The inventive regulatory elements are also useful for detecting and isolating a transcription factor of CYP7. To detect a transcription factor, a regulatory element according to the invention, preferably an element from Table 1, is contacted with a biological sample suspected of containing a transcription factor. Binding between the fragment and a transcription factor and the step of isolating the transcription factor are accomplished by conventional methods.

For example, to isolate a transcription factor, the following steps can be employed. First, a footprinting assay is performed to determine whether a particular gene fragment, such as a regulatory element according to the invention, binds to a nuclear transcription factor. The footprinted sequence that is revealed is used to identify DNA-protein interactions by electrophoretic mobility assay (EMSA). If a band shift is detected in EMSA, the shifted sequence is confirmed by Southwestern blot. The Southwestern blot, by SDS-polyacrylamide gel electrophoresis separates nuclear proteins. A separated protein then is incubated with a shifted DNA sequence to identify a nuclear transcription factor. The DNA sequence then is used to screen an expression cDNA library for cDNA clones encoding a transcription factor. In an alternative method, a DNA fragment of the invention can be fixed to an affinity column and used to isolate a transcription factor present in nuclear extracts (See Example 2).

An identified transcription factor can be cloned and expressed in relatively high amounts and then employed in screening compounds for the ability to influence gene expression via the specific transcription factor.

The following examples illustrate the invention and, as such, are not to be considered as limiting the invention set forth in the claims. Either human or hamster regulatory elements can be substituted for rat regulatory elements in the following examples.

EXAMPLE 1

Cloning and Nucleotide Sequencing of the CYP7 Genes

A. The Rat Gene

Figure 1:
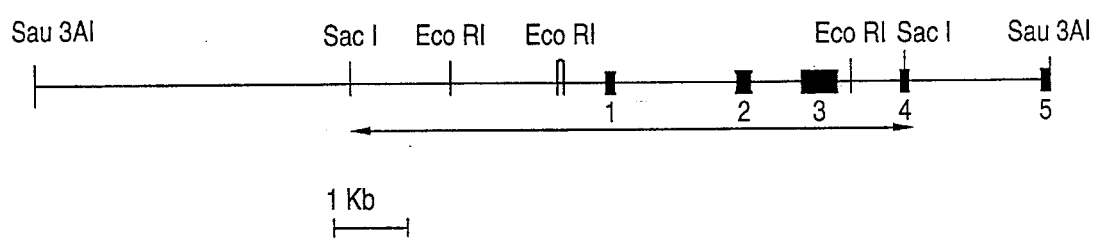
FIG. 1 illustrates the rat CYP7 gene map. Boxes indicate exons. The arrows indicate the region for which a nucleic acid sequence (shown in FIG. 8) now is determined.

A rat genomic library (Clontech, RL1022j) was screened with a rat cholesterol 7α-hydroxylase cDNA previously isolated by Li et al., $J.$ $Biol.$ $Chem.$ 265, 12012–12019, (1990). After screening about 1 million plaque-forming units (pfu), a positive clone, λR7α2 was plaque-purified. This clone contains a 13 kb insert that spans 8 kb of the 5'-flanking region as well as the transcription region covering exons 1 through 3 and a partial exon 4 (FIG. 1). The nucleotide sequencing of an 8 (SEQ ID NO:31) kb SacI fragment is shown in FIG. 8 and includes the 3616 bp 5'-flanking region and coding region from exon 1 to exon 4. This fragment includes about 2 kb of the 5'-upstream region, the sequence of which was published recently by the inventor (Chiang, et al., $Biochim.$ $Biophys.$ $Acta.$ 1132, 337–339, 1992). Many putative regulatory elements, including liver-enriched hepatic nuclear factors (HNFs) binding sites, steroid/thyroid hormone response elements, and ubiquitous transcription factor binding motifs (NF1, OTF-1), were identified in this gene fragment.

It was shown previously that high cholesterol diet up-regulates transcription of the cholesterol 7α-hydroxylase gene, translation of CYP7 mRNA, and increases enzyme expression and activity in rat liver (Li, et al. $J.$ $Biol.$ $Chem.$ 265, 12012–12019, 1990). It is especially noteworthy that steroid regulatory elements (SREs) similar to those found in the LDL receptor, HMG-CoA reductase, and HMG CoA synthase genes are located in the upstream region of the rat CYP7 gene promoter. These SREs are not present in the human or hamster CYP7 gene promoter. These SRE's are −1222-ATCCTCTCCCCAC TCCCAAG CATCCCTCCATG −1191 (SEQ ID NO:1), −1151-CAACTCCTCCCCTATT-1335 (SEQ ID NO:2). Repeats 1 and 2 in the rat CYP7 gene are similar to the consensus SRE1 (CACC(C/G)(C/T)AC), which represses gene expression in the presence of oxysterols. The repeat 3 of the LDL receptor SRE has 11 bases identical to the sequence between −1151 to −1335 of the rat CYP7 gene. This sequence has been demonstrated to bind Sp1 which is a positive transcription factor in the LDL receptor gene (Dawson, et al. J. Biol. Chem. 263, 3372-3379, 1988).

B. The Human Gene

A human genomic library, which had been constructed with Sau3A1 partially digested human placental DNA ligated into a BamHI site of the EMBL-3 Sp6/T7 phage vector (Clontech, Palo Alto, Calif.) was screened using a 1.6 kb EcoRI-PstI fragment of a human cholesterol 7α-hydroxylase cDNA isolated previously as a hybridization probe. Human CYP7 cDNA was isolated previously by Karam and Chiang, *BBRC* 185:588 (1992). Hybridizations were carried out at a high stringency condition of 68° C., 1% SDS and 0.1× SSC. 800,000 pfu of phages were screened. After four cycles of screening, seven positive clones were plaque-purified. Three clones comprising the largest inserts (λHGα26, λHGα5 and λHGα52) were isolated and analyzed by restriction mapping. FIG. 2A shows the complete gene map of human CYP7. Clone λHGα26 (FIG. 2B) contains a 15 kb insert which spans about 8.0 kb of the 5'-upstream flanking sequence and exons I to III (FIGS. 9A–9E and 10A–10B, SEQ ID NOS. 32 and 33, respectively). Clone λHGα5 (FIG. 2C) contains sequences from intron IV, exons V and VI to an 8.0 kb 3'-flanking sequence (FIG. 11 SEQ ID NO:34).

Cloned bacteriophage λHG7α26 and λHG7α5 were deposited Aug. 25, 1993 at the American Type Culture Collection, ATCC, 12301 Parkland Drive, Rockville, Md. 20852, U.S.A., under accession numbers ATCC 75534 and 75535, respectively.

Five EcoRI fragments of the clone λHGα26 were excised from the phage DNA insert by restriction digestion and shotgun subcloned into the phagemid vector pBluescript II KS+ (Stratagene, La Jolla, Calif.). The clones were size-selected. EcoRI fragments were isolated from CsCl purified plasmids and used for sequencing. Nested deletions were generated by ExoIII/Mung Bean nuclease digestion according to the manufacturer's instruction (Stratagene, Calif.) using the conditions of a 37° C. incubation for 1 min intervals. This condition resulted in an average deletion of about 200 to 250 bp/min. DNA sequencing of the nested deletions was carried out by the dideoxy chain termination method using T7 sequence version 2.0 (USB, Cleveland, Ohio) and $^{35}$S-dATP. Sequence data were obtained from both strands and the overlapping deletion clones and analyzed using DNASIS software (Hitachi America, Calif.).

The nucleotide sequences of a 5.5 kb EcoRI fragment (FIGS. 9A–9E) SEQ ID NO:32 and a 2.6 kb EcoRI fragment (FIGS. 10A–10B) SEQ ID NO:33 were determined. The 5 kb fragment contains the sequence from −1886 of the 5'-upstream region to a partial exon 3 (FIG. 2B). Included in FIG. 9 also is the 347 bp 3'-end sequence of a 3.5 Kb EcoRI fragment located immediately upstream of this 5.5 kb fragment (FIG. 2B). As shown in FIG. 2A, the 2.6 kb fragment is located further 5' upstream of the 3.5 kb EcoRI fragment. Thus, a 4823 bp 5'-upstream flanking region sequence of the gene now is determined.

Molowa et al. (*Biochem.* 31, 2539–2544, 1992) published a 1.7 kb upstream sequence of a human gene. A comparison of the sequence of the present invention to that of Molowa et al. in the overlapping region (1604 bp) revealed that sequences from the transcription start site to about −460 are identical, however, further upstream the sequence vary significantly. A total of 52 sequence discrepancies were found, which are far too many to attribute only to the presence of polymorphisms in the human gene. Cohen et al. (*Genomics*, 14, 153–161, 1992) reported a 723 bp upstream sequence and suggested sequencing errors by Molowa et al. Thus, the sequence of the present invention, from the transcription start site (nt+1) to −587, is identical to those reported previously by Molowa et al., Nishimoto et al., (*Biochem. Biophys. Acta*, 1122, 147–150, 1993) and Thompson et al., (*Biochim. Biophys. Acta*. 1168, 239–242, 1993).

The present invention identifies seven mismatches in Cohen's sequence from +1 to −123. A conversion of at T to C nucleotide −469 was identified to be a Mae II polymorphism (Thompson et al., 1993). The 5'-flanking sequence of the present invention agrees very well with that reported by Thompson et al. (1993). Only one mismatch at nucleotide −1193 (C vs A) was found in the overlapping region from +1 to nucleotide −2235.

The present invention further identifies transcription factor binding motifs in the human gene, however, SRE-like sequences were not found in the human promoter region.

C. The Hamster Gene

Figure 3:
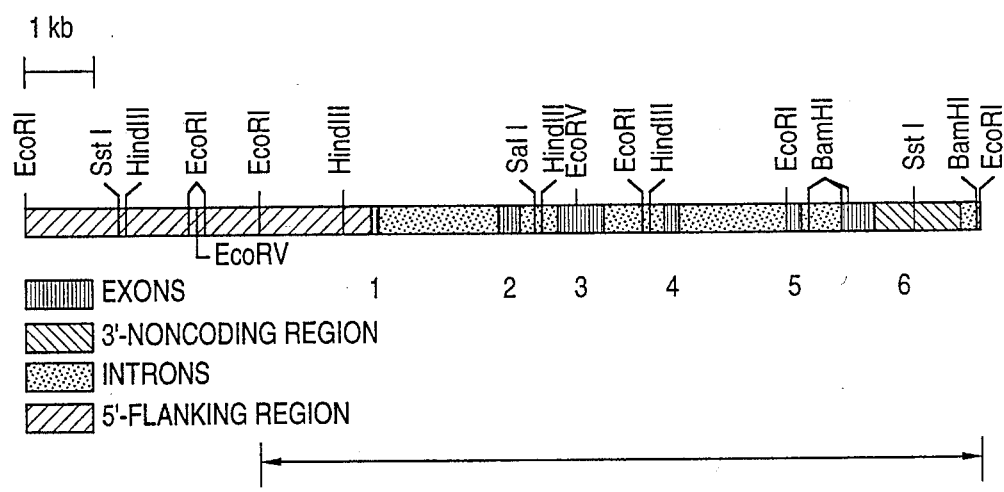
FIG. 3 illustrates the hamster CYP7 gene map. The arrows indicate the region for which a sequence (shown in FIG. 12) now is determined.

A hamster liver genomic library constructed in the λDASH II vector (Stratagene) was screened with a 2.5 kb Eco RI fragment of the rat pBSK7α12 comprising the entire coding sequence of the rat cholesterol 7α-hydroxylase cDNA. About 1 million plaque-forming units were screened and one positive clone was identified and plaque-purified. The phage DNA was purified by CsCl gradient centrifugation and cDNA insert was restriction-mapped using rat probes (FIG. 3). EcoRI fragments of the DNA were isolated and subcloned into a pBluescript II KS+ vector. Nested deletions were generated with an ExoIII/Mung Bean deletion kit. The DNA sequences of these deletions were determined by the dideoxy chain termination method using Sequenase. In some instances 17-mer synthetic oligonucleotides were designed and used as sequencing primers. Sequences were determined on both strands with overlaps. cDNA sequence analyses were carried out with DNASIS software.

FIGS. 12A–12I show the 11 kb DNA sequence (SEQ ID NO:35) of the hamster gene. It covers the sequence from nucleotide- 1650 of the 5'-flanking region through all six exons and five introns (Exon I: nucleotide 1651–1730; Exon II: 3511–3650; Exon III: 4351–4937; Exon IV: 5945–6075; Exon V: 7690–7865; Exon VI: 8437–8736). The amino acid codons interrupted by introns are identical in each of these three homologous genes. The DNA sequence of the exon-intron junctions follows the canonical GT-AG rule typical of eukaryotic genes. The precise intron sizes determined by DNA sequencing are consistent with those of the rat. The intron 3 of the hamster gene is 1007 bp, which is about 1 kb shorter than that estimated for human intron 3. A putative polyadenylation signal (AATAAA) is located 371 bp upstream from the 3'-end of the gene, indicating that the isolated genomic clone should include the entire coding exon 6.

EXAMPLE 2

Regulatory Elements and Transcription Factors

Cloning of the CYP7 gene from three different species allows the analysis of the CYP7 gene structure and organization. Alignment and analysis of the highly conserved proximal promoter region of these homologous gene suggests that many regulatory elements are conserved and are likely to play important roles in gene regulation. Mapping of these transcription factor binding sites is essential to the isolation of transcription factors involving in the regulation of liver-specific CYP7 gene transcription. These sequence elements and protein factors are potential models for designing compounds and for screening for activators or repressors of the gene, such as described in copending U.S. application Ser. No. 08/135,488, (Attorney Docket No. 18748/174) to Chiang, J. The following discussion relates to the regulatory elements and transcription factors of the rat gene promoter.

2.1. Alignment and Analysis of the CYP7 Genes

Figure 5:
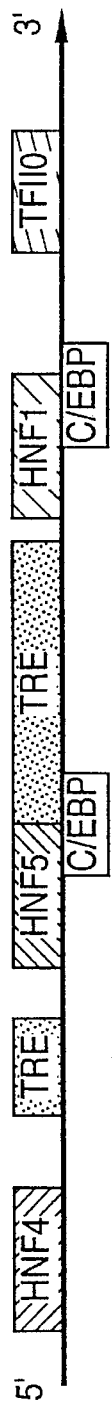
FIG. 5 shows a diagram indicating the positions at which transcription factors bind to the CYP7 proximal promoter. The following abbreviations are used: HNF, hepatocyte nuclear factor; TRE, thyroid hormone response element; C/EBP, liver specific enhancer binding protein; and TFIID, TATA box binding site representing general transcription complex.

The proximal promoter regions of the rat, human and hamster genes were aligned. Sequence identity is about 82% between rat and hamster, 77% between hamster and human and 71% between human and rat (FIG. 4 (SEQ ID NOS. 25, 26 and 27)). Several liver-enriched transcription factors, HNF3, HNF4, HNF1 and C/EBP, and thyroid/steroid hormone response elements are highly conserved in these homologous genes (FIG. 5). Sequences that are further upstream of these genes have diverged considerably. In contrast to the report that the −400 proximal promoter of the human gene had no promoter activity (Molowa, et al. Biochem. 31, 2539–2544, 1992), this conservation indicates that the proximal promoter is important in transcriptional activation function and contains essential regulatory elements.

2.2. Footprint Analysis of the Rat Gene

Figure 6:
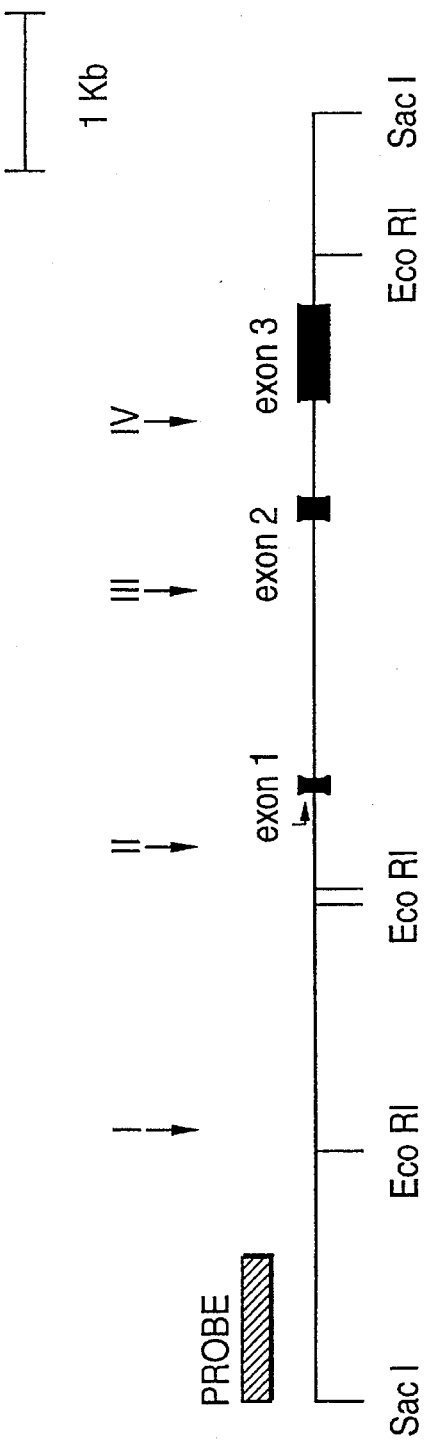
FIG. 6 shows the DNase I hypersensitivity sites (I, II, III and IV) in the SacI fragment of the rat CYP7 gene. Heavy boxes are exons. A 5'-probe was used for hybridization.

DNase I hypersensitivity sites of the rat gene were mapped by digestion of rat liver nuclei (20 OD$_{260}$) with DNase I at 37° C. for time periods up to 4 minutes. DNA was isolated from nuclei at each time interval and digested with SacI, fractionated on a 0.8% agarose gel and transferred to nylon membranes. A 5'-probe of Sac I-EcoRI fragment (−3616 to −2265) was used for indirect end-labeling and was labeled with an activity of at least 1×10$^9$ CPM/μg. Four DNase I hypersensitivity sites (HSI, HSII, HSIII, HSIV) were mapped. HSI is mapped near a "CA" repeat region around nucleotide-1,500. HSII is located in the proximal promoter region. HSIII and HSIV are located in intron I and intron II, respectively (FIG. 6).

DNase I footprinting technique then was applied to map the transcription factor binding sites in the gene promoter (Heberlein, U., England, B. and Tjian, R. Cell, 41, 965–977, 1985). Transcription factor binding sites in the gene are protected from DNase I digestion. Two fragments were mapped: a Hind III-Xba I fragment (−346 to +36) in the proximal promoter region near the hypersensitivity site II and an upstream fragment Xba I-Hind III (−1530 to −1205) in the hypersensitivity site I. Probes were made from plasmid DNA digested with a restriction enzyme to generate a 5'-overhang, filled in with the Klenow fragment of DNA polymerase I and $^{32}$P-labeled dCTP, and then digested with a second restriction enzyme. Probes were purified from a native 5% polyacrylamide gel. Footprinting reactions included 2 μg of poly(dI-dC), 10% polyvinyl alcohol, 50 mM KCl and 20 fmol of probe in a volume of 50 μl. Reactions were stopped with EDTA and SDS, then phenol extracted, ethanol precipitated and run on polyacrylamide sequencing gels.

The footprinted areas are summarized as follows:

Footprints (FP) mapped in hypersensitivity site II:
FP I (Nucleotides −81 to −37 SEQ ID NO:3): TGT3, 7α-TRE, HNF1/LBF1, CAAT, Box Elements 5'-TGTTTGCTTTGGTCACTCAAGTTCAAGT-TATTGGATCATGGTCC-3'

FP II (Nucleotides −149 to "131 SEQ ID NO:4): HNF4/LFA1 element 5'-CTATGGACTTAGT-TCAAGG-3'

FP III (Nucleotides −171 to −154 SEQ ID NO:5): GRE half site 5'-TGTTCTGGAGCCTCTTCT-3'

Footprint mapped in hypersensitivity site I:
FP IV (Nucleotides −1448 to −1410 SEQ ID NO:6): NF1 elements 5'-TCACTGTGGCCTAGTGCCA-CATCTACCTATTTCTTTGGCTTTAC-TTTGT-3'

Footprint I covers a sequence from nucleotide −81 to −37 and consists of four elements: TGT3/HNF3, 7α-TRE, LFB1/HNF1, and CAAT box (reversed). Footprint II covers sequence from −149 to −131 and contains an LFA1/HNF4 site. Footprint III covers sequences from −171 to −154 and contains a consensus glucocorticoid response element (GRE) half site. In the hypersensitivity site I, a footprint covers −1554 to −1505 and contains a bipartite and a half-site of the NF1/CTF element. Most of these sequences are liver-enriched transcription factor consensus motifs and are highly conserved in all three species. It is especially interesting that Footprint I contains overlapping binding sites for at least four transcription factors, HNF3α/3β, 7α-TRE, HNF1/LFB1, and C/EBP. The TRE-like sequence (TGGTCANNNNAGTTCA SEQ ID NO:7), located in the center of the cluster may be the binding site for Type II hormone receptors such as the T$_3$ receptor (T$_3$R), the retinoic acid receptor (RAR), the retinoid X receptor (RXR), the vitamin D$_3$ receptor (VD$_3$R), or the peroxisome proliferator activating receptor (PPAR) (Stunnenberg, H. G., BioEssays, 15, 309–315, 1993). This gene fragment has been shown to be essential for major promoter activity and could confer taurocholate repression of promoter activity in rat primary hepatocyte cultures. It is likely that the element in footprint I identified in the present invention is the bile acid response element (BARE) of the CYP7 gene.

2.3. Gel Mobility Shift Analysis of the Rat Gene

The electrophoretic mobility shift assay (EMSA) is used to detect specific DNA-protein interactions in the identified footprints. Oligonucleotides corresponding to PPRE/TRE, 7αTRE, and TGT3 were synthesized and annealed to form double-stranded probes. DNA fragments corresponding to Footprints I, II, and IV were generated by PCR using primers that flank the footprint sequences. Probes are labeled with $^{32}$P dCTP by the Klenow fragment of DNA polymerase I. Probes were gel purified before use. Binding reactions were done in 20 μl comprising 10% glycerol, 10 mM HEPES, pH 7.9, 2 μg of poly(dI-dC), 1 μg of nuclear protein extracts and 20,000 CPM of probes at 30° C. for 15 min, followed by electrophoresis on 4% native polyacrylamide gels (Carthew, R. W., et al. Cell, 43, 439–448, 1985).

The footprint I probe shifted at least 4 bands when it was reacted with liver nuclear extract. Cold competitor specifically prevented band shifts. The footprint II probe shifted two bands whereas Footprint IV probe shifted only one band with liver nuclear extract. Since Footprint I contains several transcription factor binding elements and is the possible bile acid receptor or binding protein (BAR) binding site, double-stranded oligonucleotides were synthesized corresponding to the TGT3 and 7α-TRE elements in Footprint I.

EMSA revealed that the TGT3 element shifted two major bands, which may be due to the binding of HNF3α and HHF3β, whereas the 7α-TRE element shifted two different bands. Protein factors that bind to the 7α-TRE probe could be competed out with a 100-fold excess of its cold competitor or a rat growth hormone gene TRE element. However, TGT3 and PPAR/TRE oligonucleotides did not compete with the 7α-TRE probe. These results indicate that the 7α-TRE like element identified in the CYP7 gene promoter binds to one or two specific liver protein factors. In addition, the 7α-TRE of the human CYP7 gene (FIG. 4 (SEQ ID NOS. 25, 26 and 27)) also shifted one band in human liver nuclear extracts.

Furthermore, EMSA was performed using liver nuclear extracts isolated from rats treated with a diet supplemented with 0.25% deoxycholate, 1% cholate, 5% cholestyramine or 1% cholesterol for two weeks. Only nuclear extracts from deoxycholate-treated rat liver abolished the gel shift of the 7α-TRE oligonucleotide. Deoxycholate or sodium cholate treatment reduced both cholesterol 7α-hydroxylase activity and mRNA levels by 80% and 60%, respectively, whereas cholestyramine or cholesterol treatment stimulated these parameters by 330% and 180%, respectively.

These results suggest that deoxycholate may inhibit the binding or synthesis of a positive nuclear transcription factor, (i.e. factor A) to the bile acid responsive element (BARE) or inhibit the synthesis of factor A in nuclei as well as repress CYP7 gene expression. Alternatively, deoxycholate may bind to a negative regulator, BAR, which forms a complex with the positive factor A and prevents the binding of factor A with BARE. BAR and nuclear transcription factor A may compete for the same binding site, BARE. These factors are likely members of the steroid/thyroid hormone supergene family, since the recognition sequence is similar to the cognate response element. Interactions between this transcription BAR with adjacent liver-enriched transcription factors (HNF3α, HNF3β, HNF1, C/EBP) can affect the expression levels of the CYP7 gene.

A Southwestern blot was performed to separate the nuclear proteins by SDS-gel electrophoresis. The proteins were transferred to a nitrocellulose membrane and then incubated with a radiolabeled oligonucleotide of 7α-TRE. It was found that cholestyramine treatment induced a protein having a molecular weight of about 50,000 that binds to 7α-TRE. Thus, the isolation of transcription factor(s), such as a transcription factor that is induced by cholestyramine or suppressed by bile salts, is now made possible by contacting nuclear extracts from liver with a BARE oligonucleotide-affinity column and screening a cDNA expression library from rat liver for cDNA clones encoding these transcription factors. Methods of isolating transcription factors according to the invention can employ DNA fragments according to the invention in conjunction with methodology taught by Singh et al., *Cell* 52: 415 (1988) and Kadonaga et al., *PNAS USA* 83: 5889 (1986). Each of these publications is incorporated by reference herein in their entirety.

The TRE-like BARE sequence in the CYP7 gene promoter can be used in EMSA to determine whether or not bile acid or its derivative is an inhibitor of CYP7 gene expression. It also could be used to screen for a compound that modulates the binding of a positive transcription factor to BARE and stimulates the expression of the CYP7 gene.

| Electrophoretic Mobility Shift Assay of DNA-protein Interactions | |
|---|---|
| Sequences of double-stranded probes | # of bands shifted |
| 1). FP I probe (−100 to −29): (SEQ ID NO. 8)<br>5'-CTAGTAGGAGGACAAATAGTGTTTGCTTTGGTCACTCAAGTTCAAGTTATTGGATCATGGTCC-3'<br>3'-GATCATCCTCCTGTTTATCACAAACGAAACCAGTGAGTTCAAGTTCAATAACCTAGTACCAGG-5' | four to five |
| 2). FP II probe (−161 TO −127): (SEQ ID NO: 9)<br>5'-CCTCTTCTGAGACTATGGACTTAGTTCAAGGCCGG-3'<br>3'-GGAGAAGACTCTGATACCTGAATCAAGTTCCGGCC-5' | two |
| 3). FP IV probe (−1454/−1394): (SEQ ID NO: 10)<br>5'-TCACTGTGGCCTAGTGCCACATCTACCTATTTCTTTGGCTTTACTTTGTGCTAGGTGACC-3'<br>3'-AGTGACACCGGATCACGGTGTAGATGGATAAAGAAACCGAAATGAAACACATCCACTGG-5' | one |
| 4). PPRE/TRE element probe (nt −101/−82): (SEQ ID NOS 11 and 12)<br>5'-GAAGATCTAGTAGGAGGACAAATAG 3'<br>3' CATCCTCCTGTTTATCAC 5' | two |
| 5). 7α-TRE element probe (nt −73/−56 in FP I): (SEQ ID NOS 13 and 14)<br>5'-GATCCTTGGTCACTCAAGTTC 3'<br>3' GAACCAGTGAGTTCAAGTTCCTAG 5' | two |
| 6). TGT3 element probe (nt −86/−71 in FP I): (SEQ ID NOS 15 and 16)<br>5'-GATCCAATAGTGTTTGCTTTGGT 3'<br>3' TCACAAACGAAACCATCCTAG 5' | two |

2.4. Promoter/Reporter Gene Constructs

To determine the promoter sequences responsible for regulation of cholesterol 7α-hydroxylase, deletions of the rat CYP7 promoter were ligated upstream of the luciferase reporter gene (Luc). The promoter fragments were generated by the polymerase chain reaction using the primers listed with a rat CYP7 genomic clone as the template. The fragments were blunted by filling in with the Klenow fragment of DNA polymerase and then digested with Xho I. The fragments were then ligated into the pGL2-basic vector (Promega) which had been digested with SmaI and Xho I, and transformed into *E. coli* HB101 cells. The resulting plasmids (pLUC-224, pLUC-160, pLUC-101, and pLUC-3600) are used to transfect primary hepatocytes or hepatoma cells for the study of luciferase gene expression under the control of the CYP7 promoter. The results show that pLUC-224 had two-fold higher luciferase activity than pLUC-160 and pLUC-3600 when transfected into rat primary hepatocytes. pLUC-3600 had transcription activity similar to that of pLUC-160. In addition, 50 μM taurocholate inhibited the expression of luciferase activity in these hepatocytes, indicating that these CYP7 gene promoter fragments do contain BARE, which confers bile acid regulation.

To determine if the sequence from −101 to −29 of the CYP7 gene promoter can function as an enhancer element, the region was cloned into the pGL2-Promoter vector (Promega). The vector is similar to pGL2-basic, with the addition of the SV40 early promoter between the multiple cloning site and the luc gene. The rat sequence was amplified by the polymerase chain reaction to flank the sequence with a BamHI site and a BglII. The fragment was ligated in both orientations to the pGL2-Promoter, which had been cleaved with BglII. The resulting plasmids are named pLUC-101/-29 and pLUC-29/-101.

Chloramphenicol acetyltransferase (CAT) reporter gene constructs were made by using the polymerase chain reaction and primers to amplify the region −415 to +36 of the rat CYP7 gene and to incorporate an XbaI at nucleotide +36. The blunt ended, Xba I digested fragment was ligated into a promoter-less pCAT basic vector (Promega) which had been digested with Sal I, blunt-ended and digested with Xba I to yield −415CAT. A longer construct named −3616CAT was made by digesting −415CAT with Hind III and inserting a 3.2 kb Sac I-Hind III genomic fragment. The 3.6 kb insert was removed from −3616CAT and ligated into a pGL2-basic vector (Promega). This plasmid was used to generate nested deletions with Exo III and S1 nuclease.

It will be apparent to those skilled in the art that various modifications and variations can be made to the compositions of matter and processes of this invention. In particular, various kinds of screening assays are encompassed that employ human CYP7 regulatory elements or its analogs. Thus, it is intended that the present invention cover the modifications and variations provided they fall within the scope of the appended claims and their equivalents.

---

Promoter/Reporter Gene Constructs
    PCR primers used for PCR of fragments
        L1: (SEQ ID NO: 17) 5'-AGATGGCTCGAGACTCTTTGCCTAGCAAA-3'
            XhoI
           −224
        L3: (SEQ ID NO: 18) 5'-CAGCACATGAGGGACAG-3'
           −160
        L4: (SEQ ID NO: 19) 5'-CTCTTCTGAGACTATGGAC-3'
           −101
        L8: (SEQ ID NO: 20) 5'-GAAGATCTAGTAGGAGGACAAATAG-3'
           BglII
    Sequences of promoter fragments inserted in pGL2-basic vector
    pLUC−224: (SEQ ID NO: 21)
        5'-CAGCACATGAGGGACAGACCTTCAGCTTATCGAGTATTGCAGCTCTCTGTTT
          GTTCTGGAGCCTCTTCTGAGACTATGGACTTAGTTCAAGGCCGGGTAATGCTATT
          TTTTTCTTCTTTTTTCTAGTAGGAGGAGGACAAATAGTGTTTGCTTTGGT
          CACTCAAGTTCAAGTTATTGGATCATGGTCCTGTGCACATATAAAGTCTAGTCAGA
          CCCACTGTTTCGGGACAGCCTTGCTTTGCTAGGCAGGCAAAGAGTCTCGAG-3'
            XhoI
    pLUC-160: (SEQ ID NO: 22)
        5'-CTCTTCTGAGACTATGGACTTAGTTCAAGGCCGGGTAATGCTATTTTTTTCT
          TCTTTTTTCTAGTAGGAGGACAAATAGTGTTTGCTTTGGTCACTCAAGTTCA
          AGTTATTGGATCATGGTCCTGTGCACATATAAAGTCTAGTCAGACCCACT
          GTTTCGGGACAGCCTTGCTTTGCTAGGCAGGCAAAGAGTCTCGAG-3'
            XhoI
    pLUC−101: (seq id no: 23)
        5'-GAAGATCTAGTAGGAGGACAAATAGTGTTTGCTTTGGTCACTCAAGTTCA
          AGTTATTGGATCATGGTCCTGTGCACATATAAAGTCTAGTCAGACCCACT
          GTTTCGGGACAGCCTTGCTTTGCTAGGCAGGCAAAGAGTCTCGAG-3'
            XhoI
    pLUC-3600:
        3.6 kb 5' flanking sequence to +36
    Sequences of promoter fragments inserted in pGL2-promoter vector:
    pLuc−101−/−29: (SEQ ID NO: 24)
          −101
        GAAGATCTAGTAGGAGGACAAATAGTGTTTGATTTGGTCACTCAAGTTC
          −29
        AAGTTATTGGATCATGGTCCTGTGCACATCCTAGGGC-3'
    pLuc−29/−101
        Reversed direction of the above sequence
Promoter/CAT gene constructs:
−415CAT:
    sequence from −415 to +36
−3616CAT:
    3.6 kb 5'-upstream sequence to +36

What is claimed is:

1. An isolated regulatory element of the cholesterol 7α-hydroxylase (CYP7) gene which consists of a DNA fragment selected from the group consisting of DNA fragments from about −191 to about +64 of the rat CYP7 gene, from about −252 to about +3 of the hamster CYP7 gene and from about −187 to about +65 of the human CYP7 gene, wherein said DNA fragment is regulatory with respect to CYP7 expression in the presence of bile acids, and wherein the numbering of said DNA fragment is measured relative to the transcription start site.

2. An isolated regulatory element of the rat CYP7 gene which consists of a DNA fragment selected from the group consisting of DNA fragments from about −101 to about −29, from about −81 to about −37, wherein said DNA fragment is regulatory with respect to CYP7 expression in the presence of bile acids, and wherein the numbering of said DNA fragment is measured relative to the transcription start site.

3. An isolated regulatory element of the human CYP7 gene which consists of a DNA fragment selected from the group consisting of DNA fragments from about −104 to about −30, and from about −78 to about −36, wherein said DNA fragment is regulatory with respect to CYP7 expression in the presence of bile acids, and wherein the numbering of said DNA fragment is measured relative to the transcription start site.

4. An isolated regulatory element of the hamster CYP7 gene which consists of a DNA fragment selected from the group consisting of DNA fragments from about −161 to about −86, and from about −136 to about −92, wherein said DNA fragment is regulatory with respect to CYP7 expression in the presence of bile acids, and wherein the numbering of said DNA fragment is measured relative to the transcription start site.

5. A construct comprising at least one regulatory element as defined in claim 3, wherein said regulatory element is operably attached to a structural gene.

6. A construct according to claim 5, wherein said structural gene is a reporter gene.

7. A construct according to claim 6, wherein said structural gene comprises the gene encoding luciferase.

8. A host cell transformed with a vector comprising a construct according to claim 6.

9. A method for detecting a transcription factor of CYP7, comprising the step of contacting a fragment of DNA according to claim 3 with a biological sample suspected of containing a transcription factor and detecting binding between said fragment and a transcription factor.

10. A method for detecting a transcription factor according to claim 9, wherein said binding is detected by performing a footprint analysis.

11. A method according to claim 9 further comprising the step of isolating the transcription factor.

12. A method for determining whether an agent inhibits or stimulates CYP7 gene expression comprising the steps of:
(a) contacting said agent with a transfected cell containing a construct, wherein said construct comprises
(i) human cholesterol 7α-hydroxylase (CYP7) DNA that consists of an isolated regulatory element located within a region from −187 to +65, wherein said element comprises nucleotides −78 to −36 and said element is regulatory with respect to CYP7 expression in the presence of bile acids, and wherein the numbering of said element is measured relative to the transcription start site and
(ii) heterologous DNA, and
(b) determining CYP7 gene expression in said transfected cell.

13. A method according to claim 12, wherein said heterologous DNA is a reporter gene.

14. A method according to claim 12, wherein said agent is a physiological agent endogenous to a human.

15. A method according to claim 12, wherein said agent is an agent exogenous to a human.

16. A method according to claim 12, wherein said regulatory element of human CYP7 is selected from the group consisting of DNA fragments of from about −104 to about −30, and from about −78 to about −36.

* * * * *

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
       ( A ) LENGTH: 32 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:1:

ATCCTCTCCC CACTCCCAAG CATCCCTCCA TG                                    32

( 2 ) INFORMATION FOR SEQ ID NO:2:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:2:

CAACTCCTCC CCTATT                                                      16

( 2 ) INFORMATION FOR SEQ ID NO:3:

( i ) SEQUENCE CHARACTERISTICS:
       ( A ) LENGTH: 44 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:3:

TGTTTGCTTT GGTCACTCAA GTTCAAGTTA TTGGATCATG GTCC                       44

( 2 ) INFORMATION FOR SEQ ID NO:4:

( i ) SEQUENCE CHARACTERISTICS:
       ( A ) LENGTH: 19 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:4:

CTATGGACTT AGTTCAAGG                                                   19

( 2 ) INFORMATION FOR SEQ ID NO:5:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:5:

TGTTCTGGAG CCTCTTCT 18

(2) INFORMATION FOR SEQ ID NO:6:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCACTGTGGC CTAGTGCCAC ATCTACCTAT TTCTTTGGCT TTACTTTGT 49

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TGGTCANNNN AGTTCA 16

(2) INFORMATION FOR SEQ ID NO:8:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

CTAGTAGGAG GACAAATAGT GTTTGCTTTG GTCACTCAAG TTCAAGTTAT TGGATCATGG 60

TCC 63

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

CCTCTTCTGA GACTATGGAC TTAGTTCAAG GCCGG 35

(2) INFORMATION FOR SEQ ID NO:10:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

TCACTGTGGC CTAGTGCCAC ATCTACCTAT TTCTTTGGCT TTACTTTGTG CTAGGTGACC 60

( 2 ) INFORMATION FOR SEQ ID NO:11:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

GAAGATCTAG TAGGAGGACA AATAG 25

( 2 ) INFORMATION FOR SEQ ID NO:12:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:12:

CACTATTTGT CCTCCTAC 18

( 2 ) INFORMATION FOR SEQ ID NO:13:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

GATCCTTGGT CACTCAAGTT C 21

( 2 ) INFORMATION FOR SEQ ID NO:14:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:14:

GATCCTTGAA CTTGAGTGAC CAAG 24

( 2 ) INFORMATION FOR SEQ ID NO:15:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

GATCCAATAG TGTTTGCTTT GGT 23

( 2 ) INFORMATION FOR SEQ ID NO:16:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:16:

GATCCTACCA AAGCAAACAC T                                                              2 1

( 2 ) INFORMATION FOR SEQ ID NO:17:

( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:17:

AGATGGCTCG AGACTCTTTG CCTAGCAAA                                                      2 9

( 2 ) INFORMATION FOR SEQ ID NO:18:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:18:

CAGCACATGA GGGACAG                                                                   1 7

( 2 ) INFORMATION FOR SEQ ID NO:19:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:19:

CTCTTCTGAG ACTATGGAC                                                                 1 9

( 2 ) INFORMATION FOR SEQ ID NO:20:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:20:

GAAGATCTAG TAGGAGGACA AATAG                                                          2 5

( 2 ) INFORMATION FOR SEQ ID NO:21:

( i ) SEQUENCE CHARACTERISTICS:
            ( A ) LENGTH: 264 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

| | | | | | |
|---|---|---|---|---|---|
| CAGCACATGA | GGGACAGACC | TTCAGCTTAT | CGAGTATTGC | AGCTCTCTGT | TTGTTCTGGA | 60
| GCCTCTTCTG | AGACTATGGA | CTTAGTTCAA | GGCCGGGTAA | TGCTATTTTT | TTCTTCTTTT | 120
| TTCTAGTAGG | AGGAGGACAA | ATAGTGTTTG | CTTTGGTCAC | TCAAGTTCAA | GTTATTGGAT | 180
| CATGGTCCTG | TGCACATATA | AAGTCTAGTC | AGACCCACTG | TTTCGGGACA | GCCTTGCTTT | 240
| GCTAGGCAGG | CAAAGAGTCT | CGAG | | | | 264

(2) INFORMATION FOR SEQ ID NO:22:

(i) SEQUENCE CHARACTERISTICS:
   (A) LENGTH: 199 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:22:

| | | | | | |
|---|---|---|---|---|---|
| CTCTTCTGAG | ACTATGGACT | TAGTTCAAGG | CCGGGTAATG | CTATTTTTT | CTTCTTTTT | 60
| CTAGTAGGAG | GACAAATAGT | GTTTGCTTTG | GTCACTCAAG | TTCAAGTTAT | TGGATCATGG | 120
| TCCTGTGCAC | ATATAAAGTC | TAGTCAGACC | CACTGTTTCG | GGACAGCCTT | GCTTTGCTAG | 180
| GCAGGCAAAG | AGTCTCGAG | | | | | 199

(2) INFORMATION FOR SEQ ID NO:23:

(i) SEQUENCE CHARACTERISTICS:
   (A) LENGTH: 145 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:23:

| | | | | | |
|---|---|---|---|---|---|
| GAAGATCTAG | TAGGAGGACA | AATAGTGTTT | GCTTTGGTCA | CTCAAGTTCA | AGTTATTGGA | 60
| TCATGGTCCT | GTGCACATAT | AAAGTCTAGT | CAGACCCACT | GTTTCGGGAC | AGCCTTGCTT | 120
| TGCTAGGCAG | GCAAAGAGTC | TCGAG | | | | 145

(2) INFORMATION FOR SEQ ID NO:24:

(i) SEQUENCE CHARACTERISTICS:
   (A) LENGTH: 86 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:24:

| | | | | | |
|---|---|---|---|---|---|
| GAAGATCTAG | TAGGAGGACA | AATAGTGTTT | GATTGGTCA | CTCAAGTTCA | AGTTATTGGA | 60
| TCATGGTCCT | GTGCACATCC | TAGGGC | | | | 86

(2) INFORMATION FOR SEQ ID NO:25:

(i) SEQUENCE CHARACTERISTICS:
   (A) LENGTH: 255 base pairs (B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:25:

| | | | | | | |
|---|---|---|---|---|---|---|
| GAGTATTGCA | GCTCTCTGTT | TGTTCTGGAG | CCTCTTCTGA | GACTATGGAC | TTAGTTCAAG | 60 |
| GCCGGGTAAT | GCTATTTTTT | TCTTCTTTTT | TCTAGTAGGA | GGACAAATAG | TGTTTGCTTT | 120 |
| GGTCACTCAA | GTTCAAGTTA | TTGGATCATG | GTCCTGTGCA | CATATAAAGT | CTAGTCAGAC | 180 |
| CCACTGTTTC | GGGACAGCCT | TGCTTTGCTA | GGCAAAGAGT | CTCCCCTTTG | GAAATTTTCC | 240 |
| TGCTTTTGCA | AAATG | | | | | 255 |

(2) INFORMATION FOR SEQ ID NO:26:

(i) SEQUENCE CHARACTERISTICS:
(A) LENGTH: 255 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:26:

| | | | | | | |
|---|---|---|---|---|---|---|
| TATCAAGTAT | TGAAGCTCTC | TGCTTGTTTT | GGAGCCTCTT | CTGATACTAT | GGACTTAGTT | 60 |
| CAAGGCTGGG | CAATACTATT | TTTTCTTTT | TTCTAATAGG | AGGACAAATA | GTTAGTTGTT | 120 |
| TGCTTTGGTC | ATCCAAGTTC | AAGTTATTGG | ATCATGGTCC | TATGTGTATA | AAGAGTCTAG | 180 |
| TTTGAGCCTT | TCAGGGGCAG | CCTTGCTGGC | TAAGCACAGA | CTCTCCTCTT | GGGAGTTTTC | 240 |
| CTGCTTTGCA | AAATG | | | | | 255 |

(2) INFORMATION FOR SEQ ID NO:27:

(i) SEQUENCE CHARACTERISTICS:
(A) LENGTH: 254 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:27:

| | | | | | | |
|---|---|---|---|---|---|---|
| GTATTGCAGG | TCTCTGATTG | CTTTGGAACC | ACTTCTGATA | CCTGTGGACT | TAGTTCAAGG | 60 |
| CCAGTTACTA | CCACTTTTTT | TTTTCTAATA | GAATGAACAA | ATGGCTAATT | GTTTGCTTTG | 120 |
| TCAACCAAGC | TCAAGTTAAT | GGATCTGGTA | CTATGTATAT | AAAAAGCCTA | GCTTGAGTCT | 180 |
| CTTTTCAGTG | GCATCCTTCC | CTTTCTAATC | AGAGATTTTC | TTCCTCAGAG | ATTTTGGCCT | 240 |
| AGATTTGCAA | AATG | | | | | 254 |

(2) INFORMATION FOR SEQ ID NO:28:

(i) SEQUENCE CHARACTERISTICS:
(A) LENGTH: 504 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:28:

| Met | Met | Thr | Thr | Ser | Leu | Ile | Trp | Gly | Ile | Ala | Ile | Ala | Ala | Cys | Cys |
|---|---|---|---|---|---|---|---|---|---|---|---|---|---|---|---|
| 1 | | | | 5 | | | | | 10 | | | | | 15 | |

| | | | | | | | | | | | | | | |
|---|---|---|---|---|---|---|---|---|---|---|---|---|---|---|
|Cys|Leu|Trp|Leu 20|Ile|Leu|Gly|Ile|Arg 25|Arg|Arg|Gln|Thr|Gly 30|Glu|Pro|
|Pro|Leu|Glu|Asn 35|Gly|Leu|Ile|Pro 40|Tyr|Leu|Gly|Cys|Ala 45|Leu|Gln|Phe|
|Gly|Ala|Asn|Pro 50|Leu|Glu|Phe 55|Leu|Arg|Ala|Asn|Gln 60|Arg|Lys|His|Gly|
|His 65|Val|Phe|Thr|Cys|Lys 70|Leu|Met|Gly|Lys|Tyr 75|Val|His|Phe|Ile|Thr 80|
|Asn|Pro|Leu|Ser|Tyr 85|His|Lys|Val|Leu|Cys 90|His|Gly|Lys|Tyr|Phe 95|Asp|
|Trp|Lys|Lys|Phe 100|His|Phe|Ala|Thr|Ser 105|Ala|Lys|Ala|Phe|Gly 110|His|Arg|
|Ser|Ile|Asp|Pro 115|Met|Asp|Gly|Asn 120|Thr|Thr|Glu|Asn|Ile 125|Asn|Asp|Thr|
|Phe|Ile|Lys|Thr 130|Leu|Gln|Gly 135|His|Ala|Leu|Asn|Ser 140|Leu|Thr|Glu|Ser|
|Met 145|Met|Glu|Asn|Leu|Gln 150|Arg|Ile|Met|Arg|Pro 155|Pro|Val|Ser|Ser|Asn 160|
|Ser|Lys|Thr|Ala|Ala 165|Trp|Val|Thr|Glu|Gly 170|Met|Tyr|Ser|Phe|Cys 175|Tyr|
|Arg|Val|Met|Phe 180|Glu|Ala|Gly|Tyr|Leu 185|Thr|Ile|Phe|Gly|Arg 190|Asp|Leu|
|Thr|Arg|Arg 195|Asp|Thr|Gln|Lys|Ala 200|His|Ile|Leu|Asn|Asn 205|Leu|Asp|Asn|
|Phe|Lys 210|Gln|Phe|Asp|Lys|Val 215|Phe|Pro|Ala|Leu|Val 220|Ala|Gly|Leu|Pro|
|Ile 225|His|Met|Phe|Arg|Thr 230|Ala|His|Asn|Ala|Arg 235|Glu|Lys|Leu|Ala|Glu 240|
|Ser|Leu|Arg|His|Glu 245|Asn|Leu|Gln|Lys|Arg 250|Glu|Ser|Ile|Ser|Glu 255|Leu|
|Ile|Ser|Leu|Arg 260|Met|Phe|Leu|Asn|Asp 265|Thr|Leu|Ser|Thr|Phe 270|Asp|Asp|
|Leu|Glu|Lys 275|Ala|Lys|Thr|His|Leu 280|Val|Val|Leu|Trp|Ala 285|Ser|Gln|Ala|
|Asn|Thr 290|Ile|Pro|Ala|Thr|Phe 295|Trp|Ser|Leu|Phe|Gln 300|Met|Ile|Arg|Asn|
|Pro 305|Glu|Ala|Met|Lys|Ala 310|Ala|Thr|Glu|Glu|Val 315|Lys|Arg|Thr|Leu|Glu 320|
|Asn|Ala|Gly|Gln|Lys 325|Val|Ser|Leu|Glu|Gly 330|Asn|Pro|Ile|Cys|Leu 335|Ser|
|Gln|Ala|Glu|Leu 340|Asn|Asp|Leu|Pro|Val 345|Leu|Asp|Ser|Ile|Ile 350|Lys|Glu|
|Ser|Leu|Arg 355|Leu|Ser|Ser|Ala|Ser 360|Leu|Asn|Ile|Arg|Thr 365|Ala|Lys|Glu|
|Asp|Phe 370|Thr|Leu|His|Leu|Glu 375|Asp|Gly|Ser|Tyr|Asn 380|Ile|Arg|Lys|Asp|
|Asp 385|Ile|Ile|Ala|Leu|Tyr 390|Pro|Gln|Leu|Met|His 395|Leu|Asp|Pro|Glu|Ile 400|
|Tyr|Pro|Asp|Pro|Leu 405|Thr|Phe|Lys|Tyr|Asp 410|Arg|Tyr|Leu|Asp|Glu 415|Asn|
|Gly|Lys|Thr|Lys 420|Thr|Thr|Phe|Tyr|Cys 425|Asn|Gly|Leu|Lys|Leu 430|Lys|Tyr|
|Tyr|Tyr|Met 435|Pro|Phe|Gly|Ser|Gly 440|Ala|Thr|Ile|Cys|Pro 445|Gly|Arg|Leu|

```
        Phe  Ala  Ile  His  Glu  Ile  Lys  Gln  Phe  Leu  Ile  Leu  Met  Leu  Ser  Tyr
             450                 455                     460

Phe  Glu  Leu  Glu  Leu  Ile  Glu  Gly  Gln  Ala  Lys  Cys  Pro  Pro  Leu  Asp
        465                      470                     475                      480

Gln  Ser  Arg  Ala  Gly  Leu  Gly  Ile  Leu  Pro  Pro  Leu  Asn  Asp  Ile  Glu
                            485                      490                      495

Phe  Lys  Tyr  Lys  Phe  Lys  His  Leu
                       500
```

( 2 ) INFORMATION FOR SEQ ID NO:29:

( i ) SEQUENCE CHARACTERISTICS:
        ( A ) LENGTH: 503 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
        Met  Met  Thr  Ile  Ser  Leu  Ile  Trp  Gly  Ile  Ala  Val  Leu  Val  Ser  Cys
        1                  5                   10                       15

Cys  Ile  Trp  Phe  Ile  Val  Gly  Ile  Arg  Arg  Lys  Ala  Gly  Glu  Pro
                       20                   25                       30

Pro  Leu  Glu  Asn  Gly  Leu  Ile  Pro  Tyr  Leu  Gly  Cys  Ala  Leu  Lys  Phe
                  35                      40                       45

Gly  Ser  Asn  Pro  Leu  Glu  Phe  Leu  Arg  Ala  Asn  Gln  Arg  Lys  His  Gly
             50                      55                       60

His  Val  Phe  Thr  Cys  Lys  Leu  Met  Gly  Lys  Tyr  Val  His  Phe  Ile  Thr
        65                       70                       75                       80

Asn  Ser  Leu  Ser  Tyr  His  Lys  Val  Leu  Cys  His  Gly  Lys  Tyr  Phe  Asp
                            85                       90                       95

Trp  Lys  Lys  Phe  His  Tyr  Thr  Thr  Ser  Ala  Lys  Ala  Phe  Gly  His  Arg
                       100                      105                      110

Ser  Ile  Asp  Pro  Asn  Asp  Gly  Asn  Thr  Thr  Glu  Asn  Ile  Asn  Asn  Thr
                       115                      120                      125

Phe  Thr  Lys  Thr  Leu  Gln  Gly  Asp  Ala  Leu  Cys  Ser  Leu  Ser  Glu  Ala
             130                      135                      140

Met  Met  Gln  Asn  Leu  Gln  Ser  Val  Met  Arg  Pro  Pro  Gly  Leu  Pro  Lys
        145                      150                      155                      160

Ser  Lys  Ser  Asn  Ala  Trp  Val  Thr  Glu  Gly  Met  Tyr  Ala  Phe  Cys  Tyr
                            165                      170                      175

Arg  Val  Met  Phe  Glu  Ala  Gly  Tyr  Leu  Thr  Leu  Phe  Gly  Arg  Asp  Ile
                       180                      185                      190

Ser  Lys  Thr  Asp  Thr  Gln  Lys  Ala  Leu  Ile  Leu  Asn  Asn  Leu  Asp  Asn
             195                      200                      205

Phe  Lys  Gln  Phe  Asp  Gln  Val  Phe  Pro  Ala  Leu  Val  Ala  Gly  Leu  Pro
             210                      215                      220

Ile  His  Leu  Phe  Lys  Thr  Ala  His  Lys  Ala  Arg  Glu  Lys  Leu  Ala  Glu
        225                      230                      235                      240

Gly  Leu  Lys  His  Lys  Asn  Leu  Cys  Val  Arg  Asp  Gln  Val  Ser  Glu  Leu
                            245                      250                      255

Ile  Arg  Leu  Arg  Met  Phe  Leu  Asn  Asp  Thr  Leu  Ser  Thr  Phe  Asp  Asp
                       260                      265                      270

Met  Glu  Lys  Ala  Lys  Thr  His  Leu  Ala  Ile  Leu  Trp  Ala  Ser  Gln  Ala
                  275                      280                      285
```

```
Asn  Thr  Ile  Pro  Ala  Thr  Phe  Trp  Ser  Leu  Phe  Gln  Met  Ile  Arg  Ser
     290                 295                      300

Pro  Glu  Ala  Met  Lys  Ala  Ala  Ser  Glu  Glu  Val  Ser  Gly  Ala  Leu  Gln
305                      310                      315                      320

Ser  Ala  Gly  Gln  Glu  Leu  Ser  Ser  Gly  Gly  Ser  Ala  Ile  Tyr  Leu  Asp
                    325                      330                     335

Gln  Val  Gln  Leu  Asn  Asp  Leu  Pro  Val  Leu  Asp  Ser  Ile  Ile  Lys  Glu
               340                      345                     350

Ala  Leu  Arg  Leu  Ser  Ser  Ala  Ser  Leu  Asn  Ile  Arg  Thr  Ala  Lys  Glu
               355                 360                     365

Asp  Phe  Thr  Leu  His  Leu  Glu  Asp  Gly  Ser  Tyr  Asn  Ile  Arg  Lys  Asp
     370                 375                      380

Asp  Met  Ile  Ala  Leu  Tyr  Pro  Gln  Leu  Met  His  Leu  Asp  Pro  Glu  Ile
385                      390                 395                           400

Tyr  Pro  Asp  Pro  Leu  Thr  Phe  Lys  Tyr  Asp  Arg  Tyr  Leu  Asp  Glu  Ser
                    405                      410                     415

Gly  Lys  Ala  Lys  Thr  Thr  Phe  Tyr  Ser  Asn  Gly  Asn  Lys  Leu  Lys  Cys
               420                      425                     430

Phe  Tyr  Met  Pro  Phe  Gly  Ser  Gly  Ala  Thr  Ile  Cys  Pro  Gly  Arg  Leu
          435                      440                     445

Phe  Ala  Val  Gln  Glu  Ile  Lys  Gln  Phe  Leu  Ile  Leu  Met  Leu  Ser  Cys
     450                      455                      460

Phe  Glu  Leu  Glu  Phe  Val  Glu  Ser  Gln  Val  Lys  Cys  Pro  Pro  Leu  Asp
465                      470                      475                           480

Gln  Ser  Arg  Ala  Gly  Leu  Gly  Ile  Leu  Pro  Pro  Leu  His  Asp  Ile  Glu
                    485                      490                     495

Phe  Lys  Tyr  Lys  Leu  Lys  His
                    500
```

( 2 ) INFORMATION FOR SEQ ID NO:30:

( i ) SEQUENCE CHARACTERISTICS:
        ( A ) LENGTH: 504 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
Met  Met  Thr  Ile  Ser  Leu  Ile  Trp  Gly  Ile  Ala  Met  Val  Val  Cys  Cys
1               5                    10                       15

Cys  Ile  Trp  Val  Ile  Phe  Asp  Arg  Arg  Arg  Lys  Ala  Gly  Glu  Pro
               20                    25                      30

Pro  Leu  Glu  Asn  Gly  Leu  Ile  Pro  Tyr  Leu  Gly  Cys  Ala  Leu  Lys  Phe
               35                    40                      45

Gly  Ser  Asn  Pro  Leu  Glu  Phe  Leu  Arg  Ala  Asn  Gln  Arg  Lys  His  Gly
     50                    55                      60

His  Val  Phe  Thr  Cys  Lys  Leu  Met  Gly  Lys  Tyr  Val  His  Phe  Ile  Thr
65                    70                      75                           80

Asn  Ser  Leu  Ser  Tyr  His  Lys  Val  Leu  Cys  His  Gly  Lys  Tyr  Phe  Asp
                    85                      90                      95

Trp  Lys  Lys  Phe  His  Tyr  Thr  Thr  Ser  Ala  Lys  Ala  Phe  Gly  His  Arg
               100                     105                     110

Ser  Ile  Asp  Pro  Asn  Asp  Gly  Asn  Thr  Thr  Glu  Asn  Ile  Asn  Asn  Thr
          115                     120                     125

Phe  Thr  Lys  Thr  Leu  Gln  Gly  Asp  Ala  Leu  His  Ser  Leu  Ser  Glu  Ala
```

|   |   |   | 130 |   |   |   | 135 |   |   |   | 140 |   |   |   |
|---|---|---|---|---|---|---|---|---|---|---|---|---|---|---|
| Met | Met | Gln | Asn | Leu | Gln | Phe | Val | Leu | Arg | Pro | Pro | Asp | Leu | Pro | Lys |
| 145 |   |   |   |   | 150 |   |   |   |   | 155 |   |   |   |   | 160 |
| Ser | Lys | Ser | Asp | Ala | Trp | Val | Thr | Glu | Gly | Met | Tyr | Ala | Phe | Cys | Tyr |
|   |   |   |   | 165 |   |   |   |   | 170 |   |   |   |   | 175 |   |
| Arg | Val | Met | Phe | Glu | Ala | Gly | Tyr | Leu | Thr | Leu | Phe | Gly | Arg | Asp | Thr |
|   |   |   | 180 |   |   |   |   | 185 |   |   |   |   | 190 |   |   |
| Ser | Lys | Pro | Asp | Thr | Gln | Arg | Val | Leu | Ile | Leu | Asn | Asn | Leu | Asn | Ser |
|   |   | 195 |   |   |   |   | 200 |   |   |   |   | 205 |   |   |   |
| Phe | Lys | Gln | Phe | Asp | Gln | Val | Phe | Pro | Ala | Leu | Val | Ala | Gly | Leu | Pro |
|   | 210 |   |   |   |   | 215 |   |   |   |   | 220 |   |   |   |   |
| Ile | His | Leu | Phe | Lys | Ala | Ala | His | Lys | Ala | Arg | Glu | Gln | Leu | Ala | Glu |
| 225 |   |   |   |   | 230 |   |   |   |   | 235 |   |   |   |   | 240 |
| Gly | Leu | Lys | His | Glu | Asn | Leu | Ser | Val | Arg | Asp | Gln | Val | Ser | Glu | Leu |
|   |   |   |   | 245 |   |   |   |   | 250 |   |   |   |   | 255 |   |
| Ile | Arg | Leu | Arg | Met | Phe | Leu | Asn | Asp | Thr | Leu | Ser | Thr | Phe | Asp | Asp |
|   |   |   | 260 |   |   |   |   | 265 |   |   |   |   | 270 |   |   |
| Met | Glu | Lys | Ala | Lys | Thr | His | Leu | Ala | Ile | Leu | Trp | Ala | Ser | Gln | Ala |
|   |   | 275 |   |   |   |   | 280 |   |   |   |   | 285 |   |   |   |
| Asn | Thr | Ile | Pro | Ala | Thr | Phe | Trp | Ser | Leu | Phe | Gln | Met | Ile | Arg | Ser |
|   | 290 |   |   |   |   | 295 |   |   |   |   | 300 |   |   |   |   |
| Pro | Asp | Ala | Leu | Arg | Ala | Ala | Ser | Glu | Glu | Val | Asn | Gly | Ala | Leu | Gln |
| 305 |   |   |   |   | 310 |   |   |   |   | 315 |   |   |   |   | 320 |
| Ser | Ala | Gly | Gln | Lys | Leu | Ser | Ser | Glu | Gly | Asn | Ala | Ile | Tyr | Leu | Asp |
|   |   |   |   | 325 |   |   |   |   | 330 |   |   |   |   | 335 |   |
| Gln | Ile | Gln | Leu | Asn | Asn | Leu | Pro | Val | Leu | Asp | Ser | Ile | Ile | Lys | Glu |
|   |   |   | 340 |   |   |   |   | 345 |   |   |   |   | 350 |   |   |
| Ala | Leu | Arg | Leu | Ser | Ser | Ala | Ser | Leu | Asn | Ile | Arg | Thr | Ala | Lys | Glu |
|   |   | 355 |   |   |   |   | 360 |   |   |   |   | 365 |   |   |   |
| Asp | Phe | Thr | Leu | His | Leu | Glu | Asp | Gly | Ser | Tyr | Asn | Ile | Arg | Lys | Asp |
|   | 370 |   |   |   |   | 375 |   |   |   |   | 380 |   |   |   |   |
| Asp | Ile | Ile | Ala | Leu | Tyr | Pro | Gln | Leu | Met | His | Leu | Asp | Pro | Ala | Ile |
| 385 |   |   |   |   | 390 |   |   |   |   | 395 |   |   |   |   | 400 |
| Tyr | Pro | Asp | Pro | Leu | Thr | Phe | Lys | Tyr | Asp | Arg | Tyr | Leu | Asp | Glu | Asn |
|   |   |   |   | 405 |   |   |   |   | 410 |   |   |   |   | 415 |   |
| Lys | Lys | Ala | Lys | Thr | Ser | Phe | Tyr | Ser | Asn | Gly | Asn | Lys | Leu | Lys | Tyr |
|   |   |   | 420 |   |   |   |   | 425 |   |   |   |   | 430 |   |   |
| Phe | Tyr | Met | Pro | Phe | Gly | Ser | Gly | Ala | Thr | Ile | Cys | Pro | Gly | Arg | Leu |
|   |   | 435 |   |   |   |   | 440 |   |   |   |   | 445 |   |   |   |
| Phe | Ala | Val | Gln | Glu | Ile | Lys | Gln | Phe | Leu | Ile | Leu | Met | Leu | Ser | Tyr |
|   | 450 |   |   |   |   | 455 |   |   |   |   | 460 |   |   |   |   |
| Phe | Glu | Leu | Glu | Leu | Val | Glu | Ser | His | Val | Lys | Cys | Pro | Pro | Leu | Asp |
| 465 |   |   |   |   | 470 |   |   |   |   | 475 |   |   |   |   | 480 |
| Gln | Ser | Arg | Ala | Gly | Leu | Gly | Ile | Leu | Pro | Pro | Leu | Asn | Asp | Ile | Glu |
|   |   |   |   | 485 |   |   |   |   | 490 |   |   |   |   | 495 |   |
| Phe | Lys | Tyr | Lys | Leu | Lys | His | Leu |   |   |   |   |   |   |   |   |
|   |   |   | 500 |   |   |   |   |   |   |   |   |   |   |   |   |

( 2 ) INFORMATION FOR SEQ ID NO:31:

( i ) SEQUENCE CHARACTERISTICS:
        ( A ) LENGTH: 7970 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

| | | | | | | |
|---|---|---|---|---|---|---|
| GAGCTCTACC | CTTGCTCTGC | TATTTGTACT | TTTTAATACA | CAGTTCAATC | AAATGTGCCA | 60 |
| CCAGAAATAT | GCATGCTAAC | AGCTGTAGGT | GGTTTGATTT | TTCTTTCTAC | TCTTCTGTGT | 120 |
| GTAAGACCCC | ATGTTTATC | AATTATTTTT | TAATGATTTC | TTTCTTCATG | CCATATGTGT | 180 |
| GGCCGTCAGT | GTGCACAGTC | TGTGTGTACA | GCAGGTGTCA | CAGGTATCCA | CAGAGGTTCC | 240 |
| AGAGGTTCCC | TGTAACTAGA | ATTACAGGCA | CTTGTAACTT | TCCTGTATGG | GTGCTGGGAA | 300 |
| GCAATCTGAG | GTCTCTGCAA | GGGATCTTAA | CCTCAGACTT | CTAGCCTGC | TTTGCCCATT | 360 |
| TCTATTTATG | ATGACTGGAA | ACTGGGCTTA | GGCCTTATAT | TCTCTGAGGC | CAAAATCAAG | 420 |
| TTCTTCCAAA | CTGCAGGATT | TATGGTCTTC | TATAGTATCC | CACAGAAATG | GAAAGAAAG | 480 |
| TGACCCATTA | GAGCAGTATT | AGAGTCGAAA | TAAACTCAAC | TTGGTATGCC | AGGACTTTGG | 540 |
| ACAATAATAA | CCCTGTCTTT | TCAGGGCATC | TTATCTGTAC | TGCTGCAATA | GAAACTCCAC | 600 |
| AGGTCAGGGT | CACAGCTGTT | GTGTTTACA | AGCTGTCCCC | AGGATTAGTT | CAGTGCCCAC | 660 |
| CATGCAATAG | GTGTCATGGT | GTGTGTGTGT | GTGTGTGTGC | GTGTGTCGTG | CTTGTGTGCA | 720 |
| TGTGTGTGAG | ACACACACAC | AGAGAGATAC | AAAGACAGAA | ACAGAAAATT | AATAAAAATT | 780 |
| TTACCAACTA | AAATAGGGAA | TTAAAGAAAA | GGAGGAGAAA | AAGTTGGGCA | TTCAACACCA | 840 |
| TAAAGTCCCA | GTACTATGCT | AAGAACACCC | AGCTGTCCTC | ACACCCGGGC | ATGAAACTTC | 900 |
| ATGCACTGTT | CATCAGAAAA | TCGTTTACAC | ACATCCCCTT | GCAGTCTACT | TGTAGTTTTA | 960 |
| ACAACTTCAG | AGAGCACTAG | CATTTCCAGC | CCCAGGGTTA | GAAGCTTTGG | TAGATGCTGT | 1020 |
| TTGCGAGCAC | AGGATAGCAG | CAAGAAGTGG | ACTTGTTAGA | AGGGAAAAGC | CAATGCCTAT | 1080 |
| GTAACAACGA | AAACTAAGTA | TGAATCTCGA | ATCATCCACT | CTCGTGTGTC | TGTGTCTCCA | 1140 |
| TATACGTGCT | TGGGTGCCTG | ACATGGCAAG | GTGTTACAAG | TAAGGGAGGA | ACAAGAAAAG | 1200 |
| GACAGGGTAG | TGGACATCAG | GATGAATGCC | AGCCAGGGCG | ACTGGAGAGA | GTCTACGCTG | 1260 |
| CTCTGAAGGT | GGGTGAAGAA | GACCTCAGGA | AGCTTTCTGA | GGCTCCGAGA | GTGCTTTTCC | 1320 |
| CTTCCCATGT | TGAAACATCC | TTATTTGCAG | AGAATTCCAG | GTTCATGGGA | ATTTGTAAAG | 1380 |
| AGAATACTAA | GAGGCCACCT | CGTTGTCTCC | TATTTTTGTC | TGCTGTCATT | TATGGGACAG | 1440 |
| GGTTAGAGAC | CTGGCTTGCT | TGGCTATGAG | GCTGTTGCTT | CCTCGGTTAC | TCTGCTGTGG | 1500 |
| TTGGATGCAT | TAGGGTTAGG | CCCCTCAAGA | GCCATGTGTC | ATTTTATAAA | AGCAATATAA | 1560 |
| ATATACTTAA | GGTGCACAAA | GCATTAGGAG | GTCTGAGATA | ATAGATTCTG | AGAAAATCTA | 1620 |
| TCCTGCTGTG | TAGCAACTGA | TGTTTATGAT | TATAGTCCCA | GACCACACGA | TAAAGGATCT | 1680 |
| GTGGGCTCTG | TTTAGGGAGG | TCAAAAAACT | ATTGCAAATG | GAGTCTATAG | AGAAAACTAG | 1740 |
| ACAGGACTCA | ATGCTCACCA | ATCGAGAATT | AGTTGATGAG | CTGGGGTAGT | GACTTAGTGG | 1800 |
| ATAAGAACAC | GGTCCTTTCA | GAGGTCCTGA | GTTAAATCCC | CAGCAAACAC | ATGGTGGCTC | 1860 |
| ATAACCATCT | ATATTGTGAT | TGATGCCCT | CTTCTGGCAT | GCAGGTGTAC | ATGCAGACTC | 1920 |
| GTATACATAA | AATAAATAAA | TCTTGAAAAA | ATGAATACGT | TGAATAAGTG | TCCCCTCGGA | 1980 |
| TAACTTTCTG | CAGAATTTTA | AGCACATGTC | AATGGTAATA | ACACACACAC | ACACACACAC | 2040 |
| ACACACACAC | ACACACACAC | ACATACACAC | ACCATACAGA | TATGTATCTA | GAGACATACA | 2100 |
| CATGTACATT | TTATCTCTTT | TATTTCTTC | TCCCCTCTTT | GACATCAAGG | AATAGAATGC | 2160 |
| ACTCACTGTG | GCCTAGTGCC | ACACTCTACC | TATTTCTTTG | GCTTTACTTT | GTGCTAGGTG | 2220 |
| ACCCGAAAGG | GTTTAAATAT | CAAAAATGCT | AATGGCTCGA | CATTTACATC | CCCAATTTCT | 2280 |

| | | | | | |
|---|---|---|---|---|---|
| CCTTTCTCCT | TACCTCAGAC | TCTTACATTC | AGTTGACAAT | TTGACATCGT | CTCCTGGATT | 2340
| TTCAAATGTT | CAGCACACTG | TACTGATGTA | CTGCCTTCCA | AGGCAACCGG | CACGATCCTC | 2400
| TCCCCACTCC | CAAGCATCCC | TCCATGAGCC | AGTGTTGCT | TATCTTCTTG | ACTCTTGTTT | 2460
| TAACCCAACT | CCTCCCCTAT | TCACTCTGCT | CTAATTCATT | CATTCTATAT | TTTCGCACAT | 2520
| CAGGCTCATC | CTTTGCTCAG | GAACTTCACT | TTTGCTTTCC | GGTCTCCTGG | AAATGTGTTT | 2580
| TCCTATCAAC | ATATTTAAAG | CCCTCTTCAT | CCCCAGTAGC | TCTGGACACC | TCATTTTATG | 2640
| GATACACAAC | ACATATTTGC | CACCTGTCTC | CCCATTAAAA | TATAATCTTC | AGTAGAGAAA | 2700
| CTCCATATCT | TGTTAATACC | TGAAACAAGA | ATATCTTCAA | AGAGTTCCTG | GACATAAAA | 2760
| ACGCTCAATT | AATATTTATG | TTAAACAGGG | ATCTGGGGTA | TATCACAGAG | GTAGAGGGCT | 2820
| TACCTAGGAG | GAGTTGGGCC | ATGGGTTCAA | CTTCCAGCAC | AGAATGAAAG | ATTATGTTAA | 2880
| ATAAAGTTGG | GAAGGATGTA | TGCCAGTCTA | TGAGTAGTAT | AGGAGGTAAA | TTATGAATTC | 2940
| ATATTTACTT | TTCGGACAAG | AAGTGTTGTA | GTCTTTATTT | GAAATAAAAT | ACATCTTAAT | 3000
| TACCAATAAC | AATTGGTAAG | GAGTGAATTC | TCAAGCTGTG | GCTTCCTGGT | AGATGAGTCC | 3060
| TGGGAGGTTT | TCTATTTCGA | TGATGGTAGA | TAGGTAACCT | GTCATATACC | ACATGAAATA | 3120
| CCTGTGGCTT | TGTAAACACA | CCGAGCAGTC | AAGCAGGAGA | ATAGTTCCAT | ACAGTTCGCG | 3180
| TCCCTTAGGA | TTGGTTTCGG | GATACTTCTG | GAGGTTCATT | TAAATAATTT | TCCCCGAAGT | 3240
| ACATTATGGG | CAGCCAGTGT | TGTGATGGGA | AGCTTCTGCC | TGTTTTGCTT | TGCGTCGTGC | 3300
| TCCACACCTT | TGACAGATGT | GCTCTCATCT | GTTTACTTCT | TTTTCTACAC | ACAGAGCACA | 3360
| GCATTAGCTG | CTGTCCCGGC | TTTGGATGTT | ATGTCAGCAC | ATGAGGGACA | GACCTTCAGC | 3420
| TTATCGAGTA | TTGCAGCTCT | CTGTTTGTTC | TGGAGCCTCT | TCTGAGACTA | TGGACTTAGT | 3480
| TCAAGGCCGG | GTAATGCTAT | TTTTTTCTTC | TTTTTTCTAG | TAGGAGGACA | AATAGTGTTT | 3540
| GCTTTGGTCA | CTCAAGTTCA | AGTTATTGGA | TCATGGTCCT | GTGCACATAT | AAAGTCTAGT | 3600
| CAGACCCACT | GTTTCGGGAC | AGCCTTGCTT | TGCTAGGCAA | AGAGTCTCCC | CTTTGGAAAT | 3660
| TTTCCTGCTT | TTGCAAAATG | ATGACTATTT | CTTTGATTTG | GGAATTGCC | GTGTTGGTGA | 3720
| GCTGTTGCAT | ATGGTTTATT | GTTGGAATAA | GGAGAAGGTA | TGGAAAGATT | TTTAAAAATT | 3780
| TGTCTTTTAG | CTTATTTCTA | GTATTCATTG | CCTTCACTAT | TATGTAGTGC | AAAAAATACT | 3840
| AATGCATTAA | TATTTTTAAA | TTTAAAATTT | AAAGACGTAC | TTCTTTGACT | AAATCTAGTA | 3900
| AGATGTAGAG | AGTCCCCCTT | GGAACATTCA | CATATGCCAC | TGGTAATGCA | GATCTTGTGA | 3960
| AATATAACTA | AAGAAATCAC | AAGTCATCGA | TGTAAGTTTG | TGTCTGCATG | GGCGGAACAA | 4020
| ACCTAAGCTA | AGAAGAGTAG | TATTTGGGAG | GGATCTTTCT | GTGACATGAA | CTGAATAGAC | 4080
| GCACTGCCTC | AGCAAACACA | CATTCATTTG | AATTTTCCTC | AGACTCAGTC | TAAGCCTGGT | 4140
| GAGAGCACCA | AGTGTGAGTC | TGTCTGCCAC | TAACGTTTCC | TTCCAGTGGT | AATCAGCTGT | 4200
| GTGGCTGTGA | AACCTTGGCG | CCTGCACATG | ACAGCCATTT | GAATAGTTCA | AGAACATTT | 4260
| AGGGACAGGA | TATTAAGATA | TTTTCTGTGA | TGTCAACATC | AAAATAGGAG | AATGCCCCTG | 4320
| GCATTATCTT | CAGAGAGGTA | GACTACTGTG | CGTTGTCTTA | CTTTAAAGAA | ATTTCTTTGC | 4380
| CCCTTTGGCT | ATTTTAATTC | AAACCTGAAA | GTTTTCAGTT | TTAATTAAAC | TGTTGATTTT | 4440
| CATGCTAGGA | AAGGAAATAT | CAATTATACT | TAATTGTTCT | TACAAGAAAT | AAAATCATTT | 4500
| ATGTCGGGAG | ATAAATAAGC | TCATAATTTT | AATAAAACAT | TTAAGAGAGA | GAAAAGAGT | 4560
| AGTGGATTAT | AGTTCATTGT | CTGTCAATGT | TTACCTGACC | CAGTTTCATT | TTATAATTAT | 4620
| CTAATTTTTC | AAATGAGATT | CCTGTTCTTT | CCAAATATCA | TTGCAGAATA | CTAACATTCT | 4680

```
TTTTTTCAGA  GTTGAGAATC  AAATGGAGGG  TTTTTTCATC  CTGGCACAAG  CTCCGCTCTT   4740
CAGTAACACC  TCCAGCCCTC  AGAATGCCAA  TATTTTAAAT  TATGTAGGTT  GTTAAAACTT   4800
TAGTGCTGGG  GCTGGGGATT  TAGCTCAGTG  GTAGAGCACT  TGCCTAGCAA  GCGCAAGGCC   4860
CTGGGTTCGG  TCCCCAGCTC  TGAAAAAAAG  AAAAAGAAAA  AAAAAAACTT  TAGTGCTGTA   4920
GCCCTTTCTG  TTATTTGATG  TTTCACATCT  GTTAAAAAAC  AAAACAAAAC  AAAAAAACA   4980
AGCAAATGGA  ACATTTTAGG  CATTCTTTGG  GGGAAATGAT  TCTTAGAGCA  AGTCTAATCA   5040
TTAGGTGATA  GTTTCATTTT  TACACCAAGA  ACAAGAATCT  TGTTGGCTGT  GTTAACACTT   5100
TAAGCCCTGT  TGTAGGGAAA  AAGCAATCAG  ACACAGGCAC  AGAAAAGAAT  TTGGATGAGT   5160
ACTTGATGAT  GTATGTATAT  ATGGTGAATA  GACTGATGGG  TGGGCTGCTG  GCTGGGTTGG   5220
TAAGTGGGTA  GATTTTTTTT  TAAAGATTTA  TTCATTTATT  ATATATCAGT  ACACTGTAGC   5280
TATCTTCAGA  TACACCAGAA  GGGCATCGGA  TCTCTTTACA  GATGGTTGTG  AGCCACCATG   5340
TTTTCCTAAC  CTCTCAAGTC  TCTGTCTTCC  AGGAAAGCTG  GTGAACCTCC  TTTGGAGAAC   5400
GGGTTGATTC  CGTACCTGGG  CTGTGCTCTG  AAATTTGGAT  CTAATCCTCT  TGAGTTCCTA   5460
AGAGCTAATC  AAAGGAAGCA  TGGTCACGTT  TTTACCTGCA  AACTGATGGG  GAAATATGTC   5520
CATTTCATCA  CAAACTCCCT  GTCATACCAC  AAAGTCTTAT  GTCATGGAAA  ATATTTTGAC   5580
TGGAAAAAAT  TCATTACAC   TACTTCTGCG  AAGGTAATTA  ATTCGTTATA  CAGATTCTGT   5640
TTGTTTCCTG  GTCTGTTGAT  GTATTAGTGT  ATTTAGTTGT  TCCAATTTTG  TTAGGTTGCA   5700
GAATAGAGGT  AACATAAAAT  CAGGGCGTTT  CTTAGTAATA  AGCATTAGAC  ATTTAAGGCA   5760
GATGTAAACC  TGTCATTGAT  GATTCCGGAG  ACAGAGGACA  CTGCAGGAAT  CAGGAAGGTA   5820
CAGATTCATA  GCACCACTCG  TCCCTTAACA  ACACCCTGAG  CAGGGTGTTG  GCACTCTTAG   5880
CCTTCAGTCC  TTGTACACAC  GTTTCATTCC  TAAGATATAG  GCTGTATATT  TAAACACGAT   5940
TTGGAAGCCA  TCAAGAATCT  GTTCTAGAGA  AAACAGCATT  TAATGATCTT  TTGCAAGAAA   6000
ATATCAGTTA  TAGTCTCTGT  CATTAAGTAC  ATTGTAATCT  GGTTAAAGAG  TATCTACTAA   6060
GAAAGTAAAG  GCAGATTAGA  ACAATACCAA  TGGATGATGG  GCCATCCAGA  GAAATCCTAC   6120
TGTAAATGCT  GGGATTTAAA  CTTGACCCCA  AGGAAGAGTA  TGACTTGATT  CTACCTTTGG   6180
AATGTGCTGT  AAAATCATAT  TAGGGAAGGT  TCCAGACAGA  GAAGTGGGAT  GTATTTAATC   6240
TATCTTCCAG  CCCACTCTCT  AACACTAGCT  AGCTTTGGGC  TTTAGACCCT  CCCCATTTCA   6300
TGGATTCTAT  TTTCTACCAG  GCATTTGGAC  ACAGAAGCAT  TGACCCAAAT  GATGGAAATA   6360
CCACGGAAAA  TATAAACAAC  ACTTTTACCA  AAACCCTCCA  GGGAGATGCT  CTGTGTTCAC   6420
TTTCTGAAGC  CATGATGCAA  AACCTCCAAT  CTGTCATGAG  ACCTCCTGGC  CTTCCTAAAT   6480
CAAAGAGCAA  TGCCTGGGTC  ACGGAAGGGA  TGTATGCCTT  CTGTTACCGA  GTGATGTTTG   6540
AAGCCGGCTA  TCTAACACTG  TTTGGCAGAG  ATATTTCAAA  GACAGACACA  CAAAAAGCAC   6600
TTATTCTAAA  CAACCTTGAC  AACTTCAAAC  AATTTGACCA  AGTCTTTCCG  GCACTGGTGG   6660
CAGGCCTTCC  TATTCACTTG  TTCAAGACCG  CACATAAAGC  TCGGGAAAAG  CTGGCTGAGG   6720
GATTGAAGCA  CAAGAACCTG  TGTGTGAGGG  ACCAGGTCTC  TGAACTGATC  CGTCTACGTA   6780
TGTTTCTCAA  TGACACGCTC  TCCACCTTTG  ACGACATGGA  GAAGGCCAAG  ACGCACCTCG   6840
CTATCCTCTG  GCATCTCAA   GCAAACACCA  TTCCTGCAAC  CTTTTGGAGC  TTATTTCAAA   6900
TGATCAGGTA  ACTTTCCAGT  GACAGAAATT  GCATTTTAAA  CTCAAAACCC  AAAAAGACTT   6960
ATAGAGCTTT  CTGTGCTATC  AACAAAGAAA  GTAATACTCA  ATGTCCGTGT  TTAGCATGTG   7020
CGTAACAGAA  GCAGCAATTT  TTAGGTGCAC  AGTCCCATCG  AAAGGGATGT  CCCAGAAGCC   7080
```

| | | | | | |
|---|---|---|---|---|---|
| ACAGAACTCA | GACAGGTTGG | TGCTCCATTA | GTACAGGTTC | CCTGGCCTAG | TCTTGCTCCT | 7140 |
| CACCCGATAT | GTTCCTCTTA | ATATCAAATT | AAATCCCCGA | GTGCAGTCGT | CACCACCATA | 7200 |
| TAAACATTTG | AAATGATGAC | TGACTTGCAG | GTGTGATAAG | AGCAGTGACC | ATACCTTACT | 7260 |
| AATTCACTGG | AATTCATAGG | CAAAGTAACA | CCATCGATTT | TGTATTCATA | TAGGAGCTGC | 7320 |
| AGCCATATTT | TAAATAGCAC | AACTACTTGT | TAGTCAAGCA | TTCTGAGGCT | CACTGTAATC | 7380 |
| AGGTAAAGTA | GGTTTAACTC | AGCGTCCTAC | CAGTTCCAGG | CATTGAAATG | GAATATCCTT | 7440 |
| TATCCCACCC | ATTCAAAACG | TAATATATAA | ATGGAAGGCA | CAGTTTTGAA | GGCCATGGTA | 7500 |
| TGATTTAGGG | AATTTACTCT | CATGGTCCAA | TCCCTTGTAA | TTGTATGCTA | GGTGACATAT | 7560 |
| CCTTCTGACT | TACTATGTTC | ATCGTATATT | CAATCCTTAG | TTTATAGAGA | CTGACCAAAG | 7620 |
| CTCTGCTTTT | GCATAGCAAA | GCTCCTTTTA | ATGCCCATTC | CTAAACTCAA | GGACACGAAT | 7680 |
| CCAGTTCAGT | GCCCTTTTGC | ATACTCCCTG | GCAGACTCCC | GTTGCCATAC | ATCCTCCCTC | 7740 |
| GCTCGATTCC | CATGACCTCG | CCCTTGCACA | CCCTGGTACT | AGGACCTCTC | CTGGCGATAC | 7800 |
| TTCCTACTAC | CTATGCCACC | TCATTAAAAG | GAAGGGATAA | TTGCTATTTA | CTTGCAGTTC | 7860 |
| TCTGAATGAG | GACATTTCC | CCATACGGCT | CTTTCCACAG | GAGTCCTGAA | GCAATGAAAG | 7920 |
| CAGCCTCTGA | AGAAGTGAGT | GGAGCTTTAC | AGAGTGCTGG | CCAAGAGCTC | | 7970 |

( 2 ) INFORMATION FOR SEQ ID NO:32:

( i ) SEQUENCE CHARACTERISTICS:
        ( A ) LENGTH: 5537 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

| | | | | | |
|---|---|---|---|---|---|
| TTTTGGTTA | TCTTTTCAGC | CGTGCCCCAC | TCTACTGGTA | CCAGTTTACT | GTATTAGTCG | 60 |
| ATTTTCATGC | TGCTGATAAA | GACATACCTG | AAACTGGACA | ATTTACAAAA | GAAAGAGGTT | 120 |
| TATTGGACTT | ACAATTCTAC | ATCACTTGGG | AGGCCTCACA | ATCATGATGG | AAGGAGAAAG | 180 |
| GCACATCTCA | CATGGCAGCA | GACAAGAAAA | GAGCTTGTGC | AGGGAAACTC | CTCTTTTTAA | 240 |
| AACCATCAGA | TCTCATGAAA | TTTATTCATT | ATCATGACAA | TAGCACAGGA | AAGAACTGCA | 300 |
| CCCATAATTC | AGTCACCTCC | TACCAGGTTC | CTCCCACAAC | ACGTGAGAAT | TCAAGATGAG | 360 |
| ATTTGGATGG | GGACACAGCC | AAACCATGTC | ACACTACCAT | GCCTGACTTC | CTTTCCATTT | 420 |
| TTGTATATTT | GCTTGTTCTT | CATTTGCCCG | AGAAGTAACT | CTAAAGGGCT | GTATTATTTG | 480 |
| GATATTAGAT | TGGCATTTTA | TCTGACTGGG | ATATCTTGCT | GTGATTGTCC | ATGTATAAGA | 540 |
| TCAGCTTTTC | TATAAGCCAT | ATTTTTAAAA | AGATATATTA | ATTTTTTAAA | AATCCACCTG | 600 |
| TCTAAATAAA | TGCACAAAGC | CCCCCAAAAA | CCTAGATTCT | AAGAAAAATC | TATGTACTGC | 660 |
| CATACAATGA | TTGATATTAA | TATTTATGGT | GATAAATTAC | ACACAAAAAA | TGTGTGATCT | 720 |
| CTGTTTAAAC | AGGCAAAAAC | AAAAAACACA | TGAAATAAAT | CTATGGCATC | TATAGCCAAA | 780 |
| ACTGGAAACA | ACCCACATAT | CCATCAATAG | GAAATCAGTT | AAATAAATTA | TAGTACATTT | 840 |
| ATCCAATGGA | AGATTAAGCA | CATATTCAAT | ATAATTATTT | ATACACACAT | ATAGATACAC | 900 |
| ACATGTATAA | ATATAGAGAA | TACTGTGGGT | GTATGTGTGT | GTGTGTTTAT | ATACATATAT | 960 |
| ATACACACAC | AGTACTGTTG | CCTACCTTCT | TTTGTCTTAA | TTCTGTGAAC | TCTCATTCAC | 1020 |
| TCTGCTTCAG | TAGGATACCT | CCTTCTTTTT | GGTTCTTAGA | CTCACCAAGT | TGATCCTTGA | 1080 |
| CTCAAGACAT | TGCATTTGCT | GCTTCCTCTT | CCTGGAATAT | CCTTCCTTCT | GATATTCACA | 1140 |

| | | | | | |
|---|---|---|---|---|---|
| TGAGTAGTCT | CTTCTTGTCA | TTCAGATCTC | AAATGTCACA | ATTTCAGAGA | GCCCATCTCT | 1200 |
| GATCATCATA | TCTAAAGTTG | TCCTCATTCC | CCCATAGCTT | TCTATACCAT | GTTTTATTTT | 1260 |
| TTTCATAACA | TGTATTTTAT | TACTCCTTTC | TCCATTGGAA | TAGAATCTCC | ATTAGATTAG | 1320 |
| GAAATCTGCC | TATCTTATTA | ATGCCTGCAA | CTGGAATACT | TTTGAAGAGT | CTTGGCACG | 1380 |
| TAATAAATAC | TCAACTAATA | TTTTTGTGTA | CACAGAAATA | AAGTTTGGAA | GAACAGATGC | 1440 |
| CAAATTGTTA | CTAGTGGTTA | CTTCTGAGTA | AAGGAGTAGC | ATGGTAGGTA | AATTATTAAT | 1500 |
| AGATGTTCAC | TTTCCACCAA | GATATGTTTT | AGTTAGTCTT | AACTTACTTG | AAATGAAATT | 1560 |
| TATTACTTTA | ATAATTAGAA | ACATTGATAA | ACATTTAGT | CACAAGAATG | ATAGATAAAA | 1620 |
| TTTTGATGCT | TCCAATAAGT | TATATTTATC | TAGAGGATGC | ACTTATGTAG | AATACTCTCT | 1680 |
| TGAGGATGTT | AGGTGAGTAA | CATGTTACTA | TATGTAGTAA | AATATCTATG | ATTTTATAAA | 1740 |
| AGCACTGAAA | CATGAAGCAG | CAGAAATGTT | TTTCCCAGTT | CTCTTTCCTC | TGAACTTGAT | 1800 |
| CACCGTCTCT | CTGGCAAAGC | ACCTAAATTA | ATTCTTCTTT | AAAAGTTAAC | AAGACCAAAT | 1860 |
| TATAAGCTTG | ATGAATAACT | CATTCTTATC | TTTCTTTAAA | TGATTATAGT | TTATGTATTT | 1920 |
| ATTAGCTATG | CCCATCTTAA | ACAGGTTTAT | TTGTTCTTTT | TACACATACC | AAACTCTTAA | 1980 |
| TATTAGCTGT | TGTCCCCAGG | TCCGAATGTT | AAGTCAACAT | ATATTTGAGA | GACCTTCAAC | 2040 |
| TTATCAAGTA | TTGCAGGTCT | CTGATTGCTT | TGGAACCACT | TCTGATACCT | GTGGACTTAG | 2100 |
| TTCAAGGCCA | GTTACTACCA | CTTTTTTTTT | TCTAATAGAA | TGAACAAATG | GCTAATTGTT | 2160 |
| TGCTTTGTCA | ACCAAGCTCA | AGTTAATGGA | TCTGGATACT | ATGTATATAA | AAAGCCTAGC | 2220 |
| TTGAGTCTCT | TTTCAGTGGC | ATCCTTCCCT | TTCTAATCAG | AGATTTTCTT | CCTCAGAGAT | 2280 |
| TTTGGCCTAG | ATTTGCAAAA | TGATGACCAC | ATCTTTGATT | TGGGGATTG | CTATAGCAGC | 2340 |
| ATGCTGTTGT | CTATGGCTTA | TTCTTGGAAT | TAGGAGAAGG | TAAGTAATGT | TTTATCTTTA | 2400 |
| AATTGCTCTT | TGATTCATCC | ATTTAATTTT | TTTACCTTCA | TTTTTATACA | GTAAATTTGG | 2460 |
| TTTTCTATAC | TTACACATAT | TAGCATTATC | TTCCTTATGT | TTTAAATGAA | AAATTTGATT | 2520 |
| TGAATTTTTA | AAGTAATATC | TTTTTTACTA | TATCTCACAA | GACATATGAC | AGCTTCCCTT | 2580 |
| TTAGTATTG | GCATATACCG | ATGGTAATAT | ATAAATGTAT | ATTGGTGTTA | AACATAACTG | 2640 |
| ACAGAAATTG | TATAAGGTCT | CTATGTACAT | TTATATGTGT | ATCTAAAGAG | GAAGCCCAGA | 2700 |
| TTAGTAAGGA | TACAAGTAGC | AAGTGGGAAT | CTACAATGGA | AAGGATTGCT | TTCTCTCACA | 2760 |
| TGGCTTCAAT | AGATACTCTT | GCTTAAATAA | ATGTTCTCTT | TTAAGCTCAT | TCTTGTGCAT | 2820 |
| CGCATAGACT | CAGCCTAAGC | CTGAACAAGA | GCATAGAGCC | TGAGCTGATC | ATTCTATTAC | 2880 |
| TGTTTTAAA | TAAATGTTAA | TCAACTGTGG | TGAATTGGGA | AAGTTTGCTG | AGTGTATGTG | 2940 |
| ACATCGATTT | CATTTATTTA | CAACTGGTTC | AAGAATGCAA | GAAAACAAA | TACAGTCAGA | 3000 |
| TCCAGAACCA | TAGTTTATTT | AACTTCTAAT | TGGCTCAAGG | AGTAATTGTG | GGGAGGCATA | 3060 |
| TAGATATTCT | CTGCTATGTC | AATCTCAAAA | AGAGAAAATA | ACCCTAACCA | TCTTTCAGCT | 3120 |
| TTGTAGATTG | CTATGTGTTT | TCTGCCTTTG | CAGTTTCTTT | CAGGCCTGAT | AGTTTTACT | 3180 |
| TTTAATTAAA | CTACTTATCT | TCAAACTAAG | AAAAGAAAGG | TAATTACTTT | ATACTGTATT | 3240 |
| ATTCTATCAA | GAGGTACAGA | AGTTTATGTT | GGAAAATAAG | TTTACATGTT | CTAATAAAAA | 3300 |
| CATTTAAAG | GAGCACTGAA | TTACAATAGA | TGATTCCGTC | AGTGTTTATC | TTACTCAATT | 3360 |
| TCATTTTATA | ATAAGCTGAT | TTCTCACATG | AGATTCTTCT | TCTCTGAAAC | CATCCTTATA | 3420 |
| GAATATAATA | TAGATATCTT | TAAACTAGGA | ATATTTTCAA | AACCTCAGTT | CTGAAATCCT | 3480 |
| CCCTTATTCA | GTGATCTGTG | TCTTTAAAGA | AAATAATCAA | AAGAAACATT | TTGAGATATT | 3540 |

-continued

| | | | | | |
|---|---|---|---|---|---|
| TAGAAAAATG | ATGCTTAGCA | AAGTGATAAA | CACTAGAATG | TAGTTTTGTT | TCCGCACTGA 3600 |
| CAACAAGAAT | CTTGTTGGTC | TTGTAAATCC | TTTTGCCTGT | ATCACTGGGA | AAAGTGATGA 3660 |
| GCACATAGTA | GACGGGTGCT | TGTTGAATGT | GTATATGGAC | GGATGCATGA | ATGGATGGAT 3720 |
| TTAGTAATCC | TTTCCACCAA | CATATCATGT | TACTAGGTTA | ATATAACCTA | TTACTGTAGT 3780 |
| AAAAGAGCAG | GGCCCATCCA | ACAAAGAAA | TATCTATAAA | CTATAGGGTT | TCAAAGTTTG 3840 |
| AAGTCAGTGG | GAAAAATTTT | AAAACCTGAT | GTAAGTAAAA | ACCCAAAACT | GTAATCATCC 3900 |
| ATGTCTATCA | TACACTTGTG | TCTGACAGGC | AAACGGGTGA | ACCACCTCTA | GAGAATGGAT 3960 |
| TAATTCCATA | CCTGGGCTGT | GCTCTGCAAT | TTGGTGCCAA | TCCTCTTGAG | TTCCTCAGAG 4020 |
| CAAATCAAAG | GAAACATGGT | CATGTTTTTA | CCTGCAAACT | AATGGGAAAA | TATGTCCATT 4080 |
| TCATCACAAA | TCCCTTGTCA | TACCATAAGG | TGTTGTGCCA | CGGAAAATAT | TTTGATTGGA 4140 |
| AAAAATTTCA | CTTTGCTACT | TCTGCGAAGG | TAAGCAGTTT | TACATTTATA | TACCATTCTG 4200 |
| TTTGTCTTCT | ACCTTTTTAT | GTGCTTGTCT | ATTTAGAAAT | TTTGATGTAC | TTAGATTTTA 4260 |
| TGATAAAGGT | GTTGAAGAGA | GTTATCCTTA | TGTGGAGATT | CTTAGAAACA | TAAATAAATT 4320 |
| ATACGTAGCT | TCTTAGTAAT | AATCATTTAG | AAAGTCAAAA | TAGGTATAGA | TTTCCGTCAT 4380 |
| TTGCTTTGCA | CGAGCTAATG | AGGGTGAAAT | ACAGATTAAA | TGCTCTACTG | AGACAGGTGG 4440 |
| CACTGTACGA | ATAAGATAGA | TTAAAATTCA | TCACATCAGC | AATGTCTATG | CAGAGCGAAG 4500 |
| TGACGGAAAC | CTAACATTCA | GCAGTTGTCT | CACCACACTT | GTGCCACACA | GTGTTTCATT 4560 |
| TTGATAAGGA | ATTGGCAAGA | TATTTAACA | TCATTTAGAT | GTAATAAAAG | AAGATCTGTT 4620 |
| ACTGAGAAAA | AAAACCAATA | ACTACTTACT | TACTGCAAAT | AAATATTAGC | TTTGGTCTTT 4680 |
| GTGACTAAGT | AGCTTAAAGT | TTGGTTAAAA | TACATCTACA | GCTGGACACA | ATGGAACACA 4740 |
| CCTGTAGTCC | CTGCTATTTG | AGAGGCTGAG | GCAGGAGGAT | CGCTTGAGTC | CAGGAGTTTG 4800 |
| AGGCTGCAGT | GAGCTATCAT | TGTGTCACTG | CACTCCAGCC | TGGGTGACAA | TGTGAGACCC 4860 |
| CATCTCTAAA | AGAAAAGAA | AAAGAAATCT | ACAAATAATA | TAAAGATAA | CTAATGATTT 4920 |
| TAAAACATTA | TCAATTAGTT | TATGTGCAAT | AGCTGTAAAT | AAGTGCAGTA | GCATAAGAAA 4980 |
| TAAGACATAG | ATGACTTGAG | TGATCCAGGG | GAGTGCCACT | GAAGTTGGCT | TTAAAGGAAA 5040 |
| GGTACAGTTT | GGTCATTTAT | TTGTAAAGTG | CTATGAACTT | GTACAAGGGA | AAGCCAATTT 5100 |
| CCCGTGTTTA | CCAAGTAAGG | AACTATGAAA | GTATCTAATC | CGTTTTCAG | TCATTTACTA 5160 |
| TGACTAGGTC | AGGTTTAACT | TCTTTTTCTG | CATGTTTTAT | TTGCTATCAG | GCATTTGGGC 5220 |
| ACAGAAGCAT | TGACCCGATG | GATGGAAATA | CCACTGAAAA | CATAAACGAC | ACTTTCATCA 5280 |
| AAACCCTGCA | GGGCCATGCC | TTGAATTCCC | TCACGGAAAG | CATGATGGAA | AACCTCCAAC 5340 |
| GTATCATGAG | ACCTCCAGTC | TCCTCTAACT | CAAAGACCGC | TGCCTGGGTG | ACAGAAGGGA 5400 |
| TGTATTCTTT | CTGCTACCGA | GTGATGTTTG | AAGCTGGGTA | TTTAACTATC | TTTGGCAGAG 5460 |
| ATCTTACAAG | GCGGGACACA | CAGAAAGCAC | ATATTCTAAA | CAATCTTGAC | AACTTCAAGC 5520 |
| AATTCGACAA | AGTCTTT | | | | 5537 |

( 2 ) INFORMATION FOR SEQ ID NO:33:

( i ) SEQUENCE CHARACTERISTICS:
        ( A ) LENGTH: 2575 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

| | | | | | | |
|---|---|---|---|---|---|---|
| GAATTCTACT | CTTTAAAGGG | GTGAATATTA | TGGTACTTGA | ATTTTATCTC | AAGAAAAATG | 60 |
| AATAAAAAGT | AACTAAATCA | TTGAAAATAT | CTGATGGCAT | GGGGTTTGTG | GGGTAACTGG | 120 |
| CATTCCACAG | TGATTTTCAA | AGGGCTTGTG | CTGTTTTCAT | TTGCTTTGT | TTTAGTTATG | 180 |
| GAGCCCTTCC | TTGAAACAAA | CTTCATACTA | CAGTCCTCTT | TCATGAAGCA | GAAGAGGGCA | 240 |
| GTGGGCAGAG | CTCTCCTTTG | GCTTTCTCCC | CCACCACAAC | AGGGAGCCCT | GGAGCTCTAG | 300 |
| GAGAGAAAAT | CTGAAATATA | AAGGGCATGC | ATGTGAGCTG | TGGAGTCCCA | GAGCCCTGGG | 360 |
| TTTGCATCCT | AGATCTGCAA | CTCCCGTGAA | TTGAGTTTTG | GGAAGTTGCT | GAAACTCTGA | 420 |
| CCTCCTGTTT | TCTCATGGTA | TTGTTGTAAG | GGTTAAATGA | GACAATGTAT | GTGAAGACCC | 480 |
| TGGCCCCACA | GTAGAGGCTC | TGCACACATT | TCAGCGATAC | TTTCCTCATG | TATTTCCAAA | 540 |
| AATGTTTTCT | CATTTCTTA | AAATGTCAGA | AAGAAGACAA | CAGAACTTAC | TTGCCTTTTA | 600 |
| CAACAGAACA | AATGGAGCAA | GTCAGAGGTC | AAGGTGCTAA | CATTCTTCAT | GGTTCCTCAC | 660 |
| CACCTTTTGT | TCTGTTAGCC | TATAGGGAAA | AGTCTTCTTT | CTCATCTCAT | TATCTGCAGG | 720 |
| GGAAAATAGT | ACTTCAGCAA | GTGATCCAGT | TGAAGAACAT | CTCCAGGGCC | ATTAACATAC | 780 |
| AGAGGTTTGT | TCTACTCTCT | CTGTGCTCCA | TGTCTAAGAA | CCTCAGCCTT | CCTCCTAGGA | 840 |
| GCTAGGGAAA | GTCAGGAAAG | TGAAAATAGT | ACCCCAGCTA | ATGAACTGCC | CTGTGCTGGC | 900 |
| CTGAGAAGAC | AAGACCAGCT | TCCTCAATGG | CTCAAGATTT | GGTTTCCTTC | AATATGTCCT | 960 |
| TTTGGAAATA | TGTCCATGAC | ATCGGAGAGA | TAAAAGGAGC | CAGGATTGCT | CACATTCAGG | 1020 |
| AAAAAAGCTC | CACTATCTTT | CTCTCTCTCC | CTCTTTCTCT | CCCTCCCCCT | GACTGCCCTC | 1080 |
| TTCTCTATCT | CTCTCTCTCC | CTGAGCTGGC | AAGGTTAATT | GGTCGCAGAA | AGCCGAAGAA | 1140 |
| ACAAGTGGGC | CTCCTGGAAC | AAAGTTCAAA | AAGCCGAAAA | CGGGAAGAAA | ACTAACCACA | 1200 |
| AAAGTAAAGG | AACCACTTAG | CCTTCTTTGA | TTCCAGGCCC | CCAAGCCTGT | CTTTAACTTG | 1260 |
| GATGAATGGA | GTTCTTCCTG | TGCTACAGCA | CCGCATAGTA | GGGGCTGCCC | TGGGCCTGAA | 1320 |
| GCCAGAGCTT | CACCATATTC | AGTCATCTGT | ACATTGAGGC | AACAGTGCCT | GCTTCATGGT | 1380 |
| GCTACCCTGT | GGATTAAATG | AAGCAAGTTT | TTGATGATCT | TGACACTGAA | TATTGATGCA | 1440 |
| TTGGTCAGAC | TTTTTCTGAT | AGTAAAAAAT | GGTGGTTTCT | TGTTGTCAGA | AATCAAATCA | 1500 |
| ATATATTTGT | TCTCCTGTTG | ATTAGCTATG | TCCCTAGAG | GGCAGCGACT | TTGCCTGTCT | 1560 |
| TATTTATCTC | TGCATCTCCA | GCACTTAAAA | GGTGCCTTGC | ATAAGGTACA | TATTAAGTTC | 1620 |
| ATATGAATGA | ATGAATGAAA | TGCATATGAT | TTATTCATAC | CCAGTTGGTG | GTGTGTTTAC | 1680 |
| CCTTTCCTAA | ACCTGTAGTC | AGATGGCCTT | TGAATCCCCT | GTACTTCTTG | TGAGGTACTG | 1740 |
| TGCTGTAAAG | GTGGACTATC | ACACTTCAGT | TCAGAGCAAT | CTGGGCTTGA | ATCCTGGATT | 1800 |
| TGCCAGTTTA | TTAACTATAG | CAAACATTTT | TGAGCATACA | TTGTGCCAAG | TGCTAGGCTA | 1860 |
| ACTGTCTTAC | ACACATTGTC | TTATTTCGTC | TTAATATCTA | TGAGTCATGC | ACTATAATCA | 1920 |
| TCCCCATTTT | ACAGATAAGA | AAGCAAAGAC | TTGGAGAGGA | AAAGCATCTT | GTTCAAAGGT | 1980 |
| AAATACTTAA | TGGCCAAGCC | AACATGCAAA | TCTAGATTTA | ATTGCAGCTT | CCTCTTCATC | 2040 |
| TACCATTCGA | ACTAATTCAA | GCTATGTAAT | ATTTCCCACT | GAACCTTCTT | GCCTCTACTT | 2100 |
| CCTCATCTTT | AACATGGTCA | AATACCTGT | CCTGCCCAAG | TTAGTTATTT | CATTAAAGTA | 2160 |
| GAAAAATACA | AGAGAAGCTT | TTAAAATGTG | AAACCTCAAA | TGAATGTAAA | ATTATGATGA | 2220 |
| TTCCTTTAGA | ATTTGTCAAC | ACCTTCTTTT | CTCTACTCCT | GCTAGGCATT | TACAATCTCA | 2280 |
| AAACCATGTA | TTTAAGATGC | AAAACTATAT | TTGTATTTGC | CATAACTGGT | TTCTTTCCCT | 2340 |

| | | | | | |
|---|---|---|---|---|---|
| ATGGCTTCAT | GAAAATGTGG | CTCGAATGTG | TTTATTATGA | AAGCCCCAAA | TTAATCACGA | 2400 |
| CAAGACTTCA | CCAGCCCATT | CCACAATAGA | CTCCCATTAC | TTTGCCCTGA | CTTAGAAACC | 2460 |
| TCATATACAG | TCTTGATTCA | GTACAGCTCT | GTGATGCTCT | TGGAAAATGC | AAAGTGCTTT | 2520 |
| CTTAATTGAG | GCAATCTGTG | TCCCACTACA | GAGAGGTGGT | TTAACTTGTG | AATTC | 2575 |

( 2 ) INFORMATION FOR SEQ ID NO:34:

( i ) SEQUENCE CHARACTERISTICS:
        ( A ) LENGTH: 2316 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

| | | | | | |
|---|---|---|---|---|---|
| AGAGCAACCT | GGGCAACATA | GCAAACCCT | GTCTCTGCAA | ACAATAAAAA | GAAGAAAATT | 60 |
| AGCTGGGTAT | GGTGGCACAT | GCTATAGTCG | CAGCTACTCG | AGAGGTTGAG | GTGGGAGGAT | 120 |
| CAGTTCAGCC | TGGGAGGTTG | AGGCTGCAGT | GAGCCAGATC | ATGCCACTGC | ACTGCAGCAT | 180 |
| GGGCAACAGA | ATGAGACCCT | GGCTAAAAGA | AAACAAAATA | AAAATTCAG | ACACAGGTTG | 240 |
| AATCATTGAT | AACAGCATAG | TGGTAACAGA | AAGAAAGTTT | GGGAAATTTT | TATCTGATCA | 300 |
| GCTTCCCATA | CCCTGTTCAT | CTTTGTGTTA | TGCACTGCCA | GGCTGTCTGT | AGGTTCAGAC | 360 |
| TCTATATCAT | ATGACCTTCA | AACACTTGGT | TTGTTCTTCT | CCTTCCTTCC | TCCCTTCTTC | 420 |
| TTTCATTTTT | TATCTTTTTT | TCTTTTAAAA | TGTTTAGATA | GTATAATAAG | GAACTGCTGA | 480 |
| GGCTTTCCAG | TGCCTCCCTC | AACATCCGGA | CAGCTAAGGA | GGATTTCACT | TTGCACCTTG | 540 |
| AGGACGGTTC | CTACAACATC | CGAAAGATG | ACATCATAGC | TCTTTACCCA | CAGTTAATGC | 600 |
| ACTTAGATCC | AGAAATCTAC | CCAGACCCTT | TGGTAAAGTC | GCAGTGTGCC | CGAATTGAAA | 660 |
| TTCAATATCC | AGGTGATAGC | TACCTAGATC | TAAATAAAGA | GGAAATTTAC | AATGGTAGAA | 720 |
| TTGATTTTCT | CATAGTAGTC | ACAGGAATTG | TCTGACTTAA | TTGTGTTAAA | TATTCATATA | 780 |
| TTTTGGAAAA | TTTAGATAGT | GGTCTGAATT | TTTCATTTTA | GTCCTGATAT | TTGCCATCAC | 840 |
| ACAGTCTTTG | CTAGATTATA | TTTGCAGTCA | TGATAATAAA | CCTGCCACTT | TTTTTTTCTT | 900 |
| AAAAAGCACC | TCCTCCCAAA | TCCAGGAAAT | TGGAGGCTAA | TATATTGATT | ATTCTAGTTT | 960 |
| CTTCTGGGAA | CCCTTCTCTC | TCTAGCTCTG | CCTGACTAAG | GAACTAATCG | TTCAAGCAGG | 1020 |
| ATAGGAAGGT | ATCACAAGGC | TTCCTTAGCT | GCATTAAGCT | CCTGTTCCTT | ATTACTTTCT | 1080 |
| GATTCAATGT | GGAGTATTTG | CTAAATCACT | AATGGGGTAG | AATTAAAAAG | AAAATTACTC | 1140 |
| TTTGGAGCTT | CCAGGTTTAG | AAAGAGATAA | ATTTCTTTAA | AACTAGCTTA | AAGGCGGTTT | 1200 |
| TCTTTGTATT | TTTATTGCAG | ACTTTAAAT | ATGATAGGTA | TCTTGATGAA | AACGGGAAGA | 1260 |
| CAAAGACTAC | CTTCTATTGT | AATGGACTCA | AGTTAAAGTA | TTACTACATG | CCCTTTGGAT | 1320 |
| CGGGAGCTAC | AATATGTCCT | GGAAGATTGT | TCGCTATCCA | CGAAATCAAG | CAATTTTTGA | 1380 |
| TTCTGATGCT | TTCTTATTTT | GAATTGGAGC | TTATAGAGGG | CCAAGCTAAA | TGTCCACCTT | 1440 |
| TGGACCAGTC | CCGGGCAGGC | TTGGGCATTT | TGCCGCCATT | GAATGATATT | GAATTTAAAT | 1500 |
| ATAAATTCAA | GCATTTGTGA | ATACATGGCT | GGAATAAGAG | GACACTAGAT | ATTACAGGAC | 1560 |
| TGCAGAACAC | CCTCACCACA | CAGTCCCTTT | GGACAAATGC | ATTAGTGGT | GGCACCACAC | 1620 |
| AGTCCCTTTG | GACAAATGCA | TTTAGTGGTG | GTAGAAATGA | TTCACCAGGT | CCAATGTTGT | 1680 |
| TCACCAGTGC | TTGCTTGTGA | AATCTTAACA | TTTTGGTGAC | AGTTCCAGA | TGCTATCACA | 1740 |
| GACTCTGCTA | GTGAAAAGAA | CTAGTTTCTA | GGAGCACAAT | AATTTGTTTT | CATTTGTATA | 1800 |

| | | | | | |
|---|---|---|---|---|---|
| AGTCCATGAA | TGTTCATATA | GCCAGGGATT | GAAGTTTATT | ATTTTCAAAG | GAAAACACCT | 1860 |
| TTATTTTATT | TTTTTCAAA | ATGAAGATAC | ACATTACAGC | CAGGTGTGG | AGCAGGCACC | 1920 |
| TGTAGTCTTA | GCTACTCGAG | AGGCCAAAGA | AGGAGGATGC | TTGAGCCCAG | GAGTTCAAGA | 1980 |
| CCAGCCTGGA | CAGCTTAGTG | AGATCCCGTC | TCCAAAGAAA | AGATATGTAT | TCTAATTGGC | 2040 |
| AGATTGTTTT | TTCCTAAGGA | AACTGCTTTA | TTTTATAAA | ACTGCCTGAC | AATTATGAAA | 2100 |
| AAATGTTCAA | ATTCACGTTC | TAGTGAAACT | GCATTATTTG | TTGACTAGAT | GGTGGGGTTC | 2160 |
| TTCGGGTGTG | ATCATATATC | ATAAAGGATA | TTTCAAATGT | TATGATTAGT | TATGTCTTTT | 2220 |
| AATAAAAAGG | AAATATTTTT | CAACTTCTTC | TATATCCAAA | ATTCAGGGCT | TTAAACATGA | 2280 |
| TTATCTTGAT | TTCCCAAAAA | CACTAAAGGT | GGTTTT | | | 2316 |

( 2 ) INFORMATION FOR SEQ ID NO:35:

( i ) SEQUENCE CHARACTERISTICS:
        ( A ) LENGTH: 10614 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

| | | | | | |
|---|---|---|---|---|---|
| GAATTCTAAA | CACATATTAA | TATCAATGAC | TTATATGTAT | GTATATATAT | ATCTAATATA | 60 |
| GATAATGTAT | CTAGGGATAT | ATATATATGT | ATATTTATC | TTTCTTCCTT | TTATTCTTTC | 120 |
| TTCTCCCCTC | TCTGTTCAAC | ACCGAGGAAT | AGAATGCACT | GTGGTGTCAT | ACTCTGCTTA | 180 |
| CTCAGCCTCT | TATTGACCTC | TGAGTCAATA | CAGTGCTGAT | GTACATCTCC | AAATGCCCTC | 240 |
| TTTTCTCCTA | ACCACAGACT | TTTACATTCA | GTAATCAATT | TGACATTGTC | CCATGATTTA | 300 |
| CAAATGTTCA | CAATAGTATA | TTGACCTATT | GCTGCCTTCC | AAGGTCCTCT | CCCACTCCCA | 360 |
| AACATCCCAA | TATGAACCAG | CTTTTGCCTA | TCTTCTTGTC | TCTTACTTTA | ACTCAATGTC | 420 |
| ATTCCCTATT | CACTTTGCTG | TAATAGATGC | TACCTTGATT | CTGGTTTTA | GCACCTTAAT | 480 |
| TTCGCTCTCT | GCTCAGGAAC | TCTGCCTTTG | CTGTTCCCTC | TTCTGGGAAC | GCTTTTCCTT | 540 |
| TGCTGTTATA | TCTCTTCAAA | ACAGCTTCTC | TATTCAATAT | GCTCAAGCTG | CCTTCAGCCC | 600 |
| TCAACAGCTC | TCCCTACCTC | ATTCTAGTCC | CTCCACTAGA | ATAGAATCTT | CATGAGAGTA | 660 |
| GCGAACTTCC | CTATCTTGCT | AGTACCCAAA | GGCAGAAAAA | TCTTTAAAGA | GTTCCTGGGA | 720 |
| CATAGAAAAA | GTGCTCAATT | AATATTTGTA | TTAAATAGGG | ACCTCAGGTG | TAACTCCGTG | 780 |
| GTAGAGCGTT | TGCCTTAGAG | AAGTAGGGCC | ATGGGTTCAA | ATTCCAGCAC | AGAACAAAAA | 840 |
| ATTGTGCTGA | ATAAAGTTTG | GGAGGATGTG | TAGCAGTTTA | TAGTGCAAGT | GGCATAAGCA | 900 |
| GTAAATAATG | AATTTGTATC | CACTTTTCTA | GCAAGAAGTA | TTTTATTCTT | TATTTGAAGG | 960 |
| ATAACAATTG | GTAAAGACTG | CATTCTCAAA | ATAAACTATG | GCTTATGGCT | ACGTGGAAGA | 1020 |
| TGAGATAGGG | AGAAGGTTTT | TTTTTGATGA | TGGCAAAATA | ACATGTCATA | GTCCACACGA | 1080 |
| AACACCTGTG | AAGTTGTAAA | CACACCTAGC | AATCAAACAA | GAAAATTGTC | CCACCCTATT | 1140 |
| ATCATTCTTT | TGGATTGGTT | GTGGCATATT | TCTGGAAAAT | GATTTAAATT | AATTCCTTCT | 1200 |
| AAAGGTAACA | ACACAAACAA | CCACTATCAT | GACGAAAAGC | TTCTGCCTGT | TTCAGTTTAC | 1260 |
| ATCATGCTCA | ATGTCTACAA | CAGACGTGCT | CATCTTCAGA | GTGTTACCT | CTGCTTTTTA | 1320 |
| CACACATTGA | AGCACAATGT | GAGCTGCTGT | CCCTGGGTCT | GAATGTTATG | TCAGCACACA | 1380 |
| AGGGACAGAG | CTTCGGCTTA | TCAAGTATTG | AAGCTCTCTG | CTTGTTTTGG | AGCCTCTTCT | 1440 |

| | | | | | |
|---|---|---|---|---|---|
| GATACTATGG | ACTTAGTTCA | AGGCTGGGCA | ATACTATTTT | TTTCTTTTTT | CTAATAGGAG | 1500 |
| GACAAATAGT | TAGTTGTTTG | CTTTGGTCAT | CCAAGTTCAA | GTTATTGGAT | CATGGTCCTA | 1560 |
| TGTGTATAAA | GAGTCTAGTT | TGAGCCTTTC | AGGGGCAGCC | TTGCTGGCTA | AGCACAGACT | 1620 |
| CTCCTCTTGG | GAGTTTTCCT | GCTTTGCAAA | ATGATGACCA | TCTCTTTGAT | TTGGGGGATT | 1680 |
| GCTATGGTAG | TGTGCTGTTG | TATATGGGTT | ATCTTTGACA | GAAGGAGAAG | GTATGTCTTT | 1740 |
| TAGCTTATTT | CTAGTGTTTT | CACTATTATA | CAGTTCCAAA | AAATACTAG | TACATTAGTA | 1800 |
| TTTTTATTTA | AAATTTAAAG | CCATGCTTCT | TTGACTAAAC | CTGACAAGAT | GTAGAGTTTC | 1860 |
| CCTTTGAATA | TCCACATACA | CTGATGGTAA | TGCTGATCTT | GTTAAACATA | ACTAAAAAAA | 1920 |
| TTATAAGTAT | TGATGCATGT | TTGTGTGCAC | TTCTGTGGAG | TACACCTAAG | CTGGGAAGGG | 1980 |
| TGCATTTGGC | AAGGGTGACG | TTTGGAAAGG | ATCTTTCTCT | CACAATAACT | GGTTATGCAT | 2040 |
| ATGCTCTTCT | GGGTTCTCTG | TTACATCAAC | ATTAAAATAC | AGGAATACCC | TTGGCATATC | 2100 |
| TTTGGCAAGG | TAGACTGTGT | CTGCTGTCTT | AGTTTTAATA | ACTTCTTTGC | CTTTTGAGTT | 2160 |
| ATTTGAATTT | ATGCCTGATC | GTTCCAGTT | TTAGTTGTCT | TAATGCTAAG | AAAGGACAAA | 2220 |
| TCAATTATAT | TTAGTTATTC | TAACAAGAGA | TAACTAGTTT | ACGTTGAAAA | ATAAATTATC | 2280 |
| TTATAATTTC | TAATAAAAAC | ATTTAAGAGA | GTTAGAAATC | AGCGAATTAT | AGCTGATGAT | 2340 |
| CTGCCAATGT | TTACCTCACT | CAACTTCATT | TTAGATACTT | TTTCAAGTGG | GATTCCTATT | 2400 |
| CTCTTCAAAT | ATCCGCACAG | AATTATAGTC | CCCTTCTTTC | AGAGTGGGGG | GAATCAAATG | 2460 |
| AAAGGTTTCA | TGTGTGCTAG | GCAAGAGCAC | CACCGTTGAG | CCACACCTCC | AGACCCCACA | 2520 |
| ATGCCAACAT | TTTTAAACTA | TGTAGAGTTT | AAAAAACTTT | AGTTCTGTAG | CCTTTTCTAT | 2580 |
| TAGCTGGTGT | TTCATGTCTT | CAAAGAAAAG | GAAAACTGAA | ACATTTAGA | CATATGGACA | 2640 |
| AATGATTCCT | TGAACAAGTC | TAAGCACTGA | TGATAGCTTC | TTTTCTACAG | TGAGATCAAG | 2700 |
| AATCTTGTTA | GCCCTGTTGA | TACTTGTAGC | CCTGTCACTT | GGAAAAGCAA | TCAATTTTAT | 2760 |
| GATCTAGAAA | ATAGAGCTTG | CCTAAAGATC | AGAGTGCAGA | GCTAGTCACA | CTAGTCAGCC | 2820 |
| ATACAGGTTA | GGCAGTGGTG | GCACATACCT | TTAATCCCTG | CAGCCACTCA | AGTTACCCAT | 2880 |
| AGAAGCTGGG | TGGTGGTGGT | GCACACCCTT | AATATAAGGT | GGAGCACACT | TTAATGTAAG | 2940 |
| GTGGGTAGAG | TCAGGAGTGC | AGTGTATTCA | GTCTGCAGTC | ACACTGAGAA | CAATATCACC | 3000 |
| CCAGTCTTGT | TAGAGGTAAG | AACTCTCTAG | TGATTGGCTG | CTTTGCTCTT | CTGATCTTCA | 3060 |
| GTTTGAACTT | CTGTCTCTGG | GTTTTTATTA | TTCGTGCTGC | AGACATAGAC | ATAGCAAACA | 3120 |
| ATTTAATGAG | TGATTGATGA | ATGTAGATAT | GTATGTACAT | ATTGTGCTGG | ATAGACTGTA | 3180 |
| GATGGGTTGG | TGGATGGGTT | GATGAGTGGG | TAGATTTAGT | AATCACCTTC | ACCAATATCT | 3240 |
| TAGTAGGCTA | AAAAGCCCAC | TGTTTTAGTA | AAAGAGTGGG | GTATCCAACA | AAGAAGTATC | 3300 |
| TATAAACTGT | AGTTATGTGG | TAGAAATAAG | GGGTAGAAAC | CAGTAAAAAT | TCGGCTTATG | 3360 |
| TACAAATGCT | AAACATGTAA | TTTCCTAAAC | CTCTCAATCT | GTCTCACAGG | AAAGCAGGTG | 3420 |
| AACCTCCTTT | GGAGAATGGG | TTGATTCCAT | ACCTGGGCTG | TGCTCTGAAA | TTTGGCTCTA | 3480 |
| ATCCTCTTGA | GTTCCTGAGA | GCAAATCAAA | GAAAGCACGG | TCATGTTTTT | ACCTGCAAAT | 3540 |
| TAATGGGGAA | ATATGTTCAC | TTCATCACAA | ACTCCTTGTC | ATACCATAAG | GTGTTATGTC | 3600 |
| ATGGAAAATA | CTTTGATTGG | AAAAAATTTC | ATTACACTAC | TTCTGCAAAG | GTAACTAGTT | 3660 |
| TTTACAGATT | TTGCTTGTTT | ACTAGCCTGT | TTATTTATTA | GTTATTTAG | TTGTTCCAAT | 3720 |
| GTTATTAGAT | TGTAGGATAA | AGGGAACATA | AAATCAGGAA | GTCTCTTGGT | ACTAAGCATT | 3780 |
| AAAAAGTCAA | GGTAAATGTG | AATTTGTGAT | TGATGATGAC | ATACACAAAT | TAAGCACTTT | 3840 |

```
GTAAGTACTT TCTGAGCCAG AAGACACTAC AGGAAGGCAC AGACTCATAA CATCCATGCT    3900

GCCATCTACA CAACACTCAG AGCACTCAAT TACCACATCA TGCACACGAA CTCGTTCGTT    3960

AAGAAGTCGA CAGTATATTT AAGCATCATT CAGATGTTAT CAAGAATCTC TATTCTAGAG    4020

AAAACAACAC TTAGCTGAAT TTTTACAAGA AAATATTAGA CATGGTCTCT GTCTTAAGTA    4080

GATTAAAGTC TGGCTAAAGT GCATCTGCAG AGAACAAAAG GTAAAGATAA AATCAATGGC    4140

CCATTAGTCC AGAGAAGCTT ACCTGAAAAT CTGGGATTTA AACTTGACCT TAAAGGAAGA    4200

GTATGTCTTA AGTTTGACTT TGAAAAATGT TATGAAATTG TATTGGGAAG GCTAGACAGA    4260

GAAGTATGAT ATACTTTAAT CCATCTTCCA GCCATTTCCT AACACCCAGG TTTAGCTGCT    4320

CCCCCTCTGA CGAATTTCAT TTTCTACCAG GCATTTGGAC ACAGAAGCAT TGACCCAAAT    4380

GATGGAAATA CCACAGAAAA CATAAACAAC ACTTTTACCA AGACCCTCCA GGGAGATGCT    4440

TTGCATTCAC TCTCTGAAGC CATGATGCAA AACCTTCAAT TTGTTCTGAG GCCTCCTGAT    4500

CTTCCTAAAT CAAGAGTGA TGCCTGGGTC ACCGAAGGGA TGTATGCCTT CTGCTACCGA    4560

GTGATGTTTG AAGCTGGATA TCTAACTCTG TTTGGCAGGG ATACTTCAAA GCCAGACACA    4620

CAAAGAGTGC TTATCCTGAA CAACCTTAAC AGCTTCAAGC AATTTGATCA AGTCTTTCCG    4680

GCGTTGGTGG CAGGCCTCCC TATTCACTTG TTCAAGGCGG CACATAAGGC CCGGGAACAG    4740

CTGGCTGAGG GCTTGAAGCA TGAGAACCTC TCTGTGAGGG ACCAGGTCTC GGAACTGATA    4800

CGTCTACGCA TGTTTCTCAA TGACACTCTC TCTACCTTTG ATGACATGGA GAAGGCCAAG    4860

ACACACCTCG CTATCCTCTG GGCCTCTCAG GCAAACACTA TTCCTGCAAC CTTCTGGAGC    4920

TTATTTCAAA TGATCAGGTG GATAGCAATT TGAGTGTTTA TTCTTCATAG TGACAGAAAT    4980

TAACAATTTT TAATAAACCC CCCAAAAGAC TAGCAGAGCT TTCTTTGCTG TTGGTCAAGA    5040

ATGTGATACT CAGTGCCTGT GTTTGACATA TATATATAAC AAAAGTAGCA TTTTGTAAGA    5100

ATATAGTCTC ACCAGAAAGG GATGTCCCAG AAGCCGCAGA ACTTAGATCT GCTGGCACTT    5160

GTCATTAAAG GTCCCCTTGC CCAGTCTTGC TTTTAACTCC ATAGTGTTCT TCTTAGTGTC    5220

AAGTTAAATC TATGACTGCA GTCTTCATCA CAACTTTAAA TAATGACTGA CTTGTCAATG    5280

TGGTAAGTGC AGAGGCCACA CCTTACTAGT TTGAACATTC CTGTTTTCTG CGGCCTCACA    5340

GATTTACAGC AGAGTTGCAA CATCAATTTC ATATTACCTA TGAACTACAA CCATATTTTA    5400

AGTTCAACAA CTACTTGTTA GTAACATTTC TGAGGCTCAG TTCACTTTAA CCAGATAAAG    5460

GAGATTTCAA ACAGCTGCCA ACAAATTTCC ATGCACTGAA TGGAAGTATT CTTTATCGCA    5520

CAGTTCAAAA ATAATAACAT AAATATTCTG AAGCTGTGGT ATGAATTTAA AGAGTAAATT    5580

TGAATTTCTA CTTGGGAATT CACCAATACC CTGTAATTGT ATGTTAGAGG AAGTATTCGG    5640

AATGAATTAC TCTACTCATC ACACGAATGT CTAGCCCTTA TTAGAATCAT TGGTTTATAG    5700

AGATCTGACC AAAGCTTTGC TTTTACATAG CAACGCCCCT TTAATGCTTC TTCATAAATT    5760

CAAGGACATG AATCCAGTTC AGAATACAGT ACAAGTAAAT GACAATGCCC TTTGCATGTT    5820

CCTGGAACCA CTTCCCTTTT CATGCTCCCA TGCTAACGCG ATCACCTCAT TAAAGAAAT     5880

GGAGTTCTTA TTTACTTGCA GCTCTCTGAA TAAGGCAATA TCTTCCATAT GTCTCTTTC     5940

ATAGGAGTCC TGACGCATTG AGAGCAGCCT CTGAAGAAGT GAATGGAGCA TTACAGAGTG    6000

CTGGTCAAAA GCTCAGCTCT GAAGGGAATG CAATTTATTT GGATCAAATA CAACTGAACA    6060

ACCTGCCAGT ACTAGGTGTG TTCCCTATGC TATCCCTCAC TAACATGTCA CTAGTAACAA    6120

TGCTCAACAT ATAATGAATG TACTATATTC TTGATATTTT TGCAACGCTG CAACAGTCTA    6180

ATAACTAGGG TCATCTTCAT TTTTTCTAAC AAACAAGGAA CTGAGACCCA GAGCGTGGGA    6240
```

| | | | | | |
|---|---|---|---|---|---|
| CAGTGGCAAC | CCTGGCATAG | AACATTTGAT | ACTCAGTTGC | TCTAGGTCCT | TGGCCTCCTT | 6300 |
| TCTTAGTCCT | CCAAAACCAC | AAACCCAGGG | TTAAGGAAGC | ATGGAATTAA | TGTGAACAAA | 6360 |
| GCAACACCAT | TGGTTTGGGC | GATGAGACTG | AGGCTTTTCT | TCCTTTGTTT | CTGTATTTTC | 6420 |
| TAGAATGCAG | TAGTACCATG | TATTACAGTA | AAACAGCCAT | ATTTTGTGT | CCTGTTCTGT | 6480 |
| AAAGGACAGA | AGCCCCCATA | TGCTTTGAGG | GCAGTTAGT | TTATTAGAAG | CAACAGAGCC | 6540 |
| TAGATTCAGC | ACTGCCTGGT | TTGGGACCTC | CCTTTAGACA | CCTCCTTTT | CTCACCTGTA | 6600 |
| AATAAAGGCT | AAGTAAGCAT | TTGTGACTGC | ATACTCAGTC | ATGGCCTGAA | TCCTGGGAAC | 6660 |
| AAGGCAGCTA | GCAGCTAGAG | GCTGGAAAAC | AGGACTGGAC | CTCAGCAGCT | CTACTGCATT | 6720 |
| ACTTCCCCTA | GAAGCAGGGT | GTGGCTACAC | AAAACCAGAC | AGATAATGTA | TGGCTGAATG | 6780 |
| TAGATTCATG | AAATGCTTGG | AAAGACATTT | ACTTATCAGT | ATGTTTAATT | CCCAAAATGG | 6840 |
| TCAGCAACAA | TTCACACAAA | ATTGATTATA | AGTTTTTTCA | ATTTGCTTAG | CTGTTAGTG | 6900 |
| TCCAGTAGAA | ATAAGATTAC | TATTCTATAA | AGTGACAGAT | GTTCATCTAG | TTCCCATTGA | 6960 |
| TGGTGAAGAA | CATTATGTCA | TCCCAAAAGA | TCGTTAACTT | AGATCGTGGT | TCTCTACCTT | 7020 |
| CCTGATGTTG | TGTGACCCCC | AACTGTGAAA | TTATTTCAT | TGCTACTTCA | CAACTATAAT | 7080 |
| TTTGCTTCTG | TCATGAATCA | TAAAGCAAAT | ATCTGTGTTT | TCTGATGGTC | TTAGGTGACC | 7140 |
| CCTGTGAAAG | GGTCATTTGA | CTCTACCCCC | TACATGGGTT | GTGATCCACA | GGTTGAGAAG | 7200 |
| CACTGACTTA | GATTCTCAGA | TTGCAAGTAG | AGCAGCAGAA | TTTCGAAGAA | CAGCAGTGGC | 7260 |
| GACAGAAGCT | GCTTTGGGCA | GTTGTCATTT | GTTAGCTTTC | ATTGGCTCAT | TTTGTATACA | 7320 |
| GATTTTCGGA | AGTATTTCAG | ACTTTATGTT | ATGTAGCCTT | TAGAGGCAAC | AGTTCAGGAC | 7380 |
| TGGAGAGATG | GCTCAAGGGT | TAAGAGCACT | GGCTGTTTTT | TCAGAGGACC | CATGTTTGAC | 7440 |
| TCACAGCACA | CACATGGTGG | CTCACAGCCA | TCATGACTCC | TGTTCCAAAG | GATCTGATGT | 7500 |
| CTTCTTCTGA | CCTCTGCAGA | CACCAGGCAT | GCATACATGC | AGGCAAAATA | CCCATCAATA | 7560 |
| TAAAAATAAA | TAACTGGGAA | ATATGCAAAT | TCTTTAATAT | GCAAATTCTT | CTCTCCCCAA | 7620 |
| CTGCCATTTC | CCATGCTCCA | CCCTCATCCC | TTCCCTCCTC | TCTTACTTCT | TTTGTTTGGA | 7680 |
| ATTCTTTAGA | TAGCATCATC | AAGGAGGCTC | TGAGGCTTTC | CAGTGCATCC | TTGAATATCC | 7740 |
| GGACTGCTAA | GGAGGATTTC | ACTCTGCACC | TTGAGGATGG | CTCCTATAAC | ATCCGAAAAG | 7800 |
| ACGACATCAT | CGCTCTTTAT | CCACAGTTAA | TGCATTTGGA | TCCTGCAATC | TACCCAGACC | 7860 |
| CTCTGGTAAG | TTTTTCTGCT | CATCAAAGTT | ATGTATCGAG | GTGACAGTCA | CCCAGGAATG | 7920 |
| TATTTGTAAT | TACAGCTTTG | ATTTGATCAT | TAAAGTGAAG | CCATAGGGAT | TGTCCCTCTT | 7980 |
| TATTGCGGCA | AATATTCATG | TTTTGGAAAC | TTTGGGTAGA | GGCAAGAGTT | TTGAACTTTT | 8040 |
| ACACCTAATA | TTCATTTCAT | AGTTTCTGCT | AGACTATGTT | TTCAGTCATA | ACAAAACTAC | 8100 |
| CACCTTTTTT | CCCCCTCACA | AAGTACCCTC | TCCCAAATTT | ACACTAATGG | AGGGTAATGC | 8160 |
| ATTTGACTTG | ATCCTTAGAG | TAGTTGTTTA | GAGCCATTTT | GCTTCTTTTG | TCTAACTGAA | 8220 |
| GAATTAGTCT | ACAGGTAGAA | CAGGAGGTCC | CTAGAGCTTC | TTGGTCCACC | AGCTCTTCAT | 8280 |
| AAGCTCTTTC | CAGTATCACC | TGGTTCAGTG | CTTGGTGTTT | GCTAACTTGT | AGAGGATGGA | 8340 |
| TTTATTAGTA | GAAAATTACT | CTTTGGATCC | TCCAGGTCAA | GAAGGCAACA | ACTTTCTATC | 8400 |
| ATAATAGCTC | ATTGGCTTCT | TGTCTCTTTG | TTGCAGACTT | TAAATATGA | TCGATACCTG | 8460 |
| GATGAGAACA | AGAAGGCAAA | GACCTCCTTC | TATAGCAATG | GAAACAAACT | AAAGTATTTC | 8520 |
| TATATGCCAT | TTGGATCCGG | AGCTACAATA | TGCCCTGGGA | GACTATTTGC | TGTCCAAGAA | 8580 |
| ATCAAGCAAT | TTTTGATTCT | GATGCTTTCA | TACTTTGAAC | TGGAGCTTGT | GGAGAGTCAT | 8640 |

| | | | | | | |
|---|---|---|---|---|---|---|
| GTCAAGTGTC | CTCCTCTAGA | CCAGTCCAGG | GCAGGCTTGG | GGATTTTGCC | ACCATTAAAT | 8700 |
| GATATTGAGT | TTAAATATAA | ACTGAAACAT | CTGTGACATG | TGGTTGGAAG | AAGAGGACAC | 8760 |
| TGGATGATGT | TGCTGGACTG | CAGCGAGTCT | CACTAAACAA | GCCCTTGGGA | CAAATGCTCT | 8820 |
| CCTTTGCTTC | CCAGCAACTG | ACTGTGCCTA | GGAAAAGAAC | TGGTACCCCC | GGCACCACTC | 8880 |
| TCTGTTCTCA | CTGCCTGAGT | TCCTGGGTGT | TCAGATAGCT | GAGGTCAGAG | TTTCACCACT | 8940 |
| CTTAGAAGCA | ATGTCTTTTG | TTTTTATTTT | CAAAATGAAG | ATACTCCAAT | TGGCAGATTT | 9000 |
| TTTTTCCTAA | GGAAATTGCT | TCATACTTTT | ATGAAAACTG | ATTAATTATG | AAAAGGCTTC | 9060 |
| AAATTCACGT | TTTAGTGAAA | CTGTTATTTT | TTTCACTAGT | GAAGTTCTTC | ATGTGTGAAC | 9120 |
| ATATACTATA | AAAACATTTT | AAGGGATCAT | ATCATGCTTT | GCATAAAGGG | AAAGGAAAAT | 9180 |
| ATTATTCAAC | TTTTTTTTTT | GGTTTTCTA | GACAGGGTTT | CTCTGTGTAG | CTTTGGAGCC | 9240 |
| TATCCTGGCA | CTCACTCTGT | AGAGCAGGCT | TGGTCTTGAA | CTCACAGAGA | TCTGCCTGCC | 9300 |
| TTTGCCTTCC | GAGTGCTGGG | ATTAAAGTCG | TGCGTCACCA | ATGCCTGGCT | ATTTAACTTT | 9360 |
| TTCGATGTCT | AGTGGTGAGA | GCTTTGAAAA | TGATGCTACT | GTGTTGGGAA | TACTATGGGA | 9420 |
| AATTTTGATG | CTTCGCTGTT | ACATTTAAAT | TTATTGCTGC | TGGAAATTGT | CACCCAGTT | 9480 |
| TTCAATTGCC | CCTCTCTCTC | CCTTTTAATA | TTCACACTGA | TGAGCAGAGT | TTTTTAGAGA | 9540 |
| TTAAAAAGAC | CTCCCCAGAG | CCCTGTCTCT | GATGTTTTA | AGCCTTTAAT | CTCAGTACTC | 9600 |
| AGGAGGCAGA | GGCAGGCAGA | GCTCTGTGAG | TTCGAGGCCA | GCCTGATCTA | CAGATCGAGT | 9660 |
| TCCAGGCAAG | CCGGGGCTAC | AGAATGAGAC | CTTGTCACTA | AAAGAAATAA | ATAAGGTCAA | 9720 |
| TTTTATGTCA | CAACTGATTA | TGAATCATTG | TAAAGGATAA | ATTGAAAAAA | AAGAACTCCA | 9780 |
| CGGGAATGAC | CATTTAAATG | GTCTATTTTA | GCTAAAATTA | ACTATGAATT | ATGTGGAGTT | 9840 |
| CATTAAGTGT | ATGTTGACGT | TATATGTTCC | TTTAAAATGT | CTTATGTTTT | ATCTCTGAAT | 9900 |
| GTCTTGTAGA | TGGAGAGCAA | TAATAGTGTT | TAAATACTGA | GTCAATAAGG | TTTTATCTAT | 9960 |
| GTACTTTAAG | AGCATTATTA | GCTGTGTCAT | TTTTACTGAT | ATATCTAATA | TATTTATATG | 10020 |
| TAAATTATAT | TTATCTTTTA | TCTTATACTA | CAAATATAAG | TAAATATTTT | AAAACCAGTA | 10080 |
| ACTTTAAAAT | TACCTACCTT | TCAGAAATGA | AATAAGAAC | ATTTGTGCTT | TAACCTTTGA | 10140 |
| AATAGAATGT | TTATTCATCC | ACTGATAAGT | TAAAATAATT | TTATCTGATT | TGTTTCAAGA | 10200 |
| AACTCAAAAA | TATTCAAAGT | AATCATGCAC | TCAAGGTCT | TCGTAAGGTT | ACAGAAAATT | 10260 |
| CAATAAAATC | TTTTTTGTGT | AGGGACTGAG | TCAGGGTCTA | GAAGATGCTT | GGCAGGTACT | 10320 |
| CCAGTAGTGA | GCTGGATCCA | GAAGATTCCT | TAAACTTTAA | AATCTTAACA | CTAAGTATTA | 10380 |
| TCACAGAGTT | ATTACCTAAG | TAGAATATTT | TTCCTTTCCT | TTTCAATTGA | CAGAGTCCCA | 10440 |
| CAGCAACACA | GCTGGCTGTA | ACTCTTCACA | TAGCTTGCGC | AGGCTTTGAA | CTCACTGTAC | 10500 |
| TCCTGCCTTT | CCTTTTCTAG | GAAATTATTT | TCCACATCAA | GAAAATTTAA | TTGTTCCGAT | 10560 |
| GAGGTATAGA | GTAACAAATT | TCTGTTATAT | ATTCATCTGT | ATTAAACTGA | ATTC | 10614 |